（12）United States Patent
Kato et al.

(10) Patent No.: US 7,906,510 B2
(45) Date of Patent: Mar. 15, 2011

(54) AMIDE DERIVATIVE AND PHARMACEUTICAL COMPOSITION CONTAINING THE SAME

(75) Inventors: Shiro Kato, Sakai (JP); Hiroshi Harada, Osaka (JP); Hiroshi Yamazaki, Suita (JP); Yoko Kan, Osaka (JP); Yoshimi Hirokawa, Ikoma (JP); Takanori Nakamura, Suita (JP)

(73) Assignee: Dainippon Sumito Pharma Co., Ltd., Osaka (JP)

( * ) Notice: Subject to any disclaimer, the term of this patent is extended or adjusted under 35 U.S.C. 154(b) by 0 days.

(21) Appl. No.: 12/734,224

(22) PCT Filed: Feb. 20, 2009

(86) PCT No.: PCT/JP2009/053011
§ 371 (c)(1),
(2), (4) Date: Apr. 19, 2010

(87) PCT Pub. No.: WO2009/104729
PCT Pub. Date: Aug. 27, 2009

(65) Prior Publication Data
US 2010/0249399 A1 Sep. 30, 2010

(30) Foreign Application Priority Data
Feb. 21, 2008 (JP) .................................. 2008-040029

(51) Int. Cl.
*A61K 31/5377* (2006.01)
*C07D 413/02* (2006.01)
*C07D 413/14* (2006.01)

(52) U.S. Cl. ..................................... 514/235.5; 544/129

(58) Field of Classification Search .................. 544/129; 514/235.5
See application file for complete search history.

(56) References Cited

U.S. PATENT DOCUMENTS

| | | | |
|---|---|---|---|
| 4,870,074 A | 9/1989 | Kon et al. | |
| 5,395,832 A | 3/1995 | Ito et al. | |
| 6,100,262 A | 8/2000 | Hendrickx et al. | |
| 6,294,555 B1 | 9/2001 | Kato et al. | |
| 6,696,468 B2 | 2/2004 | Kato et al. | |

FOREIGN PATENT DOCUMENTS

| | | |
|---|---|---|
| EP | 0 243 959 | 11/1987 |
| JP | 63-264467 | 11/1988 |
| JP | 11-1472 | 1/1999 |
| JP | 11-505815 | 5/1999 |
| JP | 2000-80081 | 3/2000 |
| JP | 2001-122784 | 5/2001 |
| JP | 2004-43453 | 2/2004 |
| JP | 2004-277318 | 10/2004 |
| JP | 2004-277319 | 10/2004 |
| JP | 2004-277320 | 10/2004 |
| JP | 2005-82508 | 3/2005 |
| JP | 2005-082508 | 3/2005 |
| JP | 2005-104896 | 4/2005 |
| JP | 2005-170933 | 6/2005 |
| WO | 92/14705 | 9/1992 |
| WO | 96/37486 | 11/1996 |

OTHER PUBLICATIONS

International Search Report issued Mar. 24, 2009 in International (PCT) Application No. PCT/JP2009/053011.
D. A. Craig et al., "Pharmacological Characterization of a Neuronal Receptor for 5-Hydroxytryptamine in Guinea Pig Ileum with Properties Similar to the 5-Hydroxytryptamine$_4$ Receptors[1]", The Journal of Pharmacology and Experimental Therapeutics, vol. 252, No. 3, pp. 1378-1386, 1990. N. Yoshida et al., "AS-4370, A New Gastrokinetic Agent, Enhances Upper Gastrointestinal Motor Activity in Conscious Dogs", The Journal of Pharmacology and Experimental Therapeutics, vol. 257, No. 2, pp. 781-787, 1991.
S. Kato et al., "Synthesis of a New Benzamide with Potent Gastric Prokinetic Activity", Journal of Pharmaceutical Sciences, vol. 76, No. 11, p. S159, Nov. 1987.
S. Kato et al., "Synthesis and Structure-Activity Relationships of a New Gastroprokinetic Agent, AS-4370, and the Related Compounds", J. Pharmacobio-Dyn., vol. 13, p. S146, 1990.
S. Kato et al., "Novel Benzamides as Selective and Potent Gastric Prokinetic Agents. 1. Synthesis and Structure-Activity Relationships of N-[(2-Morpholinyl)alkyl]benzamides", J. Med. Chem., vol. 33, pp. 1406-1413, 1990.

(Continued)

*Primary Examiner* — Rebecca L Anderson
*Assistant Examiner* — Samantha L Shterengarts
(74) *Attorney, Agent, or Firm* — Wenderoth, Lind & Ponack, L.L.P.

(57) ABSTRACT

Disclosed is a compound having a strong affinity to serotonin-4 receptors, which is useful as an enterokinesis-promoting agent or a digestive tract function-improving agent. Specifically, disclosed is a compound represented by Formula (1) or a pharmaceutically acceptable salt thereof. Also specifically disclosed is a pharmaceutical composition containing a compound represented by Formula (1) or a pharmaceutically acceptable salt thereof. [In Formula (1), Ar represents a group represented by Formula (Ar-1) or Formula (Ar-2).]

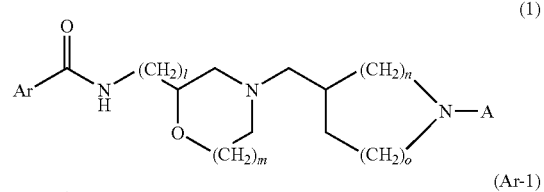

(1)

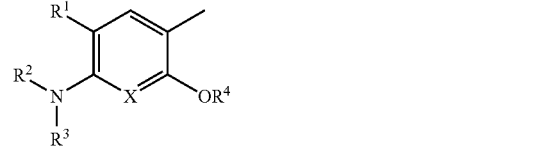

(Ar-1)

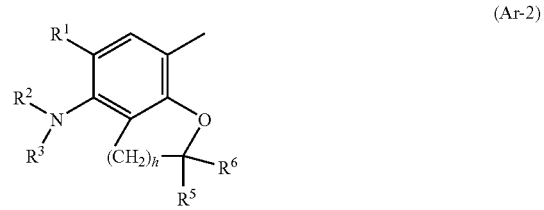

(Ar-2)

30 Claims, No Drawings

OTHER PUBLICATIONS

S. Kato et al., "Novel Benzamides as Selective and Potent Gastrokinetic Agents. 2. Synthesis and Structure-Activity Relationships of 4-Amino-5-chloro-2-ethoxy-N-[[4-(4-fluorobenzyl)-2-morpholinyl]methyl]benzamide Citrate (AS-4370) and Related Compounds", J. Med. Chem., vol. 34, pp. 616-624, 1991.

S. Kato et al., "Novel Benzamides as Selective and Potent Gastrokinetic Agents. III. Synthesis and Structure-Activity Relationships of 4-Amino-5-chloro-2-methoxy- and 2-Ethoxy-N-[(4-substituted 2-morpholinyl)methyl]-benzamides", Chem. Phar. Bull., vol. 40, No. 3, pp. 652-660, 1992.

S. Kato et al., "Novel Benzamides as Selective and Potent Gastrokinetic Agents. IV. Synthesis and Structure-Activity Relationships of 2-Substituted 4-Amino-N-[(4-benzyl-2-morpholinyl)methyl]-5-chlorobenzamides", Chem. Pharm. Bull., vol. 40, No. 6, pp. 1470-1475, 1992.

N. Yoshida et al., "Pharmacological Effects of the New Gastroprokinetic Agent Mosapride Citrate and its Metabolites in Experimental Animals", Arzneim.Forsch./Drug Res., vol. 43, No. 10, pp. 1078-1083, 1993.

N. Yoshida et al., "Mosapride Citrate", Drugs of the Future, vol. 18, No. 6, pp. 513-515, 1993.

T. Morie et al., "Synthesis and Biological Activities of the Optical Isomers (±)-4-Amino-5-chloro-2-ethoxy-N-[[4-(4-fluorobenzyl)-2-morpholinyl]methyl]benzamide (Mosapride)", Chem. Pharm. Bull., vol. 42, No. 4, pp. 877-882, 1994.

T. Morie et al., "Asymmetric Synthesis of the Enantiomers of 2-Aminomethyl-4-(4-Fluorobenzyl)Morpholine, An Intermediate of Mosapride, A Gastroprokinetic Agent", Heterocycles, vol. 38, pp. 1033-1040, 1994.

S. Kato et al., "Synthesis and Gastroprokinetic Activity of 2-Amino-N-[(benzyl-2-morpholinyl)methyl]benzamide Derivatives", Chem. Phar. Bull., vol. 43, No. 4, pp. 582-587, 1995.

S. Kato et al., "Synthesis and Biological Activities of Metabolites of Mosapride, A New Gastroprokinetic Agent", Chem. Pharm. Bull., vol. 43, No. 4, pp. 699-702, 1995.

S. Kato et al., "Synthesis and Gastroprokinetic Activity of N-(4-amino-5-chloro-2-methoxyphenyl)-4-benzyl-2-morpholineacetamide and Related Compounds", Eur. J. Med. Chem., vol. 30, pp. 609-616, 1995.

S. Kato et al., "Synthesis of Deuterated Mosapride Citrate", Journal of Labelled Compounds and Radiopharmaceuticals, vol. 36, No. 10, pp. 927-932, 1995.

S. Kato et al., "Synthesis and Biological Activity of 4-Amino-5-chloro-2-ethoxy-3-hydroxybenzamides, Metabolites of a New Gastroprokinetic Agent, Mosapride", Chem. Pharm. Bull., vol. 44, No. 8, pp. 1484-1492, 1996.

S. Kato et al., "Synthesis of 4-Chloro-7-ethoxy-2(3$H$)-benzoxazolone-6-carboxylic Acid", J. Heterocyclic Chem., vol. 33, pp. 1171-1178, 1996.

S. Kato et al., "Nitrogen-Containing Heteroalicycles with Serotonin Receptor Binding Affinity: Development of Gastroprokinetic and Antiemetic Agents", Med. Res. Rev., vol. 19, pp. 25-73, 1999.

English translation of International Preliminary Report on Patentability and Written Opinion dated Oct. 5, 2010.

AMIDE DERIVATIVE AND PHARMACEUTICAL COMPOSITION CONTAINING THE SAME

This application is a U.S. national stage of International Application No. PCT/JP2009/053011 filed Feb. 20, 2009.

TECHNICAL FIELD

The present invention relates to a novel amide derivative which is useful as an enterokinesis-promoting agent, etc. and has an agonist activity against serotonin 4 receptor, which is also referred to as a 5-$HT_4$ receptor hereinafter, and a pharmaceutical composition comprising the same.

BACKGROUND ART

A 5-$HT_4$ receptor which was a subtype of serotonin receptor has been found in an action mechanism study of metoclopramide [4-amino-5-chloro-N-(2-diethylaminoethyl)-2-methoxybenzamide] which was an enterokinesis-promoting agent or a digestive tract function -improving agent in widespread clinical use. Thereafter, it became clear that an enterokinesis-promotion activity of benzamide derivatives such as metoclopramide or cisapride {cis-4-amino-5-chloro-N-[1-[3-(4-fluorophenoxy)propyl]-3-methoxy-4-piperidinyl]-2-methoxybenzamide} was caused by stimulating 5-$HT_4$ receptors (see Nonpatent Documents 1 and 2). Further, a 5-$HT_4$ receptor agonist tegaserod [2-(5-methoxy-1H-indol-3-ylmethylene)-N-pentylhydrazinecarboxyimidamide] was approved for indications for chronic constipation and constipation-type irritable bowel syndrome in the United States and Europe, and defecation improvement activities by stimulation of 5-$HT_4$ receptors have been verified.

However, metoclopramide has a 5-$HT_4$ receptor agonistic action, while it also has a dopamine $D_2$ receptor antagonism contributing adverse effects which causes central depressant, which has been one of clinical problems. Additionally, the sale of cisapride was stopped due to its adverse effects to the heart, e.g., serious ventricular arrhythmia and QT extension as well as its central depressant action based on a dopamine $D_2$ receptor antagonism. Tegaserod has been temporarily withdrawn from the market of the United States due to its increased risk of serious ischemic cardiovascular adverse effects.

Since patients suffering from digestive system-indefinite complaint tend to be increased, development of excellent enterokinesis-promoting agents or improving agents for digestive tract function with less adverse effects is aspired in clinical practice.

It has been known that morpholine derivatives etc. with benzyl group etc. on nitrogen atom on 4-position among morpholine ring or 1,4-hexahydroxazepine ring compounds have selectively agonistic effects on 5-$HT_4$ receptors, and are useful as an enterokinesis-promoting agent or a digestive tract function-improving agent (see Patent Document 1).

Additionally, it has been known that N-carboxyalkylmorpholine derivatives have a prokinetic effect on digestive tract function and an antiemetic action and are useful as a therapeutic agent for digestive system disease (see Patent Document 2).

Further, it has been known that N-substituted morpholine derivatives etc. have enterokinesis -stimulating properties and accelerate the gastric emptying (see Patent Document 3).

However, a compound wherein a saturated nitrogen-containing heterocycle binds to nitrogen on 4-position in morpholine ring or 1,4-hexahydroxazepine ring via methylene group has not been reported.

Nonpatent Document 1: J. Pharmacol. Exp. Ther., (1990) 252, p 1378
Nonpatent Document 2: J. Pharmacol. Exp. Ther., (1991) 257, p 781
Patent Document 1: European Patent Application Publication No.: 243959
Patent Document 2: WO92/14705
Patent Document 3: WO96/37486

DISCLOSURE OF INVENTION

Problems to be Resolved by Invention

The problem to be resolved by the invention is to provide a serotonin 4 receptor agonist useful as an enterokinesis-promoting agent, etc.

Means of Solving Problems

According to extensive studies, the present inventors have found that benzamide derivatives wherein an amine moiety is morpholine ring or 1,4-hexahydroxazepine ring and a saturated nitrogen-containing heterocycle is substituted on 4-position of each ring via methylene chain show excellent agonist activities against 5-$HT_4$ receptors and are useful as an enterokinesis -promoting agent or a digestive tract function-improving agent with strong defecation-improving activities, and have achieved the present invention.

Specifically, the present invention is as follows.

[1] A compound of formula (1):

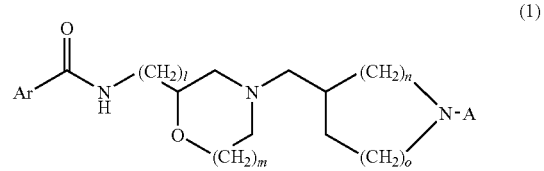

wherein Ar is a group of formula (Ar-1) or (Ar-2):

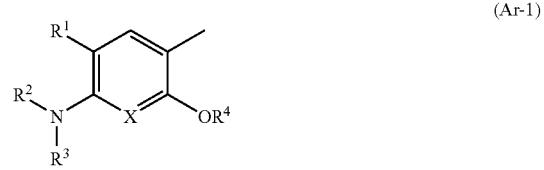

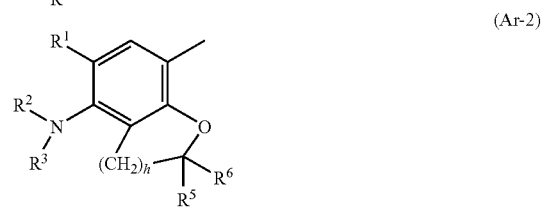

wherein $R^1$ is hydrogen or halogen, $R^2$ is hydrogen or alkyl, $R^3$ is hydrogen, alkyl or alkanoyl, $R^4$ is hydrogen, alkyl, alkenyl or alkynyl, X is nitrogen or CH, $R^5$ and $R^6$ are the same or different and each hydrogen or alkyl, and h is 1, 2 or 3;
l is 1, 2 or 3;
m is 1 or 2;
n is 0, 1 or 2;

o is an integer of 0 to 3, provided that n and o are not simultaneously 0;

A is a group selected from the group consisting of (1) to (6):
(1) hydrogen, cyano or formyl;
(2) optionally substituted alkyl, optionally substituted alkenyl or optionally substituted alkynyl;
(3) —$COR^7$, —$CSR^7$, —$COOR^7$, —$SO_2R^7$ or —CO—$COR^7$
wherein $R^7$ is optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted monocyclic or bicyclic nonaromatic unsaturated heterocyclyl in which the heterocyclyl is bonded via any carbon atoms on the heterocycle, or optionally substituted monocyclic or bicyclic saturated heterocyclyl in which the heterocyclyl is bonded via any carbon atoms on the heterocycle;
(4) —CO—$COOR^8$
wherein $R^8$ is alkyl;
(5) —$CONR^9$—$OR^{10}$
wherein $R^9$ and $R^{10}$ are the same or different and each hydrogen, alkyl, alkenyl or alkynyl; and
(6) —$CONR^{12}R^{13}$, —$CSNR^{12}R^{13}$ or —$SO_2NR^{12}R^{13}$
wherein $R^{12}$ is hydrogen or any one of groups in $R^7$, $R^{13}$ is hydrogen, alkyl, alkenyl or alkynyl; or both $R^{12}$ and $R^{13}$ may combine each other together with the adjacent nitrogen atom to form optionally substituted saturated or unsaturated monocyclic nitrogen-containing heterocycle containing 1 to 3 heteroatoms selected from 1 to 3 nitrogen, 1 oxygen or 1 sulfur;

provided that if alkyl, alkenyl or alkynyl in A or $R^7$ is substituted, then alkyl, alkenyl and alkynyl are optionally substituted by the same or different 1 to 5 substituents selected from the group consisting of (a) to (d):
(a) halogen, cyano, nitro, hydroxy, carboxy, amino, carbamoyl or trifluoromethyl;
(b) —$OR^{14}$, —$SR^{14}$, —$COR^{14}$, —$COOR^{14}$, —O—$COR^{14}$, —$NR^{15}$—$COR^{14}$, —$NR^{15}$—$COOR^{14}$, —$NR^{15}$—$SO_2R^{14}$, —$NR^{15}R^{16}$ or —$CONR^{15}R^{16}$
wherein $R^{14}$ is alkyl, alkenyl or alkynyl optionally substituted by the same or different 1 to 5 substituents selected from the group consisting of the following group:
(b') halogen, hydroxy, carboxy, amino, carbamoyl, —$OR^{17}$, —$COOR^{17}$, —$NR^{18}$—$COR^{17}$, —$NR^{18}$—$COOR^{17}$, —$NR^{18}$—$SO_2R^{17}$, —$NR^{18}R^{19}$ or —$CONR^{18}R^{19}$ in which $R^{17}$ is alkyl, alkenyl or alkynyl, $R^{18}$ is hydrogen or alkyl, $R^{19}$ is alkyl, alkenyl or alkynyl, or both $R^{18}$ and $R^{19}$ may combine each other together with the adjacent nitrogen atom to form optionally substituted saturated or unsaturated monocyclic nitrogen-containing heterocycle containing 1 to 3 heteroatoms selected from 1 to 3 nitrogen, 1 oxygen or 1 sulfur, $R^{15}$ is hydrogen, or alkyl, alkenyl or alkynyl optionally substituted by the same or different 1 to 5 substituents selected from the above (b'), $R^{16}$ is alkyl, alkenyl or alkynyl optionally substituted by the same or different 1 to 5 substituents selected from the above (b'), or both $R^{15}$ and $R^{16}$ may combine each other together with the adjacent nitrogen atom to form optionally substituted saturated or unsaturated monocyclic nitrogen-containing heterocycle containing 1 to 3 heteroatoms selected from 1 to 3 nitrogen, 1 oxygen or 1 sulfur;
(c) —$R^{20}$, —$OR^{20}$ or —$NR^{15}$—$COR^{20}$
wherein $R^{15}$ has the same meaning as defined above, $R^{20}$ is optionally substituted cycloalkyl, optionally substituted cycloalkenyl, optionally substituted monocyclic or bicyclic nonaromatic unsaturated heterocyclyl, optionally substituted monocyclic or bicyclic saturated heterocyclyl; and
(d) —$R^{21}$, —$OR^{21}$, —$COR^{21}$, —$SO_{21}$, —$SO_2R^{21}$ or —$NR^{15}$—$COR^{21}$
wherein $R^{15}$ has the same meaning as defined above, $R^{21}$ is optionally substituted aryl or optionally substituted heteroaryl;

provided that if cycloalkyl or cycloalkenyl is substituted, then cycloalkyl and cycloalkenyl are optionally substituted by the same or different 1 to 5 substituents selected from the following (e):
(e) halogen, hydroxy, alkyl, alkoxy or oxo;

provided that if any ring carbon atoms are substituted in the monocyclic or bicyclic nonaromatic unsaturated heterocyclyl, monocyclic or bicyclic saturated heterocyclyl, or saturated or unsaturated monocyclic nitrogen-containing heterocyclyl, then the carbon atoms are optionally substituted by the same or different 1 to 5 substituents selected from the above (e), provided that if any ring nitrogen atoms are substituted, then the nitrogen atoms are optionally substituted by the following (f):
(f) alkyl, alkanoyl, alkoxycarbonyl or alkylsulfonyl;

provided that if aryl or heteroaryl are substituted, then the aryl and heteroaryl are optionally substituted by the same or different 1 to 5 substituents selected from the group consisting of the following (g) to (i):
(g) halogen, cyano, nitro, hydroxy, carboxy, haloalkyl, haloalkoxy, amino, carbamoyl, —$(CH_2)_2$—O— or —O—$CH_2$—O—;
(h) —$R^{14}$, —$OR^{14}$, —$SR^{14}$, —$COR^{14}$, —$COOR^{14}$, —O—$COR^{14}$, —$NR^{15}$—$COR^{14}$, —$NR^{15}$—$COOR^{14}$, —$NR^{15}$—$SO_2R^{14}$, —$NR^{15}R^{16}$ or —$CONR^{15}R^{16}$
wherein $R^{14}$, $R^{15}$ and $R^{16}$ have the same meanings as defined above; and
(i) phenyl or phenoxy which is optionally substituted by 1 to 5 substituents selected from the group consisting of halogen, hydroxy, alkyl and alkoxy; or a pharmaceutically acceptable salt thereof.

[2] The compound of [1], wherein $R^1$ is chlorine, bromine or iodine, $R^4$ is alkyl, $R^5$ and $R^6$ are the same or different and each hydrogen or methyl, or a pharmaceutically acceptable salt thereof.

[3] The compound of [2], wherein $R^4$ is methyl, ethyl, propyl or isopropyl, or a pharmaceutically acceptable salt thereof.

[4] The compound of [1] to [3], wherein $R^2$ is hydrogen, $R^3$ is hydrogen or methyl, or a pharmaceutically acceptable salt thereof.

[5] The compound of [4], wherein $R^2$ and $R^3$ are hydrogen, or a pharmaceutically acceptable salt thereof.

[6] The compound of [1] to [5], wherein l is 1 or 2, m is 1 or 2, n is 1 or 2, o is 1 or 2, or a pharmaceutically acceptable salt thereof.

[7] The compound of [1], wherein $R^1$ is chlorine or bromine, $R^2$ and $R^3$ are hydrogen, $R^4$ is methyl or ethyl, $R^5$ and $R^6$ are hydrogen, h is 1, l is 1, m is 1, n is 2, o is 1, or a pharmaceutically acceptable salt thereof.

[8] The compound of [1] to [7], wherein A is
(1-1) hydrogen, cyano or formyl; or
(2-1) alkyl, or phenyl-substituted alkyl wherein phenyl is optionally substituted by the same or different 1 to 5 substituents selected from the group consisting of halogen, hydroxy, alkyl, alkoxy, alkanoyl, haloalkyl, haloalkoxy, amino and carboxy; or a pharmaceutically acceptable salt thereof.

[9] The compound of [1] to [7], wherein A is
(3-1) —$COR^{7a}$, —$COOR^{7a}$, —$SO_2R^{7a}$ or —CO—$COR^{7a}$ wherein $R^{7a}$ is optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted monocyclic or bicyclic nonaromatic unsaturated heterocyclyl, or optionally substituted monocyclic or bicyclic saturated heterocyclyl;

provided that if alkyl, alkenyl or alkynyl in $R^{7a}$ is substituted, then the alkyl, alkenyl and alkynyl are optionally substituted by 1 to 5 substituents selected from the group consisting of (a-1) to (d-1):

(a-1) halogen, cyano, hydroxy, carboxy, amino or carbamoyl;
(b-1) —$OR^{14a}$, —$COR^{14a}$, —$COOR^{14a}$, —O—$COR^{14a}$, —$NR^{15a}$—$COOR^{14a}$, —$NR^{15a}$—$COOR^{14a}$, —$NR^{15a}R^{16a}$ or —$CONR^{15a}R^{16a}$ wherein $R^{14a}$ is alkyl, $R^{15a}$ is hydrogen or alkyl, $R^{16a}$ is alkyl, or both $R^{15a}$ and $R^{16a}$ may combine each other together with the adjacent nitrogen atom to form saturated monocyclic nitrogen-containing heterocycle containing 1 to 3 heteroatoms selected from 1 to 3 nitrogen, 1 oxygen or 1 sulfur, and the nitrogen atom on the monocyclic nitrogen-containing heterocycle is optionally substituted by alkyl, alkanoyl or alkoxycarbonyl;

(c-1) cycloalkyl which is optionally substituted by the same or different 1 to 5 substituents selected from halogen, hydroxy, alkyl or alkoxy, monocyclic or bicyclic saturated heterocyclyl wherein the ring carbon atom is optionally substituted by the same or different 1 to 5 substituents selected from halogen, hydroxy, alkyl or alkoxy and the ring nitrogen atom is optionally substituted by alkyl, alkanoyl or alkoxycarbonyl; and (d-1) —$R^{21a}$ or —$NR^{15a}$—$COR^{21a}$ wherein $R^{15a}$ has the same meaning as defined above, $R^{21a}$ is aryl or heteroaryl, and the aryl and heteroaryl are optionally substituted by the same or different 1 to 5 substituents selected from halogen, hydroxy, carboxy, haloalkyl, haloalkoxy, amino, carbamoyl, cyano, —$R^{14a}$, —$OR^{14a}$, —$COR^{14a}$, —$NR^{15a}$—$COR^{14a}$ or —$NR^{15a}R^{16a}$ wherein $R^{14a}$, $R^{15a}$ and $R^{16a}$ have the same meanings as defined above;

provided that if cycloalkyl or cycloalkenyl in $R^{7a}$ is substituted, then cycloalkyl and cycloalkenyl are optionally substituted by the same or different 1 to 5 substituents selected from the following (e-1):

(e-1) halogen, hydroxy, alkyl or alkoxy;

provided that if any ring carbon atoms are substituted in optionally substituted monocyclic or bicyclic nonaromatic unsaturated heterocyclyl, and optionally substituted monocyclic or bicyclic saturated heterocyclyl in $R^{7a}$, then the carbon atoms are optionally substituted by the same or different 1 to 5 substituents selected from the above (e-1), and if any ring nitrogen atoms are substituted, then the nitrogen atoms are optionally substituted by the same or different 1 to 5 substituents selected from the following (f-1):

(f-1) alkyl, alkanoyl, alkoxycarbonyl or alkylsulfonyl;

provided that if aryl or heteroaryl in $R^{7a}$ is substituted, then the aryl and heteroaryl are optionally substituted by the same or different 1 to 5 substituents selected from the group consisting of the following groups:

(g-1) halogen, nitro, hydroxy, carboxy, amino, carbamoyl, haloalkyl, haloalkoxy or cyano;
(h-1) —$R^{14a}$, —$OR^{14a}$, —$COR^{14a}$, —$COOR^{14a}$, —O—$COR^{14a}$, —$NR^{15a}$—$COR^{14a}$, —$NR^{15a}$—$COOR^{14a}$ or —$NR^{15a}R^{16a}$ wherein $R^{14a}$, $R^{15a}$ and $R^{16a}$ have the same meanings as defined above; and (i-1) phenyl or phenoxy which is optionally substituted by 1 to 5 substituents selected from the group consisting of halogen, hydroxy, alkyl and alkoxy; or a pharmaceutically acceptable salt thereof.

[10] The compound of [9], wherein A is (3-2) —$SO_2R^{7b}$ wherein $R^{7b}$ is alkyl, alkyl substituted by optionally substituted phenyl, or optionally substituted phenyl, provided that if phenyl is substituted, then the phenyl is optionally substituted by the same or different 1 to 5 substituents selected from the group consisting of halogen, hydroxy, carboxy, haloalkyl, haloalkoxy, amino, carbamoyl, —$R^{14b}$, —$OR^{14b}$, —$COR^{14b}$, —$COOR^{14b}$ and —O—$COR^{14b}$ wherein $R^{14b}$ is alkyl; or a pharmaceutically acceptable salt thereof.

[11] The compound of [10], wherein $R^{7b}$ is $C_{1-3}$ alkyl, or a pharmaceutically acceptable salt thereof.

[12] The compound of [9], wherein A is (3-3) —$COR^{7c}$ or —CO—$COR^{7c}$ wherein $R^{7c}$ is optionally substituted alkyl or optionally substituted alkenyl;

provided that if alkyl or alkenyl in $R^{7c}$ is substituted, then the alkyl and alkenyl are optionally substituted by 1 to 5 substituents selected from the group consisting of (a-2) to (d-2):

(a-2) hydroxy, halogen, carbamoyl or cyano;
(b-2) —$OR^{14c}$, —$COR^{14c}$, —$COOR^{14c}$, —O—$COR^{14c}$, —$NR^{15c}$—$COR^{14c}$, —$NR^{15c}R^{16c}$ or —$CONR^{15c}R^{16c}$ wherein $R^{14c}$ and $R^{16c}$ are the same or different alkyl and $R^{15c}$ is hydrogen or alkyl;

(c-2) cycloalkyl, or monocyclic or bicyclic saturated heterocyclyl wherein the nitrogen atom on the monocyclic or bicyclic saturated heterocyclyl is optionally substituted by alkyl, alkanoyl or alkoxycarbonyl; and (d-2) —$R^{21c}$ or —$NR^{15c}$—$COR^{21c}$ wherein $R^{15c}$ has the same meaning as defined above, $R^{21c}$ is aryl or heteroaryl, and the aryl and heteroaryl are optionally substituted by the same or different 1 to 5 substituents selected from the group consisting of halogen, hydroxy, carboxy, haloalkyl, haloalkoxy, amino, carbamoyl, cyano, —$R^{14c}$, —$OR^{14c}$ and —$COR^{14c}$ wherein $R^{14c}$ has the same meaning as defined above; or a pharmaceutically acceptable salt thereof.

[13] The compound of [12], wherein $R^{7c}$ is $C_{1-3}$ alkyl optionally substituted by a group selected from the group consisting of the following (a-3) and (b-3):

(a-3) hydroxy, carbamoyl or cyano; and
(b-3) —$OR^{14d}$, —$COR^{14d}$, —$COOR^{14d}$, —O—$COR^{14d}$, —$NR^{15d}$—$COR^{14d}$, —$NR^{15d}R^{16d}$ or —$CONR^{15d}R^{16d}$ wherein $R^{14d}$ and $R^{16d}$ are the same or different $C_{1-3}$ alkyl, and $R^{15d}$ is hydrogen or $C_{1-3}$ alkyl; or $C_{2-3}$ alkenyl optionally substituted by a group selected from the group consisting of the above (a-3) and (b-3), or a pharmaceutically acceptable salt thereof.

[14] The compound of [9], wherein A is (3-4) —$COR^{7d}$ wherein $R^{7d}$ is optionally substituted cycloalkyl, optionally substituted cycloalkenyl, optionally substituted monocyclic or bicyclic nonaromatic unsaturated heterocyclyl, or optionally substituted monocyclic saturated heterocyclyl;

provided that if any ring carbon atoms are substituted, then the carbon atoms are optionally substituted by the same or different 1 to 5 substituents selected from halogen, hydroxy, alkyl or alkoxy, and if the ring nitrogen atoms are substituted, then the nitrogen atoms are optionally substituted by alkyl, alkanoyl, alkoxycarbonyl or alkylsulfonyl; or a pharmaceutically acceptable salt thereof.

[15] The compound of [9], wherein A is
(3-5) —COR$^{7e}$
wherein R$^{7e}$ is optionally substituted aryl or optionally substituted heteroaryl;
provided that if aryl or heteroaryl is substituted, then the aryl and heteroaryl are optionally substituted by the same or different 1 to 5 substituents selected from the group consisting of the following (g-2) to (i-2):
(g-2) halogen, amino, carbamoyl or cyano;
(h-2) —R$^{14e}$, —OR$^{14e}$, —O—COR$^{14e}$, —NR$^{15e}$—COR$^{14e}$, —NR$^{15e}$—COOR$^{14e}$ or —NR$^{15e}$R$^{16e}$ wherein R$^{14e}$ and R$^{16e}$ are the same or different and each alkyl, R$^{15e}$ is hydrogen or alkyl; and
(i-2) phenyl or phenoxy; or a pharmaceutically acceptable salt thereof.
[16] The compound of [9], wherein A is
(3-6) —COOR$^{7f}$
wherein R$^{7f}$ is alkyl, alkenyl or optionally substituted phenyl;
provided that if phenyl is substituted, then the phenyl is optionally substituted by the same or different 1 to 5 substituents selected from the group consisting of halogen, nitro, hydroxy, haloalkyl, haloalkoxy, —R$^{14f}$, and —OR$^{14f}$ and —COR$^{14f}$ wherein R$^{14f}$ is alkyl; or a pharmaceutically acceptable salt thereof.
[17] The compound of [16], wherein R$^{7f}$ is C$_{1-3}$ alkyl or C$_{2-3}$ alkenyl, or a pharmaceutically acceptable salt thereof.
[18] The compound of [1] to [7], wherein A is
(6-1)    —CONR$^{12a}$R$^{13a}$,    —CSNR$^{12a}$R$^{13a}$    or —SO$_2$NR$^{12a}$R$^{13a}$
wherein R$^{12a}$ is hydrogen, C$_{1-3}$ alkyl, C$_{2-3}$ alkenyl, C$_{1-3}$ alkyl substituted by C$_{2-3}$ alkoxycarbonyl, C$_{1-3}$ alkyl substituted by optionally substituted phenyl, or optionally substituted phenyl, provided that if phenyl is substituted, then the phenyl is optionally substituted by the same or different 1 to 5 substituents selected from the group consisting of halogen, nitro, hydroxy, carboxy, haloalkyl, haloalkoxy, amino, carbamoyl, —R$^{14a}$, —OR$^{14a}$, —COR$^{14a}$, —COOR$^{14a}$ and —O—COR$^{14a}$ wherein R$^{14a}$ is alkyl;
R$^{13a}$ is hydrogen or alkyl, or both R$^{12a}$ and R$^{13a}$ may combine each other together with the adjacent nitrogen atom to form optionally substituted saturated or unsaturated 4- to 6-membered monocyclic nitrogen-containing heterocycle containing 1 to 3 heteroatoms selected from the group consisting of 1 to 3 nitrogen, 1 oxygen and 1 sulfur, and the nitrogen atom on the monocyclic nitrogen-containing heterocycle is optionally substituted by alkyl, alkanoyl or alkoxycarbonyl; or a pharmaceutically acceptable salt thereof.
[19] The compound of [18], wherein R$^{12a}$ and R$^{13a}$ are the same or different and each C$_{1-3}$ alkyl;
R$^{12a}$ is optionally substituted phenyl wherein phenyl is optionally substituted by 1 to 2 halogen, hydroxy, carboxy, haloalkyl, amino, carbamoyl, —R$^{14a}$, —OR$^{14a}$, —COR$^{14a}$, —COOR$^{14a}$ or —O—COR$^{14a}$ wherein R$^{14a}$ is alkyl, and R$^{13a}$ is hydrogen; or
both R$^{12a}$ and R$^{13a}$ combine each other together with the adjacent nitrogen atom to form pyrrolidinyl, piperidinyl, morpholinyl or imidazolyl; or a pharmaceutically acceptable salt thereof.
[20] The compound of [1] to [7], wherein A is
(5-1) —CONR$^{9a}$—OR$^{10a}$
wherein R$^{9a}$ and R$^{10a}$ are the same or different and each alkyl, or a pharmaceutically acceptable salt thereof.
[21] The compound of [1], selected from the group consisting of the following compounds:
4-amino-N-[{4-[(1-(1-azetidinecarbonyl)-4-piperidinyl)methyl)]-2-morpholinyl}methyl]-5-chloro-2-ethoxybenzamide;
4-amino-5-chloro-2-methoxy-N-[{4-[(1-pyrrolidinecarbonyl-4-piperidinyl)methyl]-2-morpholinyl}-methyl]benzamide;
4-amino-5-chloro-2-ethoxy-N-[{4-[(1-(1-pyrrolidinecarbonyl)-4-piperidinyl)methyl]-2-morpholinyl}-methyl]benzamide;
4-amino-5-chloro-N-[{4-[(1-dimethylcarbamoyl-4-piperidinyl)methyl]-2-morpholinyl}methyl]-2-methoxybenzamide;
4-amino-5-chloro-N-[{4-[(1-dimethylcarbamoyl-4-piperidinyl)methyl]-2-morpholinyl}methyl]-2-ethoxybenzamide;
4-amino-5-chloro-N-[{4-[(1-dimethylthiocarbamoyl-4-piperidinyl)methyl]-2-morpholinyl}methyl]-2-ethoxybenzamide;
4-amino-5-chloro-N-[{4-[(1-dimethylsulfamoyl-4-piperidinyl)methyl]-2-morpholinyl}methyl]-2-methoxybenzamide;
4-amino-5-chloro-N-[{4-[(1-dimethylsulfamoyl-4-piperidinyl)methyl]-2-morpholinyl}methyl]-2-ethoxybenzamide;
4-amino-5-chloro-N-[{4-[(1-dimethylcarbamoyl-4-piperidinyl)methyl]-2-morpholinyl}methyl]-2-isopropoxybenzamide;
4-amino-5-chloro-N-[{4-[(1-diethylcarbarnoyl-4-piperidinyl)methyl]-2-morpholinyl}methyl]-2-ethoxybenzamide;
4-amino-5-chloro-N-[{4-[(1-diisopropylcarbamoyl-4-piperidinyl)methyl]-2-morpholinyl}methyl]-2-methoxybenzamide;
6-amino-5-chloro-N-[{4-[(1-dimethylcarbamoyl-4-piperidinyl)methyl]-2-morpholinyl}methyl]-2-methoxypyridine-3-carboxamide;
N-[{4-[(1-allylmethylcarbamoyl-4-piperidinyl)methyl]-2-morpholinyl}methyl]-4-amino-5-chloro-2-ethoxybenzamide;
4-amino-5-chloro-N-[{4-[(1-(1-pyrrolidinecarbonyl)-4-piperidinyl)methyl]-2-morpholinyl}methyl]-2,3-dihydrobenzo[b]furan-7-carboxamide;
4-amino-5-chloro-N-[{4-[(1-dimethylcarbamoyl-4-piperidinyl)methyl]-2-morpholinyl}methyl]-2,3-dihydrobenzo[b]furan-7-carboxamide;
4-amino-5-chloro-2-ethoxy-N-[{4-[(1-methylcarbamoyl-4-piperidinyl)methyl]-2-morpholinyl}methyl]-benzamide;
4-amino-5-chloro-2-ethoxy-N-[{4-[(1-ethylcarbamoyl-4-piperidinyl)methyl]-2-morpholinyl}methyl]-benzamide;
4-amino-5-chloro-2-methoxy-N-[{4-[(1-phenylcarbamoyl-4-piperidinyl)methyl]-2-morpholinyl}-methyl]benzamide;
4-amino-5-chloro-2-methoxy-N-[{4-[(1-(2-methoxyphenyl)carbamoyl-4-piperidinyl)methyl]-2-morpholinyl}methyl]benzamide;
4-amino-5-chloro-2-methoxy-N-[{4-[(1-(3-trifluoromethylphenyl)carbamoyl-4-piperidinyl)methyl]-2-morpholinyl}methyl]benzamide;
N-[{4-[(1-(3-acetylphenyl)carbamoyl-4-piperidinyl)methyl]-2-morpholinyl}methyl]-4-amino-5-chloro-2-methoxybenzamide;
4-amino-5-chloro-N-[{4-[(1-(3,5-dimethylphenyl)carbamoyl-4-piperidinyl)methyl]-2-morpholinyl}-methyl]-2-methoxybenzamide;
4-amino-5-chloro-N-[{4-[(1-(3,4-dichlorophenyl)carbamoyl-4-piperidinyl)methyl]-2-morpholinyl}-methyl]-2-methoxybenzamide;
4-amino-N-[{4-[(1-benzylcarbamoyl-4-piperidinyl)methyl]-2-morpholinyl}methyl]-5-chloro-2-methoxybenzamide;
4-amino-5-chloro-2-methoxy-N-[{4-[(1-(2-methylbenzyl)carbamoyl-4-piperidinyl)methyl]-2-morpholinyl}methyl]benzamide;

4-amino-5-chloro-2-methoxy-N-[{4-[(1-(4-methoxybenzyl)carbamoyl-4-piperidinyl)methyl]-2-morpholinyl}methyl]benzamide;

4-amino-5-chloro-N-[{4-[(1-(2,4-dichlorobenzyl)carbamoyl-4-piperidinyl)methyl]-2-morpholinyl}-methyl]-2-methoxybenzamide;

4-amino-5-chloro-2-methoxy-N-[{4-[(1-(2-phenethyl)carbamoyl-4-piperidinyl)methyl]-2-morpholinyl}methyl]benzamide;

4-amino-5-chloro-2-ethoxy-N-[{4-[(1-methoxycarbonyl-4-piperidinyl)methyl]-2-morpholinyl}methyl]-benzamide;

4-amino-5-chloro-N-[{4-[(1-methanesulfonyl-4-piperidinyl)methyl]-2-morpholinyl}methyl]-2-methoxybenzamide;

amino-5-chloro-2-ethoxy-N-[{4-[(1-methanesulfonyl-4-piperidinyl)methyl]-2-morpholinyl}methyl]-benzamide;

4-amino-5-chloro-2-methoxy-N-[{4-[(1-(1-propoxycarbonyl)-4-piperidinyl)methyl]-2-morpholinyl}-methyl]benzamide;

N-[{4-[(1-allyloxycarbonyl-4-piperidinyl)methyl]-2-morpholinyl}methyl]-4-amino-5-chloro-2-methoxybenzamide;

4-amino-5-chloro-N-[{4-[(1-isobutoxycarbonyl-4-piperidinyl)methyl]-2-morpholinyl}methyl]-2-methoxybenzamide;

4-amino-5-chloro-2-methoxy-N-[{4-[(1-phenoxycarbonyl-4-piperidinyl)methyl]-2-morpholinyl}-methyl]benzamide;

4-amino-5-chloro-2-methoxy-N-[{4-[(1-(2-methoxyphenoxycarbonyl)-4-piperidinyl)methyl]-2-morpholinyl}methyl]benzamide;

N-[{4-[(1-acetoxyacetyl-4-piperidinyl)methyl]-2-morpholinyl}methyl]-4-amino-5-chloro-2-ethoxybenzamide;

4-amino-5-chloro-N-[{4-[(1-(1-cyclopentenecarbonyl)-4-piperidinyl)methyl]-2-morpholinyl}methyl]-2-ethoxybenzamide;

4-amino-5-chloro-N-[{4-[(1-(2-cyclopropylvinylcarbonyl)-4-piperidinyl)methyl]-2-morpholinyl}-methyl]-2-ethoxybenzamide;

4-amino-5-chloro-2-ethoxy-N-[{4-[(1-[2-(furan-2-yl)vinylcarbonyl]-4-piperidinyl)methyl]-2-morpholinyl}methyl]benzamide;

4-amino-5-chloro-2-ethoxy-N-[{4-[(1-[2-(thiophen-2-yl)vinylcarbonyl]-4-piperidinyl)methyl]-2-morpholinyl}methyl]benzamide;

4-amino-N-[{4-[(1-(3-butenecarbonyl)-4-piperidinyl)methyl]-2-morpholinyl}methyl]-5-chloro-2ethoxybenzamide;

4-amino-5-chloro-2-ethoxy-N-[{4-[(1-(5-hexenecarbonyl)-4-piperidinyl)methyl]-2-morpholinyl}-methyl]benzamide;

4-amino-N-[{4-[(1-(1,3-butadienecarbonyl)-4-piperidinyl)methyl]-2-morpholinyl}methyl]-5-chloro-2-ethoxybenzamide;

4-amino-5-chloro-2-ethoxy-N-[{4-[(1-(1,5-hexadienecarbonyl)-4-piperidinyl)methyl]-2-morpholinyl}-methyl]benzamide;

4-amino-N-[{4-[(1-[1-(1-propyne)carbonyl]-4-piperidinyl)methyl]-2-morpholinyl}methyl]-5-chloro-2-ethoxybenzamide;

4-amino-5-chloro-N-[{4-[(1-methoxycarbonyl-4-piperidinyl)methyl]-2-morpholinyl}methyl]-2,3-dihydrobenzo[b]furan-7-carboxamide;

N-[{4-[(1-acetyl-4-piperidinyl)methyl]-2-morpholinyl}methyl]-4-amino-5-chloro-2,3-dihydrobenzo[b]furan-7-carboxamide;

4-amino-5-chloro-N-[{4-[(1-methanesulfonyl-4-piperidinyl)methyl]-2-morpholinyl}methyl]-2,3-dihydrobenzo[b]furan-7-carboxamide;

4-amino-N-[{4-[(1-benzoyl-4-piperidinyl)methyl]-2-morpholinyl}methyl]-5-chloro-2-ethoxybenzamide;

4-amino-5-chloro-N-[{4-[(1-(3-fluorobenzoyl)-4-piperidinyl)methyl]-2-morpholinyl}methyl]-2-methoxybenzamide;

4-amino-5-chloro-2-ethoxy-N-[{4-[(1-(3-fluorobenzoyl)-4-piperidinyl)methyl]-2-morpholinyl}-methyl]benzamide;

4-amino-5-chloro-N-[{4-[(1-(4-chlorobenzoyl)-4-piperidinyl)methyl]-2-morpholinyl}methyl]-2-methoxybenzamide;

4-amino-5-chloro-N-[{4-[(1-(4-chlorobenzoyl)-4-piperidinyl)methyl]-2-morpholinyl}methyl]-2-ethoxybenzamide;

4-amino-N-[{4-[(1-(3-bromobenzoyl)-4-piperidinyl)methyl]-2-morpholinyl}methyl]-5-chloro-2-methoxybenzamide;

4-amino-5-chloro-2-methoxy-N-[{4-[(1-(2-methylbenzoyl)-4-piperidinyl)methyl]-2-morpholinyl}-methyl]benzamide;

4-amino-5-chloro-2-methoxy-N-[{4-[(1-(3-methylbenzoyl)-4-piperidinyl)methyl]-2-morpholinyl}-methyl]benzamide;

4-amino-5-chloro-2-methoxy-N-[{4-[(1-(4-methylbenzoyl)-4-piperidinyl)methyl]-2-morpholinyl}-methyl]benzamide;

4-amino-5-chloro-2-ethoxy-N-[{4-[(1-(4-methylbenzoyl)-4-piperidinyl)methyl]-2-morpholinyl}-methyl]benzamide;

4-amino-5-chloro-N-[{4-[(1-(4-ethylbenzoyl)-4-piperidinyl)methyl]-2-morpholinyl}methyl]-2-methoxybenzamide;

4-amino-N-[{4-[(1-(tert-butylbenzoyl)-4-piperidinyl)methyl]-2-morpholinyl}methyl]-5-chloro-2-methoxybenzamide;

4-amino-5-chloro-N-[{4-[(1-(3-hydroxybenzoyl)-4-piperidinyl)methyl]-2-morpholinyl}methyl]-2-methoxybenzamide;

4-amino-5-chloro-N-[{4-[(1-(4-hydroxybenzoyl)-4-piperidinyl)methyl]-2-morpholinyl}methyl]-2-methoxybenzamide;

N-[{4-[(1-(2-acetoxybenzoyl)-4-piperidinyl)methyl]-2-morpholinyl}methyl]-4-amino-5-chloro-2-methoxybenzamide;

N-[{4-[(1-(2-acetoxybenoyl)-4-piperidinyl)methyl]-2-morpholinyl}methyl]-4-amino-5-chloro-2-ethoxybenzamide;

N-[{4-[(1-(3-acetoxybenzoyl)-4-piperidinyl)methyl]-2-morpholinyl}methyl]-4-amino-5-chloro-2-methoxybenzamide;

N-[{4-[(1-(4-acetoxybenzoyl)-4-piperidinyl)methyl]-2-morpholinyl}methyl]-4-amino-5-methoxybenzamide;

4-amino-5-chloro-2-methoxy-N-[{4-[(1-(3-methoxybenzoyl)-4-piperidinyl)methyl]-2-morpholinyl}-methyl]benzamide;

4-amino-5-chloro-2-methoxy-N-[{4-[(1-(4-methoxybenzoyl)-4-piperidinyl)methyl]-2-morpholinyl}-methyl]benzamide;

4-amino-5-chloro-2-ethoxy-N-[{4-[(1-(4-methoxybenzoyl)-4-piperidinyl)methyl]-2-morpholinyl}-methyl]benzamide;

4-amino-5-chloro-2-methoxy-N-[{4-[(1-(2-phenoxybenzoyl)-4-piperidinyl)methyl]-2-morpholinyl}-methyl]benzamide;

4-amino-5-chloro-N-[{4-[(1-(3-dimethylaminobenzoyl)-4-piperidinyl)methyl]-2-morpholinyl}methyl]-2-methoxybenzamide;

4-amino-5-chloro--N-[{4-[(1-(4-dimethylaminobenzoyl)-4-piperidinyl)methyl]-2-morpholinyl}methyl]-2-methoxybenzamide;

4-amino-5-chloro-2-methoxy-N-[{4-[(1-(4-methoxycarbonylbenzoyl)-4-piperidinyl)methyl]-2-morpholinyl}methyl]benzamide;

4-amino-5-chloro-2-methoxy-N-[{4-[(1-(4-phenylbenzoyl)-4-piperidinyl)methyl]-2-morpholinyl}-methyl]benzamide;

4-amino-N-[{4-[1(-(4-amino-3-chlorophenylbenzoyl)-4-piperidinyl)methyl]-2-morpholinyl}methyl]-5chloro-2-methoxybenzamide;

4-amino-5-chloro-N-[{4-[(1-(2-furancarbonyl)-4-piperidinyl)methyl]-2-morpholinyl}methyl]-2-methoxybenzamide;

4-amino-5-chloro-N-[{4-[(1-(1-imidazolecarbonyl)-4-piperidinyl)methyl]-2-morpholinyl}methyl]-2-methoxybenzamide;

4-amino-5-chloro-N-[{4-[(1-[(1,2-dihydrobenzothran-7-yl)carbonyl]-4-piperidinyl)methyl]-2-morpholinyl}methyl]-2-methoxybenzamide;

4-amino-5-chloro-2-methoxy-N-[{4-[(1-[(5-methylthiophen-2-yl)carbonyl]-4-piperidinyl)methyl]-2-morpholinyl}methyl]benzamide;

4-amino-5-chloro-2-methoxy-N-[{4-[(1-[(S)-2-tetrahydrofurylcarbonyl]-4-piperidinyl)methyl]-2-morpholinyl}methyl]benzamide;

4-amino-5-chloro-2-methoxy-N-[{4-[(1-methoxyacetyl-4-piperidinyl)methyl]-2-morpholinyl}methyl]-benzamide;

4-amino-5-chloro-2-ethoxy-N-[{4-[(1-methoxyacetyl-4-piperidinyl)methyl]-2-morpholinyl}methyl]-benzamide;

4-amino-5-chloro-N-[{4-[(1-hydroxyacetyl-4-piperidinyl)methyl]-2-morpholinyl}methyl]-2-methoxybenzamide;

4-amino-5-chloro-2-ethoxy-N-[{4-[(1-hydroxyacetyl-4-piperidinyl)methyl]-2-morpholinyl}methyl]-benzamide;

4-amino-5-chloro-N-[{4-[(1-hydroxyacetyl-4-piperidinyl)methyl]-2-morpholinyl}methyl]-2,3-dihydrobenzo[b]furan-7-carboxamide;

4-amino-5-chloro-2-methoxy-N-[{4-[(1-(4-piperidinylmethylcarbonyl)-4-piperidinyl)methyl]-2-morpholinyl}methyl]benzamide;

N-[{4-[(1-acetyl-4-piperidinyl)methyl]-2-morpholinyl}methyl]-4-amino-5-chloro-2-methoxybenzamide;

4-amino-N-[{4-[(1-benzoylaminoacetyl-4-piperidinyl)methyl]-2-morpholinyl}methyl]-5-chloro-2-methoxybenzamide;

4-amino-5-chloro-N-[{4-[(1-cyanoacetyl-4-piperidinyl)methyl]-2-morpholinyl}methyl]-2-methoxybenzamide;

4-amino-5-chloro-N-{[4-{[1-(3-methoxypropionyl)-4-piperidinyl]methyl}-2-morpholinyl]methyl}-2-methoxybenzamide;

4-amino-5-chloro-N-{[4-{[1-((S)-2-methoxypropionyl)-4-piperidinyl]methyl}-2-morpholinyl]methyl}-2-methoxybenzamide;

4-amino-5-chloro-2-methoxy-N-{[4-{[1-(3-tetrahydrofurylcarbonyl)-4-piperidinyl]methyl}-2-morpholinyl]methyl}benzamide;

4-amino-5-chloro-N-{[4-{[1-(1,2-dioxopropyl)-4-piperidinyl]methyl}-2-morpholinyl]methyl}-2-methoxybenzamide;

4-amino-5-chloro-2-methoxy-N-{[4-{[1-(4-oxazolylcarbonyl)-4-piperidinyl]methyl}-2-morpholinyl]methyl}benzamide;

4-amino-5-chloro-2-methoxy-N-{[4-{[1-(3-triazolylcarbonyl)-4-piperidinyl]methyl}-2-morpholinyl]methyl}benzamide;

4-amino-5-chloro-N-{[4-{[1-(4-cyanobenzoyl)-4-piperidinyl]methyl}-2-morpholinyl]methyl}-2-methoxybenzamide;

N-[{4-[(1-acetyl-4-piperidinyl)methyl]-2-morpholinyl}methyl]-4-amino-5-chloro-2,3-dihydrobenzo[b]furan-7-carboxamide;

4-amino-5-chloro-N-{[4-{[1-(3-tetrahydrofurylcarbonyl)-4-piperidinyl]methyl}-2-morpholinyl]-methyl}-2,3-dihydrobenzo[b]furan-7-carboxamide; and 4-amino-5-chloro-N-[{(4-[(1-hydroxyacetyl-4-piperidinyl)methyl]-2-morpholinyl}methyl]-2,3-dihydrobenzo[b]furan-7-carboxamide; or a pharmaceutically acceptable salt thereof.

[22] The compound of [21], wherein a carbon atom on 2-position of morpholinyl is in S-configuration.

[23] A pharmaceutical composition, comprising the compound of [1] to [22] or a pharmaceutically acceptable salt thereof.

[24] A serotonin 4 receptor agonist, comprising as an active ingredient the compound of [1] to [22] or a pharmaceutically acceptable salt thereof.

[25] An enterokinesis-promoting agent or digestive tract function-improving agent, comprising as an active ingredient the compound of [1] to [22] or a pharmaceutically acceptable salt thereof.

ADVANTAGEOUS EFFECT OF INVENTION

The present invention is allowed to provide novel amide derivatives having an agonistic activity against a serotonin 4 receptor which are useful as enterokinesis-promoting agents or digestive tract function-improving agents with defecation accelerating activities etc., and pharmaceutical compositions comprising the same.

BEST MODE FOR CARRYING OUT INVENTION

The terms used herein are set forth as below.

The "halogen" includes fluorine, chlorine, bromine or iodine.

The "alkyl" includes straight- or branched-chain $C_{1-10}$ alkyl, specifically methyl, ethyl, propyl, isopropyl, butyl, isobutyl, sec-butyl, tert-butyl, pentyl and hexyl, etc.

The "alkenyl" includes straight- or branched-chain $C_{2-10}$ alkenyl, which preferably includes, but not be limited to, alkenyl containing 1 to 2 double bonds, specifically ethenyl, 1-propenyl, 1-methylvinyl, 2-propenyl, 1-butenyl, 2-butenyl, 3-butenyl, 2-methyl -1-propenyl, 2-methyl-2-propenyl, 1-pentenyl, 2-pentenyl, 3-pentenyl, 4-pentenyl, 2-methyl-1-butenyl, 2-methyl-2-butenyl, 2-methyl-3-butenyl, 1-hexenyl, 2-hexenyl, 3-hexenyl, 4-hexenyl, 5-hexenyl, 2-methyl-1-pentenyl, 2-propyl-2-propenyl, 1-ethyl-2-methyl-2-propenyl, 1-methyl-3-methyl-3-butenyl, 4-methyl-4-pentenyl, 1,3-butadienyl, 1,5-hexadienyl, etc.

The "alkynyl" includes straight- or branched-chain $C_{2-10}$ alkynyl, which preferably includes, but not be limited to, alkynyl containing 1 to 2 triple bonds, more preferably 1 triple bond, specifically ethynyl, 1-propynyl, 2-propynyl, 1-butynyl, 1-methyl-2-propynyl, 3-butynyl, 2-butynyl, 1-pentynyl, 1-ethyl-2-propynyl, 4-pentynyl, 3-pentynyl, 2-pentynyl, 1-methyl-2-butynyl, 1-hexynyl, 2-hexynyl, 3-hexynyl, 4-hexynyl, 5-hexynyl, etc.

The "alkoxy" includes straight- or branched-chain $C_{1-10}$ alkoxy, specifically methoxy, ethoxy, propoxy, isopropoxy, butoxy, isobutoxy, sec-butoxy, tert-butoxy, pentyloxy and hexyloxy, etc.

The "alkanoyl" includes straight- or branched-chain $C_{2-10}$ alkanoyl, specifically acetyl, propanoyl, butanoyl, 2-methylpropanoyl, pentanoyl, 3-methylbutanoyl, 2-methylbutanoyl, hexanoyl, etc.

The "alkoxycarbonyl" includes straight- or branched-chain $C_{2-10}$ alkoxycarbonyl, specifically methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl, etc.

The "alkylsulfonyl" includes straight- or branched-chain $C_{1-10}$ alkylsulfonyl, specifically methylsulfonyl, ethylsulfonyl, propylsulfonyl, isopropylsulfonyl, butylsulfonyl, isobutylsulfonyl, sec-butylsulfonyl, tert-butylsulfonyl, pentylsulfonyl and hexylsulfonyl, etc.

The "haloalkyl" includes $C_{1-3}$ haloalkyl substituted by the same or different 1 to 5 halogen atoms, specifically fluoromethyl, difluoromethyl, trifluoromethyl, pentafluoroethyl, 2-fluoroethyl, 2,2-difluoroethyl, etc.

The "haloalkoxy" includes $C_{1-3}$ haloalkoxy substituted by the same or different 1 to 5 halogen atoms, specifically fluoromethoxy, difluoromethoxy, trifluoromethoxy, pentafluoroethoxy, 2-fluoroethoxy, 2,2-difluoroethoxy, etc.

The "cycloalkyl" includes 3 to 7-membered cycloalkyl, specifically cyclopropyl, cyclobutyl, cyclopentyl, cyclohexyl, cycloheptyl, etc.

The "cycloalkenyl" includes 5 to 7-membered cycloalkenyl, specifically 1-cyclopentenyl, 3-cyclopentenyl, 4-cyclopentenyl, 1-cyclohexenyl, 3-cyclohexenyl, 4-cyclohexenyl, 1-cycloheptenyl, 3-cycloheptenyl, 4-cycloheptenyl, 5-cycloheptenyl, etc.

The "aryl" includes 6 to 10-membered monocyclic or bicyclic aryl, specifically phenyl, 1-naphthyl, 2-naphthyl, etc.

The "heteroaryl" includes 5 to 10-membered monocyclic or bicyclic heteroaryl containing 1 to 4 heteroatoms selected from 1 to 4 nitrogen atoms, 1 oxygen atom or 1 sulfur atom. Specifically, the monocyclic heteroaryl includes pyrrolyl, imidazolyl, triazolyl, tetrazolyl, furyl, thienyl, oxazolyl, thiazolyl, pyridyl, pyrimidinyl, pyrazinyl, pyridazinyl, triazinyl, etc. The bicyclic heteroaryl includes indolyl, benzofuryl, benzothienyl, quinolinyl, benzoisoxazolyl, etc. The heteroaryl may be bonded on any carbon or nitrogen atoms so as to be chemically stable without a limitation.

The "monocyclic or bicyclic nonaromatic unsaturated heterocyclyl" includes 5 to 10-membered monocyclic or bicyclic nonaromatic unsaturated heterocyclyl containing 1 to 4 heteroatoms selected from 1 to 4 nitrogen atoms, 1 oxygen atom or 1 sulfur atom.

The monocyclic nonaromatic unsaturated heterocyclyl includes 5-membered nonaromatic unsaturated heterocyclyl containing 1 double bond, or 6 or 7-membered one containing 1 or 2 double bonds, specifically pyrrolinyl or 2,5-dihydrofuryl, etc.

The bicyclic nonaromatic unsaturated heterocyclyl includes 8 to 10-membered nonaromatic unsaturated heterocyclyl wherein 1 or multiple double bonds of bicyclic heteroaryl are replaced by a single bond, specifically 2,3-dihydrobenzofuryl, 2,3-dihydrobenzothienyl, etc.

The nonaromatic unsaturated heterocyclyl may be bonded on any carbon or nitrogen atoms so as to be chemically stable without a limitation.

The "monocyclic or bicyclic saturated heterocyclyl" includes 5 to 10-membered monocyclic or bicyclic saturated heterocyclyl containing 1 to 4 heteroatoms selected from 1 to 4 nitrogen atoms, 1 oxygen atom or 1 sulfur atom. The monocyclic saturated heterocyclyl includes 4 to 7-membered saturated heterocyclyl, specifically azetidinyl, pyrrolidinyl, tetrahydrofuryl, tetrahydrothienyl, piperazinyl, piperidinyl, morpholinyl, thiomorpholinyl, tetrahydropyranyl, hexahydroazepinyl, 1,4-hexahydroxazepinyl and 1,4-hexahydrodiazepinyl, etc. The bicyclic saturated heterocyclyl includes 8 to 10-membered saturated heterocyclyl, specifically quinuclidinyl, etc.

Any carbon atoms on the saturated heterocyclyl, may be optionally substituted by oxo, and the oxo-substituted saturated heterocyclyl, specifically, includes 2-oxopyrrolidinyl, 2-oxotetrahydrofuryl, etc.

The saturated heterocyclyl may be bonded on any carbon or nitrogen atoms so as to be chemically stable without a limitation.

The "saturated or unsaturated monocyclic nitrogen-containing heterocyclyl" which $R^{12}$ and $R^{13}$, $R^{15}$ and $R^{16}$, $R^{18}$ and $R^{19}$, $R^{12a}$ and $R^{13a}$, and $R^{15a}$ and $R^{16a}$ respectively combine each other together with the adjacent nitrogen atom to form includes 4 to 7-membered saturated or unsaturated monocyclic nitrogen-containing heterocyclyl with 1 to 3 heteroatoms containing at least one nitrogen atom selected from 1 to 3 nitrogen atoms, 1 oxygen atom or 1 sulfur atom. The saturated monocyclic nitrogen-containing heterocyclyl specifically includes azetidinyl, pyrrolidinyl, piperidinyl, piperazinyl, morpholinyl, thiomorpholinyl, perhydroazepinyl, etc. The unsaturated monocyclic nitrogen -containing heterocyclyl specifically includes imidazolyl, oxazolyl, thiazolyl, triazolyl, etc.

In case that optionally substituted alkyl, optionally substituted alkenyl and optionally substituted alkynyl are substituted, the substituent as used herein includes the above groups of (a) to (d).

In case that $R^{14}$, $R^{15}$ and $R^{16}$ are alkyl, alkenyl or alkynyl in the above (b), preferable ones are $C_{1-3}$ alkyl, $C_{2-3}$ alkenyl or $C_{2-3}$ alkynyl. The alkyl, alkenyl and alkynyl may be optionally substituted with 1 to 5 substituents selected from the group consisting of: halogen, hydroxy, carboxy, amino, carbamoyl, —$OR^{17}$, —$COOR^{17}$, —$NR^{18}$—$COR^{17}$, —$NR^{18}$—$COOR^{17}$, —$NR^{18}$—$SO_2R^{17}$, —$NR^{18}R^{19}$, and —$CONR^{18}R^{19}$, wherein $R^{17}$, $R^{18}$ and $R^{19}$ are defined as above. The alkyl, alkenyl and alkynyl in $R^{17}$, $R^{18}$ and $R^{19}$ preferably include $C_{1-3}$ alkyl, $C_{2-3}$ alkenyl and $C_{2-3}$ alkynyl.

The cycloalkyl in the above (c) preferably includes cyclopropyl, cyclobutyl, cyclopentyl or cyclohexyl. The cycloalkenyl in (c) includes cyclopentenyl or cyclohexenyl, specifically 1-cyclopentenyl, 1-cyclohexenyl. The monocyclic or bicyclic nonaromatic unsaturated heterocyclyl in (c) includes pyrrolinyl, 2,5-dihydrofuryl. The monocyclic or bicyclic saturated heterocyclyl in (c) includes pyrrolidinyl, piperidinyl, specifically 4-piperidinyl.

The aryl in the above (d) includes phenyl. The heteroaryl in (d) includes thienyl, furyl, pyridyl.

In case that optionally substituted cycloalkyl and cycloalkenyl are substituted, the substituent as used herein includes the above groups of (e).

In case that ring carbon atoms in optionally substituted monocyclic or bicyclic nonaromatic unsaturated heterocyclyl or monocyclic or bicyclic saturated heterocyclyl are substituted, the substituent as used herein includes the above groups of (e).

In the above (e), the alkyl preferably includes $C_{1-3}$ alkyl, and the alkoxy preferably includes $C_{1-3}$ alkoxy.

In case that ring nitrogen atoms in optionally substituted monocyclic or bicyclic nonaromatic unsaturated heterocyclyl or monocyclic or bicyclic saturated heterocyclyl are substituted, the substituent includes the above groups of (f).

In the above (f), the alkyl preferably includes $C_{1-4}$ alkyl. The alkanoyl preferably includes $C_{2-4}$ alkanoyl. The alkoxycarbonyl preferably includes $C_{2-4}$ alkoxycarbonyl. The alkylsulfonyl preferably includes $C_{1-4}$ alkylsulfonyl.

In case that optionally substituted aryl or heteroaryl is substituted, the substituent as used herein includes the above groups of (g) to (i).

Preferable embodiments of $R^{14}$, $R^{15}$ and $R^{16}$ in the above (h) are the same as the above (b).

In case that ring carbon atoms in "saturated or unsaturated monocyclic nitrogen-containing heterocyclyl" which $R^{12}$ and $R^{13}$, $R^{15}$ and $R^{16}$, $R^{18}$ and $R^{19}$, $R^{12a}$ and $R^{13a}$, and $R^{15a}$ and $R^{16a}$ respectively combine each other together with the adjacent nitrogen atom to form are substituted, the substituent includes the above groups of (e), preferably $C_{1-3}$ alkyl, $C_{1-3}$ alkoxy or oxo. In case that ring nitrogen atoms in the "saturated or unsaturated monocyclic nitrogen-containing heterocyclyl" are substituted, the substituent includes the above groups of (f), preferably $C_{1-4}$ alkyl, $C_{2-4}$ alkanoyl or $C_{2-4}$ alkoxycarbonyl.

Preferable embodiments of a compound of formula (1) are described in detail as below.

$R^1$ is preferably halogen, specifically chlorine, bromine or iodine. More preferable $R^1$ includes chlorine or bromine, particularly chlorine.

$R^2$ is preferably hydrogen or $C_{1-3}$ alkyl, more preferably hydrogen.

$R^3$ is preferably hydrogen or $C_{1-3}$ alkyl, more preferably hydrogen or methyl, particularly hydrogen.

$R^4$ is preferably $C_{1-4}$ alkyl, more preferably methyl, ethyl or isopropyl, particularly methyl or ethyl.

$R^5$ and $R^6$ are preferably the same or different and each hydrogen or methyl, and more preferably both are hydrogen.

l is preferably 1 or 2, more preferably 1.

m is preferably 1.

A combination of n and o specifically includes that o is 1 to 3 if n is 0, that o is 0 to 3 if n is 1, and that o is 0 to 3 if n is 2, preferably that o is 0 to 2 if n is 1, and that o is 0 to 2 if n is 2, more preferably that o is 1 if n is 2.

Preferable compounds among a compound of formula (1) include a compound wherein $R^1$ is halogen, both $R^2$ and $R^3$ are hydrogen and $R^4$ is $C_{1-3}$ alkyl in formula (Ar-1), or a compound wherein $R^1$ is halogen, both $R^2$ and $R^3$ are hydrogen, $R^5$ is hydrogen, $R^6$ is hydrogen or methyl and h is 1 in formula (Ar-2).

More preferable compounds of formula (1) include a compound wherein $R^1$ is chlorine or bromine, $R^4$ is methyl, ethyl or isopropyl in formula (Ar-1), or a compound wherein $R^1$ is chlorine or bromine, $R^5$ and $R^6$ are hydrogen, h is 1 in formula (Ar-2).

(1) In case that A in a compound of formula (1) is hydrogen, cyano or formyl, A is preferably hydrogen or cyano.

(2) In case that A in a compound of formula (1) is optionally substituted alkyl, optionally substituted alkenyl or optionally substituted alkynyl, the alkyl includes $C_{1-4}$ alkyl, the alkenyl includes $C_{2-4}$ alkenyl, and the alkynyl includes $C_{2-4}$ alkynyl. In case that these groups are substituted, the substituent includes the above groups of (a) to (d). A is preferably $C_{1-4}$ alkyl, or $C_{1-4}$ alkyl substituted with phenyl wherein phenyl may be further optionally substituted with the same or different 1 to 5 substituents selected from the group consisting of halogen, hydroxy, alkyl, alkoxy, alkanoyl, haloalkyl, haloalkoxy, amino and carbamoyl.

(3) In case that A in a compound of formula (1) is —COR$^7$, —CSR$^7$, —COOR$^7$, —SO$_2$R$^7$ or —CO—COR$^7$ wherein $R^7$ is defined as above, alkyl, alkenyl and alkynyl in $R^7$ are preferably $C_{1-3}$ alkyl, $C_{2-3}$ alkenyl and $C_{2-3}$ alkynyl, respectively, and the substituents of alkyl, alkenyl and alkynyl are 1 to 5, preferably 1 to 3, substituents selected from the above (a) to (d).

Preferable substituents of the above (a) may be (a-1) halogen, hydroxy, carboxy, amino, carbamoyl or cyano.

Preferable substituents of the above (b) may be (b-1) —OR$^{14a}$, —COR$^{14a}$, —COOR$^{14a}$, —O—COR$^{14a}$, —NR$^{15a}$—COR$^{14a}$, —NR$^{15a}$—COOR$^{14a}$, —NR$^{15a}$R$^{16a}$ or —CONR$^{15a}$R$^{16a}$ wherein R$^{14a}$, R$^{15a}$ and R$^{16a}$ are the same as defined above.

Preferable substituents of the above (c) may be (c-1) cycloalkyl which may be optionally substituted with the same or different 1 to 5 substituents selected from the group consisting of halogen, hydroxy, alkyl and alkoxy; or monocyclic or bicyclic saturated heterocyclyl wherein ring carbon atoms may be substituted with the same or different 1 to 5 substituents selected from the group consisting of halogen, hydroxy, alkyl and alkoxy, and ring nitrogen atoms may be optionally substituted with alkyl, alkanoyl or alkoxycarbonyl.

Preferable substituents of the above (d) may be (d-1) —R$^{21a}$ or —NR$^{15a}$—COR$^{21a}$, wherein R$^{15a}$ is the same as defined above, R$^{21a}$ is aryl or heteroaryl, and the group of (d-1) may be optionally substituted with the same or different 1 to 5 substituents selected from the group consisting of halogen, hydroxy, carboxy, haloalkyl, haloalkoxy, amino, carbamoyl, cyano, —R$^{14a}$, —OR$^{14a}$, —COR$^{14a}$, —NR$^{15a}$—COR$^{14a}$ and —NR$^{15a}$R$^{16a}$ wherein R$^{14a}$, R$^{15a}$ and R$^{16a}$ are the same as defined above.

The optionally substituted cycloalkyl in $R^7$ is preferably optionally substituted cyclopropyl, cyclobutyl, cyclopentyl or cyclohexyl. The optionally substituted cycloalkenyl in $R^7$ is preferably optionally substituted cyclopentenyl or cyclohexenyl, specifically 1-cyclopentenyl or 1-cyclohexenyl. In case that cycloalkyl or cycloalkenyl in $R^7$ is substituted, the substituent includes the above groups of (e), preferably halogen, hydroxy, alkyl or alkoxy:

The optionally substituted monocyclic or bicyclic saturated heterocyclyl in $R^7$ wherein heterocyclyl is attached via any ring carbon atoms is preferably tetrahydrofuryl, pyrrolidinyl or piperidinyl. The optionally substituted monocyclic or bicyclic nonaromatic unsaturated heterocyclyl in $R^7$ wherein heterocyclyl is attached via any ring carbon atoms is preferably 2,3-dihydrobenzofuryl or pyrrolinyl. In case that monocyclic or bicyclic saturated heterocyclyl, or monocyclic or bicyclic nonaromatic unsaturated heterocyclyl is substituted on any ring carbon atoms, the substituent includes the above groups of (e), preferably halogen, hydroxy, $C_{1-4}$ alkyl or $C_{1-4}$ alkoxy. In case that monocyclic or bicyclic saturated heterocyclyl, or monocyclic or bicyclic nonaromatic unsaturated heterocyclyl is substituted on any ring nitrogen atoms, the substituent includes the above groups of (f), preferably $C_{1-4}$ alkyl, $C_{2-5}$ alkanoyl, $C_{2-5}$ alkoxycarbonyl or $C_{1-4}$ alkylsulfonyl.

The optionally substituted aryl in $R^7$ is preferably phenyl. The optionally substituted heteroaryl in $R^7$ is preferably thienyl, furyl, pyridyl or pyrrolyl. In case that aryl or heteroaryl in $R^7$ is substituted, the substituent includes 1 to 5 substituents selected from the above groups of (g) to (i). A preferable one is selected from the group consisting of:

(g-1) halogen, nitro, hydroxy, carboxy, amino, carbamoyl, haloalkyl, haloalkoxy or cyano;

(h-1) —R$^{14a}$, —OR$^{14a}$, —COR$^{14a}$, —COOR$^{14a}$, —O—COR$^{14a}$, —NR$^{15a}$—COR$^{14a}$, —NR$^{15a}$—

COOR$^{14a}$ or —NR$^{15a}$R$^{16a}$ wherein R$^{14a}$, R$^{15a}$ and R$^{16a}$ are the same as defined above; and (i-1) phenyl or phenoxy, wherein the groups of (i-1) may be further optionally substituted with 1 to 5 substituents selected from the group consisting of halogen, hydroxy, alkyl and alkoxy.

(3-2) In case that A in a compound of formula (1) is —SO$_2$—R$^{7b}$ wherein R$^{7b}$ is the same as defined above, R$^{7b}$ is preferably C$_{1-4}$ alkyl, C$_{1-4}$ alkyl substituted with optionally substituted phenyl, or optionally substituted phenyl. The phenyl may be optionally substituted with 1 to 5, preferably 1 to 3, substituents selected from the group consisting of halogen, hydroxy, C$_{1-3}$ alkyl, C$_{1-3}$ alkoxy, C$_{2-4}$ alkanoyl, C$_{1-3}$ haloalkyl, C$_{1-3}$ haloalkoxy, C$_{2-4}$ alkoxycarbonyl, carboxy, amino and carbamoyl.

(3-3) In case that A in a compound of formula (1) is —COR$^{7c}$ or —CO—COR$^{7c}$, wherein R$^{7c}$ is the same as defined above, and R$^{7c}$ is optionally substituted alkyl or optionally substituted alkenyl, the alkyl is preferably C$_{1-3}$ alkyl and the alkenyl is preferably C$_{2-3}$ alkenyl. The substituent of alkyl or alkenyl may include the following (a-2) to (d-2):

(a-2) hydroxy, halogen, carbamoyl or cyano;

(b-2) —OR$^{14c}$, —COR$^{14c}$, —COOR$^{14c}$, —O—COR$^{14c}$, —NR$^{15c}$—COR$^{14c}$, —NR$^{15c}$R$^{16c}$ or —CONR$^{15c}$R$^{16c}$, wherein R$^{14c}$ and R$^{16c}$ are the same or different alkyl, and R$^{15c}$ is hydrogen or alkyl;

(c-2) cycloalkyl, or monocyclic or bicyclic saturated heterocyclyl, wherein each nitrogen atom of the monocyclic or bicyclic saturated heterocyclyl is optionally substituted with alkyl, alkanoyl or alkoxycarbonyl;

(d-2) —R$^{21c}$ or —NR$^{15c}$—COR$^{21c}$, wherein R$^{15c}$ is the same as defined above and R$^{21c}$ is aryl or heteroaryl, and the groups of (d-2) are optionally substituted with the same or different 1 to 5 substituents selected from the group consisting of halogen, hydroxy, carboxy, haloalkyl, haloalkoxy, amino, carbamoyl, cyano, —R$^{14c}$, —OR$^{14c}$, —COR$^{14c}$ and —COOR$^{14c}$ wherein R$^{14c}$ is the same as defined above.

In (b-2), R$^{14c}$ and R$^{16c}$ are preferably the same or different C$_{1-3}$ alkyl, and R$^{15c}$ is hydrogen or C$_{1-3}$ alkyl.

In (c-2), cycloalkyl is preferably cyclopropyl, cyclobutyl, cyclopentyl or cyclohexyl, and monocyclic or bicyclic saturated heterocyclyl is preferably piperidinyl or pyrrolidinyl wherein each nitrogen atom of the monocyclic or bicyclic saturated heterocyclyl may be preferably optionally substituted with C$_{1-3}$ alkyl, C$_{2-3}$ alkanoyl or C$_{2-3}$ alkoxycarbonyl.

In (d-2), aryl includes phenyl, and heteroaryl is preferably thienyl, furyl or pyridyl. The substituent of aryl or heteroaryl is preferably halogen, hydroxy, carboxy, C$_{1-3}$ haloalkyl, C$_{1-3}$ haloalkoxy, amino, carbamoyl, C$_{1-3}$ alkyl, C$_{1-3}$ alkoxy, C$_{2-3}$ alkanoyl or C$_{2-3}$ alkoxycarbonyl.

In case that R$^{7c}$ is optionally substituted alkyl or optionally substituted alkenyl, the substituent of alkyl or alkenyl may be more preferably the following groups:

(a-3) hydroxy, carbamoyl or cyano;

(b-3) —OR$^{14d}$, —COR$^{14d}$, —COOR$^{14d}$, —O—COR$^{14d}$, —NR$^{15d}$—COR$^{14d}$, —NR$^{15d}$R$^{16d}$ or —CONR$^{15d}$R$^{16d}$, wherein R$^{14d}$ and R$^{16d}$ are the same or different C$_{1-3}$ alkyl, R$^{15d}$ is hydrogen or C$_{1-3}$ alkyl.

Particularly, a preferable A is C$_{1-3}$ alkyl or C$_{2-3}$ alkenyl optionally substituted with the above groups of (a-3) or (b-3) on each R$^{7c}$, specifically methyl or ethyl optionally substituted with the above groups of (a-3) or (b-3).

In case that A in a compound of formula (1) is —COR$^{7c}$ wherein R$^{7c}$ is substituted alkyl, R$^{7c}$ specifically includes hydroxymethyl, 2-hydroxyisopropyl, acetoxymethyl, methoxymethyl, ethoxymethyl, 2-methoxycarbonylethyl, 2-ethoxycarbonylethyl, carbamoylmethyl, 2-carbamoylethyl, dimethylaminomethyl, diethylaminomethyl, 2-diethylaminoethyl, 3-dimethylaminopropyl, 3-aminopropyl, acetaminomethyl, 3-(tert-butoxycarbonyl)aminopropyl, 1-piperidinyl)methyl, 2-(1-piperidinyl)ethyl, 2-carboxyethyl, 4-piperidinyl)methyl, cyanomethyl, 1-cyanoethyl or 2-cyanoethyl.

In case that A in a compound of formula (1) is —COR$^{7c}$ wherein R$^{7c}$ is substituted alkenyl, R$^{7c}$ specifically includes 2-cyclopropylvinyl, 2-furylvinyl or 2-(2-thienyl)vinyl.

In case that A in a compound of formula (1) is —CO—COR$^{7c}$ wherein R$^{7c}$ is the same as defined above, R$^{7c}$ is preferably alkyl, more preferably C$_{1-3}$ alkyl.

(3-4) In case that A in a compound of formula (1) is —COR$^{7d}$ wherein R$^{7d}$ is the same as defined above and is optionally substituted cycloalkyl, optionally substituted cycloalkenyl, optionally substituted monocyclic or bicyclic nonaromatic unsaturated heterocyclyl, or optionally substituted monocyclic or bicyclic saturated heterocyclyl, cycloalkyl is preferably cyclopropyl, cyclobutyl, cyclopentyl or cyclohexyl, and cycloalkenyl is preferably cyclopentenyl or cyclohexenyl. The monocyclic nonaromatic unsaturated heterocyclyl includes pyrrolinyl or 2,5-dihydrofuryl. The bicyclic nonaromatic unsaturated heterocyclyl includes 2,3-dihydrobenzofuryl. The monocyclic saturated heterocyclyl includes pyrrolidinyl, piperidinyl or tetrahydrofuryl. The substituent of each ring carbon atom is preferably halogen, hydroxy, C$_{1-3}$ alkyl or C$_{1-3}$ alkoxy. The substituent of each ring nitrogen atom is preferably C$_{1-3}$ alkyl, C$_{2-4}$ alkanoyl, C$_{2-4}$ alkoxycarbonyl or C$_{1-3}$ alkylsulfonyl.

(3-5) In case that A in a compound of formula (1) is —COR$^{7e}$ wherein R$^{7e}$ is the same as defined above and is optionally substituted aryl or optionally substituted heteroaryl, aryl is preferably phenyl and heteroaryl is preferably thienyl, furyl, pyrrolyl or pyridyl. The substituents of these groups are preferably the following groups:

(g-1) halogen, nitro, hydroxy, carboxy, amino, carbamoyl, haloalkyl, haloalkoxy or cyano;

(h-1) —R$^{14a}$, —OR$^{14a}$, —COR$^{14a}$, —COOR$^{14a}$, —O—COR$^{14a}$, —NR$^{15a}$—COR$^{14a}$, —NR$^{15a}$—COOR$^{14a}$ or —NR$^{15a}$R$^{16a}$, wherein R$^{14a}$, R$^{15a}$ and R$^{16a}$ are the same as defined above; or (i-1) phenyl or phenoxy, wherein the groups of (i-1) may be optionally substituted with 1 to 5 substituents selected from the group consisting of halogen, hydroxy, alkyl and alkoxy. More preferable one is selected from the following groups:

(g-2) halogen, amino, carbamoyl or cyano;

(h-2) —R$^{14e}$, —OR$^{14e}$, —O—COR$^{14e}$, —NR$^{15e}$—COR$^{14e}$, —NR$^{15e}$—COOR$^{14e}$ or —NR$^{15e}$R$^{16e}$, wherein R$^{14e}$, R$^{15e}$ and R$^{16e}$ is the same as defined above; or (i-2) phenyl or phenoxy.

In case that A in a compound of formula (1) is —COR$^{7e}$ wherein R$^{7e}$ is optionally substituted phenyl, R$^{7e}$ specifically includes phenyl, 2-, 3- or 4-chlorophenyl, 2-, 3- or 4-bromophenyl, 2-, 3- or 4-fluorophenyl, 2-, 3- or 4-methylphenyl, 2-, 3- or 4-cyanophenyl, 4-ethylphenyl, 4-t-butylphenyl, 2-, 3- or 4-acetoxyphenyl, 2-, 3- or 4-acetylaminophenyl, 2-, 3- or 4-dimethylaminophenyl, 4-methoxycarbonylphenyl, 2-, 3- or 4-phenoxyphenyl, 2-, 3- or 4-biphenyl, or 3-chloro-4-aminophenyl.

(3-6) In case that A in a compound of formula (1) is —COOR$^{7f}$ wherein R$^{7f}$ is the same as defined above, R$^{7f}$ is preferably C$_{1-4}$ alkyl, C$_{2-4}$ alkenyl, or optionally substituted phenyl wherein phenyl may be preferably optionally substituted with the same or different 1 to 5, preferably 1 to 3, substituents selected from the group consisting of halogen, nitro, hydroxy, $C_{1-3}$ alkyl, $C_{1-3}$ alkoxy, $C_{2-4}$ alkanoyl, $C_{1-3}$ haloalkyl and $C_{1-3}$ haloalkoxy. More preferable $R^{7f}$ is $C_{1-3}$ alkyl or $C_{2-3}$ alkenyl.

(4) In case that A in a compound of formula (1) is —CO—COOR$^8$ wherein R$^8$ is the same as defined above, R$^8$ is preferably $C_{1-4}$ alkyl, more preferably $C_{1-2}$ alkyl.

(5-1) In case that A in a compound of formula (1) is —CONR$^{9a}$—OR$^{10a}$ wherein R$^{9a}$ and R$^{10a}$ are the same as defined above, R$^{9a}$ and R$^{10a}$ are preferably the same or different and each hydrogen, $C_{1-3}$ alkyl, $C_{2-3}$ alkenyl or $C_{2-3}$ alkynyl, and more preferably, R$^{9a}$ and R$^{10a}$ are $C_{1-3}$ alkyl.

(6-1) In case that A in a compound of formula (1) is —CONR$^{12a}$R$^{13a}$, —CSNR$^{12a}$R$^{13a}$ or —SO$_2$NR$^{12a}$R$^{13a}$ wherein R$^{12a}$ and R$^{13a}$ are the same as defined above, R$^{12a}$ is preferably hydrogen, $C_{1-3}$ alkyl, $C_{2-3}$ alkenyl, $C_{1-3}$ alkyl substituted with $C_{2-3}$ alkoxycarbonyl, $C_{1-3}$ alkyl substituted with optionally substituted phenyl, or optionally substituted phenyl. The substituent of phenyl is preferably halogen, nitro, hydroxy, carboxy, $C_{1-3}$ haloalkyl, $C_{1-3}$ haloalkoxy, amino, carbamoyl, $C_{1-3}$ alkyl, $C_{1-3}$ alkoxy, $C_{2-4}$ alkanoyl, $C_{2-4}$ alkoxycarbonyl or $C_{2-4}$ alkanoyloxy. R$^{13a}$ is preferably hydrogen or $C_{1-3}$ alkyl, or R$^{12a}$ and R$^{13a}$ combine each other together with the adjacent nitrogen atom to form optionally substituted saturated or unsaturated monocyclic nitrogen-containing heterocycle. The saturated monocyclic nitrogen-containing heterocycle includes pyrrolidine, piperidine or morpholine, and the unsaturated monocyclic nitrogen-containing heterocycle includes imidazole or pyrroline.

More preferably, R$^{12a}$ and R$^{13a}$ are the same or different $C_{1-3}$ alkyl, or R$^{12a}$ is hydrogen and R$^{13a}$ is phenyl which may be optionally substituted with 1 to 2 halogens, $C_{1-3}$ haloalkyl, hydroxy, $C_{1-3}$ alkyl, $C_{1-3}$ alkoxy, $C_{2-4}$ alkanoyl, $C_{2-4}$ alkanoyloxy, $C_{2-4}$ alkoxycarbonyl, carboxy, amino or carbamoyl. Alternatively, R$^{12a}$ and R$^{13a}$ preferably combine each other together with the adjacent nitrogen atoms to form pyrrolidine, piperidine, morpholine or imidazole.

A compound of formula (1) may encompass all tautomers, geometric isomers, stereoisomers and a mixture thereof depending on types of substituents.

In other words, a compound of formula (1) with one or more chiral carbon atoms exists in the form of a diastereomer or optical isomer, and the present invention encompasses a mixture or an isolated one of the diastereomer or optical isomer.

A pharmaceutically acceptable salt includes an acid addition salt and a base addition salt. For example, the acid addition salt includes an inorganic acid salt such as hydrochloride, hydrobromide, sulfate, hydroiodide, nitrate or phosphate, or an organic acid salt such as citrate, oxalate, acetate, formate, propionate, benzoate, trifluoroacetate, fumarate, maleate, malonate, succinate, tartrate, lactate, malate, pyruvate, methanesulfonate, benzenesulfonate or p-toluenesulfonate. The base addition salt includes an inorganic base salt such as sodium salt, potassium salt, calcium salt, magnesium salt, ammonium salt, or an organic base salt such as triethylammonium salt, triethanolammonium salt, pyridinium or diisopropylammonium salt. A basic amino acid salt or an acidic amino acid salt such as alginate, aspartate or glutamate may be also included.

A compound of formula (1) and a pharmaceutically acceptable salt thereof may be a solvate such as a hydrate or an ethanolate, and the hydrate and/or solvate may be included in the invented compound.

A compound of formula (1) may be prepared according to the following methods. Any starting materials which are not listed below may be prepared according to the following methods, or the conventional methods well known to those skilled in the art or any equivalent methods.

(Preparation 1)

For example, a compound of formula (1) may be prepared according to the following method.

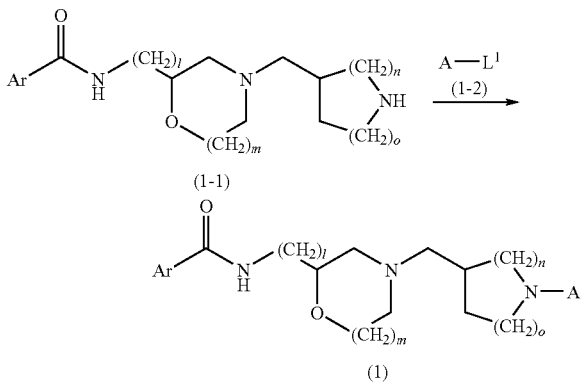

In the above formula, A, Ar, l, m, n and o are the same as defined above, and L$^1$ is a leaving group.

Specifically, a compound of formula (1) may be prepared by reacting a compound of formula (1-1) with a reactive derivative of formula (1-2) in the presence of an appropriate additive such as a base.

In case that A is —COR$^7$ wherein R$^7$ is the same as defined above, the reactive derivative may include a carboxylic acid compound of formula (1-3):

R$^7$—COOH    (1-3)

wherein R$^7$ is the same as defined above; and an alkyl ester, particularly methylester, an active ester, an acid anhydride, an acid halide, particularly an acid chloride, of the carboxylic acid compound.

A compound of formula (1-3) may be reacted in the presence of a condensing agent such as 1,3-dicyclohexylcarbodiimide, 1-ethyl-3-(3-dimethylaminopropyl)carbodiimide hydrochloride, N,N'-carbonyldiimidazole, benzotriazol-1-yloxytris(dimethylamino)phosphonium hexafluorophosphate, N,N'-carbonyldisuccinicimide, 1-ethoxycarbonyl-2-ethoxy-1,2-dihydroquinoline, diphenylphosphoryl azide, or propanephosphonic anhydride. In case that 1,3-dicyclohexylcarbodiimide or 1-ethyl-3-(3-dimethylaminopropyl)carbodiimide hydrochloride is used as the condensing agent, N-hydroxysuccinic imide, 1-hydroxybenzotriazole, 3-hydroxy-1,2,3-benzotriazin-4(3H)-one, N-hydroxy-5-norbornene-2,3-dicarboxyimide, etc. may be added to react.

The active ester includes p-nitrophenyl ester, pentachlorophenyl ester, pentafluorophenyl ester, N-hydroxysuccinic imide ester, N-hydroxyphthalimide ester, 1-hydroxybenzotriazole ester, 8-hydroxyquinoline ester, 2-hydroxyphenyl ester, etc. A symmetrical acid anhydride or mixed acid anhydride may be used as the acid anhydride, and the mixed acid anhydride includes that with chlorocarbonic acid alkyl ester such as ethyl chlorocarbonate or isobutyl chlorocarbonate, that with chlorocarbonic acid aralkyl ester such as benzyl chlorocarbonate, that with chlorocarbonic acid aryl ester such as phenyl chlorocarbonate, and that with alkanoic acid such as isovaleric acid or pivalic acid.

A compound of formula (1-1) is reacted with a compound of formula (1-2) in a solvent or under neat. The solvent used herein should be optionally selected depending on types of starting compounds, etc., and by way of example, includes aromatic hydrocarbon such as benzene, toluene or xylene, ether such as diethyl ether, tetrahydrofuran, dioxane or cyclopentylmethyl ether, halogenated hydrocarbon such as methylene chloride or chloroform, ketone such as acetone or methylethylketone, ethyl acetate, acetonitrile, N,N-dimethylformamide, or dimethylsulfoxide, which is used alone or in a mixture of two or more solvents.

The reaction may be optionally carried out in the presence of a base which includes alkali hydroxide such as sodium hydroxide or potassium hydroxide, alkaline carbonate such as sodium carbonate or potassium carbonate, alkaline bicarbonate such as sodium bicarbonate or potassium bicarbonate, or an organic base such as triethylamine, tributylamine, diisopropylethylamine or N-methylmorpholine, and the base may be replaced with excess amounts of a compound of formula (1-1).

A reaction temperature depends on types of starting compounds used herein, and it is usually about −30° C. to about 200° C., preferably about −10° C. to about 150° C.

A compound of formula (1-1) of Preparation 1 corresponds to a compound wherein A is hydrogen in formula (1), i.e. an intermediate, and may be prepared according to the following Preparation 2 or 3.

(Preparation 2)

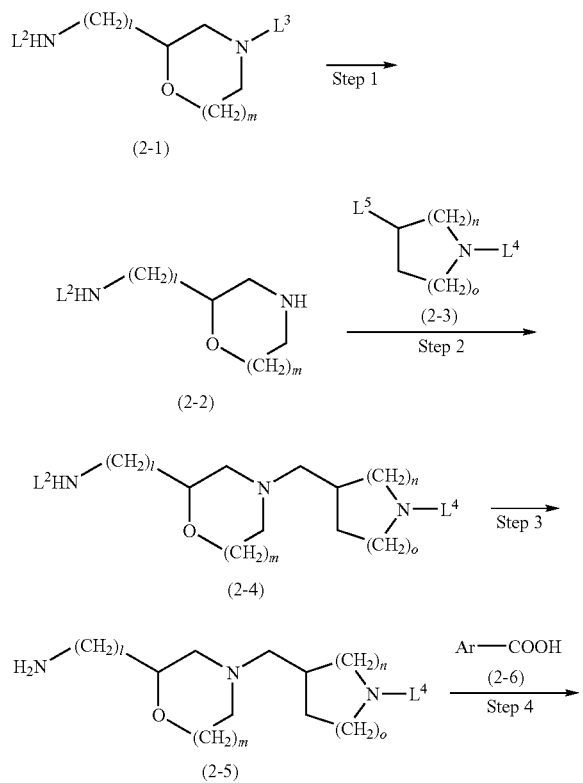

In the above scheme, A, Ar, l, m, n and o are the same as defined above, $L^2$, $L^3$ and $L^4$ are protective groups which can be eliminated via hydrolysis or hydrogenolysis, $L^2$ and $L^3$, and $L^2$ and $L^4$ can be deprotected under different reaction conditions each other, and $L^5$ is —$CH_2$-$L^6$, wherein $L^6$ is a leaving group, formyl or carboxy.

(Preparation 3)

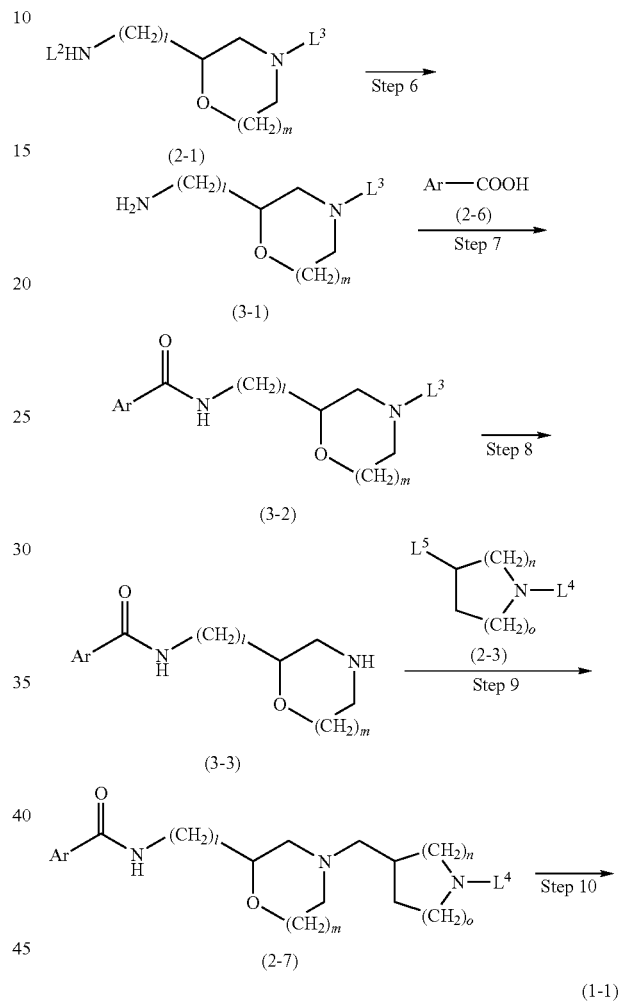

In the above scheme, A, Ar, l, m, n, o, $L^2$, $L^3$, $L^4$ and $L^5$ are the same as defined above.

Steps 1 to 10 in the above Preparation 2 or 3 are illustrated as follows.

1) Deprotection Reaction

Steps 1, 3, 5, 6, 8 and 10 are a deprotection reaction step. In Preparations 2 and 3, a protective group which can be eliminated via hydrolysis among that used as $L^2$, $L^3$ and $L^4$ includes ethoxycarbonyl, tert-butoxycarbonyl, acetyl, benzoyl, trifluoroacetyl, benzyloxycarbonyl, 3- or 4-chlorobenzyloxycarbonyl, triphenylmethyl, methanesulfonyl, p-toluenesulfonyl, etc., and one which can be eliminated via hydrogenolysis includes benzyloxycarbonyl, 3- or 4-chlorobenzyloxycarbonyl, benzylsulfonyl, etc.

A deprotection via hydrolysis may be carried out according to conventional methods, for example by contacting with water in an appropriate solvent under acidic or basic conditions. The solvent used in the deprotection includes alcohol such as methanol, ethanol or isopropanol, acetonitrile, dioxane, water, or a mixture thereof. The acid used therein includes a mineral acid such as hydrochloric acid, hydrobromic acid, hydroiodic acid or sulfuric acid, or an organic acid such as formic acid, acetic acid, trifluoroacetic acid, p-toluenesulfonic acid or methanesulfonic acid. The base used therein includes alkaline hydroxide such as sodium hydroxide or potassium hydroxide, or alkaline carbonate such as sodium carbonate or potassium carbonate. The reaction temperature is usually about 0° C. to 150° C.

A deprotection via hydrogenolysis may be also carried out according to conventional methods, for example by the treatment in an appropriate solvent in the presence of a catalyst such as palladium carbon or Raney nickel and in the presence of hydrogen or a hydrogen donor such as ammonium formate or cyclohexene. The solvent used in the deprotection includes, for example, alcohol such as ethanol or methanol, water, acetic acid, dioxane, tetrahydrofuran, ethyl acetate, N,N-dimethylformamide. The reaction temperature is usually about 0° C. to about 80° C., and the reaction may be carried out under normal or increased pressure.

A protective group $L^2$ is deprotected under different conditions from those of $L^3$ and $L^4$. For example, "$L^2HN$—" is phthalimide, $L^3$ is t-butoxycarbonyl, and $L^4$ is acetyl.

2) Alkylation Reaction

When a compound of formula (2-3), an intermediate of Preparations 2 and 3, wherein $L^5$ is —$CH_2$-$L^6$ in which $L^6$ is a leaving group is used, steps 2 and 9 are an alkylation reaction in a solvent or under neat. The solvent used therein should be optionally selected depending on types of starting compounds, etc., but it includes, for example, aromatic hydrocarbon such as benzene, toluene or xylene, ether such as diethylether, tetrahydrofuran, cyclopentylmethylether or dioxane, halogenated hydrocarbon such as methylene chloride or chloroform, alcohol such as ethanol, isopropanol or ethylene glycol, ketone such as acetone or methylethylketone, ethyl acetate, acetonitrile, N,N-dimethylformamide, or dimethylsulfoxide. The solvent may be used alone or in a mixture.

The reaction may be carried out in the presence of a base as appropriate, and the base includes alkali hydroxide such as sodium hydroxide or potassium hydroxide, alkali carbonate such as sodium carbonate or potassium carbonate, alkali bicarbonate such as sodium bicarbonate or potassium bicarbonate, or an organic base such as triethylamine, tributylamine, diisopropylethylamine or N-methylmorpholine. Excess amount of an amine which is a substrate of the alkylation may be also used as the base.

$L^6$ is an leaving group which includes, for example, halogen such as chlorine, bromine or iodine, alkylsulfonyloxy such as methanesulfonyloxy, arylsulfonyloxy such as benzenesulfonyloxy or p-toluenesulfonyloxy, preferably halogen, particularly chlorine and bromine, or methanesulfonyloxy and p-toluenesulfonyloxy. The reaction in which $L^6$ is chlorine or bromine may smoothly proceed by the addition of an alkali metal iodide such as sodium iodide or potassium iodide. The reaction temperature depends on types of starting compounds used therein, but usually, about 0° C. to about 200° C., preferably about 20° C. to about 150° C.

A compound of formula (2-3) is commercially available or may be prepared according to known methods. Specifically, the corresponding alcohol derivative of formula (2-3a) may be converted into a leaving group by a conventional method to give a compound of formula (2-3b).

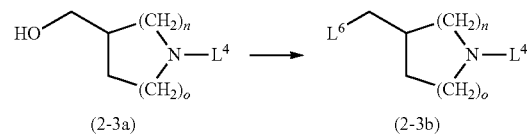

(2-3a)          (2-3b)

In the above scheme, n, o, $L^4$ and $L^6$ are the same as defined above.

For example, a compound of formula (2-3a) may be reacted with carbon tetrachloride or carbon tetrabromide and triphenylphosphine to give a compound wherein $L^6$ is chlorine atom or bromine atom. A compound of formula (2-3a) may be also reacted with sulfonyl chloride compound such as benzenesulfonyl chloride in the presence of a base to give a compound wherein $L^6$ is arylsulfonyloxy or alkylsulfonyloxy.

3) Reductive Alkylation Reaction

When a compound of formula (2-3), an intermediate of Preparations 2 and 3, wherein $L^5$ is formyl is used, steps 2 and 9 are a reductive alkylation reaction which is carried out by a catalytic reduction using platinum oxide as a catalyst in the presence of a catalytic amount of an acid, or in the presence of a borane complex such as pyridine borane or triethyl borane, sodium borohydride, sodium triacetoxyhydroborate, or sodium cyanoborohydride. The solvent used therein includes a solvent used in the above 2). The acid used therein includes p-toluenesulfonic acid. The reaction temperature is usually about 0° C. to about 100° C., preferably about 20° C. to about 80° C.

A compound of formula (2-3) used herein is commercially available or may be prepared according to known methods. Specifically, the corresponding alcohol derivative of formula (2-3a) may be oxidized by a conventional method to give a formyl derivative of formula (2-3c). For example, a compound of formula (2-3a) may be oxidized by phosgene, dimethylsulfoxide and triethylamine. Alternatively, the corresponding carboxylic acid or an ester thereof may be reduced by a conventional method to give a compound of formula (2-3c). For example, a compound of formula (2-3d) may be reduced by DIBAH (diisobutylaluminum hydride).

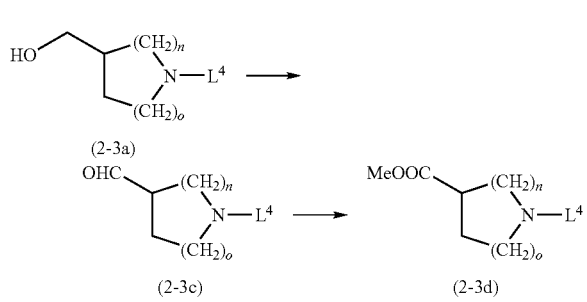

(2-3c)          (2-3d)

In the above scheme, n, o, $L^4$ and $L^6$ are the same as defined above.

A compound of formula (2-3d) used in the above step is commercially available or may be prepared according to known methods.

4) Amidation Reaction

When a compound of formula (2-3), an intermediate of Preparations 2 and 3, wherein $L^5$ is carboxy is used, step 2 is a process of amidating followed by reducing. The amidation reaction may be carried out according to the method described in the above Preparation 1. The reductive reaction may be carried out according to the method described in the following 5).

The amidation reaction in step 4 of Preparation 2 and step 7 of Preparation 3 may be also carried out by the following method. Specifically, a compound of formula (2-7) may be prepared by treating a compound of formula (2-5) with a compound of formula (2-6) or a reactive derivative thereof. A compound of formula (3-2) may be prepared by treating a compound of formula (3-1) with a compound of formula (2-6) or a reactive derivative thereof.

The reactive derivative of a compound of formula (2-6) includes, for example, a lower alkyl ester, particularly methyl ester, an active ester, an acid anhydride, or an acid halide, particularly acid chloride. The active ester includes p-nitrophenyl ester, pentachlorophenyl ester, pentafluorophenyl ester, N-hydroxysuccinic imide ester, N-hydroxyphthalimide ester, 1-hydroxybenzotriazole ester, 8-hydroxyquinoline ester or 2-hydroxyphenyl ester. The acid anhydride includes a symmetrical acid anhydride or a mixed acid anhydride, and the mixed acid anhydride includes a mixed acid anhydride with chlorocarbonic alkyl ester such as ethyl chlorocarbonate or isobutyl chlorocarbonate, a mixed acid anhydride with chlorocarbonic aralkyl ester such as benzyl chlorocarbonate, a mixed acid anhydride with chlorocarbonic aryl ester such as phenyl chlorocarbonate, or a mixed acid anhydride with alkanoic acid such as isovaleric acid or pivalic acid.

A carboxylic acid of formula (2-6) may be reacted in the presence of a condensing agent such as 1,3-dicyclohexylcarbodiimide, 1-ethyl-3-(3-dimethylaminopropyl)carbodiimide hydrochloride, N,N'-carbonyldiimidazole, benzotriazol-1-yloxytris(dimethylamino)phosphonium hexafluorophosphate, N,N'-carbonyldisuccinic imide, 1-ethoxycarbonyl-2-ethoxy-1,2-dihydroquinoline, diphenylphosphoryl azide, or propanephosphonic acid anhydride. When 1,3-dicyclohexylcarbodiimide or 1-ethyl-3-(3-dimethylaminopropyl)carbodiimide hydrochloride is used as a condensing agent, N-hydroxysuccinic imide, 1-hydroxybenzotriazole, 3-hydroxy-1,2,3-benzotriazin-4(3H) -one or N-hydroxy-5-norbomene-2,3-dicarboxyimide may be added in the reaction.

A carboxylic acid of formula (2-6) or a reactive derivative thereof may react with a compound of formula (2-5) or a compound of formula (3-1) in a solvent or under neat. The solvent used therein should be optionally selected depending on types of starting compounds, and for example, includes aromatic hydrocarbon such as benzene, toluene or xylene, ether such as diethylether, tetrahydrofuran, cyclopentylmethyl ether or dioxane, halogenated hydrocarbon such as methylene chloride or chloroform, ketone such as acetone or methylethylketone, ethyl acetate, acetonitrile, N,N -dimethylformamide, or dimethylsulfoxide. The solvent may be used alone or in a mixture.

The reaction may be carried out in the presence of a base as appropriate, and the base includes an alkali hydroxide such as sodium hydroxide or potassium hydroxide, an alkali carbonate such as sodium carbonate or potassium carbonate, an alkali bicarbonate such as sodium bicarbonate or potassium bicarbonate, or an organic base such as triethylamine, tributylamine, diisopropylethylamine or N-methylmorpholine. Excess amount of a compound of formula (2-5) or a compound of formula (3-1) may be also used as the base.

The reaction temperature depends on types of starting compounds, usually about −30° C. to about 200° C., preferably about −10° C. to about 150° C.

A compound of formula (2-6) may be prepared according to, for example, methods described in JP11-209347, JP11-217372 and JP11-228541.

5) Reductive Reaction

The reductive reaction following the amidation in step 2 of Preparation 2 may be carried out by using an appropriate reducing agent. Specifically, the reducing agent used therein includes, for example, diborane, lithium aluminum hydride and an alkoxy complex or a transition metal salt thereof, aluminum chloride, boron trifluoride, phosphorus oxychloride, or sodium borohydride with carboxylic acid (e.g., acetic acid, trifluoroacetic acid). The reductive reaction may be carried out in a solvent such as ether including diethylether, tetrahydrofuran, cyclopentylmethylether, dimethoxyethane, dioxane or diglyme, toluene, chloroform, or methylene chloride, and optionally selected depending on types of reducing agents used therein. The reaction temperature depends on types of reducing agents, usually about 0° C. to about 160° C., preferably about 10° C. to 80° C.

A starting compound of formula (2-1) in the above Preparations 2 and 3 is commercially available, or may be prepared according to known methods.

(Preparation 4)

A compound of formula (1) wherein A is —CONR$^{12}$R$^{13}$, —CSNR$^{12}$R$^{13}$ or —SO$_2$ NR$^{12}$R$^{13}$ in which R$^{12}$ and R$^{13}$ are the same as defined above may be prepared by a similar reaction to that of Preparation 1. A reactive derivative of formula (1-2) may include a compound wherein L$^1$ is halogen. The halogen includes chlorine atom, bromine atom or iodine atom, more preferably chlorine atom.

The reaction of a compound of formula (1-1) with a compound of formula (1-2) is carried out in a solvent or under neat. The solvent used therein should be optionally selected depending on types of starting compounds, and for example, includes aromatic hydrocarbon such as benzene, toluene or xylene, ether such as diethylether, tetrahydrofuran, cyclopentylmethyl ether or dioxane, halogenated hydrocarbon such as methylene chloride or chloroform, ketone such as acetone or methylethylketone, ethyl acetate, acetonitrile, N,N-dimethylformamide, or dimethylsulfoxide. The solvent may be used alone or in a mixture.

The reaction is carried out in the presence of a base as appropriate, and the base includes alkali hydroxide such as sodium hydroxide or potassium hydroxide, alkali carbonate such as sodium carbonate or potassium carbonate, alkali bicarbonate such as sodium bicarbonate or potassium bicarbonate, or an organic base such as triethylamine, tributylamine, diisopropylethylamine or N-methylmorpholine. Excess amount of a compound of formula (1-1) may be also used as the base. The reaction temperature depends on types of starting compounds used therein, etc., usually about −20° C. to about 150° C., preferably about −10° C. to about 80° C.

A compound of formula (1) wherein. A is —CONR$^{12}$R$^{13}$ may be also prepared by treating a chloromethyl carbamate compound, which may be obtained by treating chloromethyl chlorocarbonate with A-H, with a compound of formula (1-1) under a similar condition of the above Preparation according to Synth. Commun., 1996, 26, 4253. Alcohol such as ethanol may be also used as a solvent in the reaction.

A compound of formula (1-2) is commercially available, or may be prepared according to known methods.

(Preparation 5)

A compound of formula (1) wherein A is —CONHR$^{12}$ or —CSNHR$^{12}$ in which R$^{12}$ is the same as defined above may be prepared by treating a compound of formula (1-1) with a compound of formula (1-5) or formula (1-6):

$$O=C=N-R^{12} \qquad (1\text{-}5)$$

$$S=C=N-R^{12} \qquad (1\text{-}6)$$

wherein R$^{12}$ is the same as defined above.

The reaction of a compound of formula (1-1) with a compound of formula (1-5) or (1-6) may be carried out in a solvent or under neat. The solvent used therein should be optionally selected depending on types of starting compounds, etc., and for example, a solvent of the above Preparation 2 may be used. The reaction temperature depends on types of starting compounds used therein, etc. usually about 0° C. to about 250° C., preferably about 25° C. to about 200° C.

A compound of formula (1-5) or (1-6) is commercially available, or may be prepared according to known methods.
(Preparation 6)

A compound of formula (1) wherein A is —CONR$^{12}$R$^{13}$ or —CSNR$^{12}$R$^{13}$ in which R$^{12}$ and R$^{13}$ are the same as defined above may be also prepared by the following Preparation:

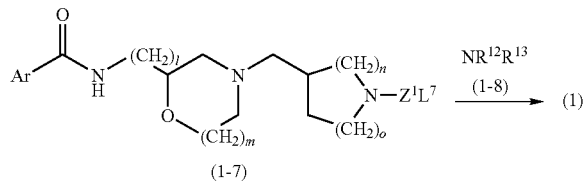

wherein Z$^1$ is —CO— or —CS—, is a leaving group, and Ar, l, m, n and o are the same as defined above.

The reaction is carried out in a solvent or under neat. The solvent used therein should be optionally selected depending on types of starting compounds, etc., and for example, a solvent of the above Preparation 2, 2) may be used. The reaction temperature depends on types of starting compounds, etc., usually about 0° C. to about 250° C., preferably about 25° C. to about 200° C.

A compound of formula (1-7) may be prepared by reacting a compound of formula (1-1) with N,N'-carbonyldiimidazole, phosgene, diphosgene, triphosgene, thiophosgene, sulfuryl chloride, di(2-pyridyl)carbonate, N,N'-disuccinimidyl carbonate, bis(4-nitrophenyl) carbonate, bis(trichloromethyl) carbonate, phenoxycarbonyltetrazole, phenyl chlorocarbonate, chloromethyl chloroformate, 2,4,5-trichlorophenyl chlorocarbonate, trichloromethyl chlorocarbonate, 1-chloroethyl chlorocarbonate, 1,2,2,2-tetrachloroethyl chlorocarbonate or norborn-5-ene-2,3-dicarboxyimidyl chlorocarbonate in the presence of a base used in Preparation 2, 2), and a leaving group L$^7$ depends on each reagent. For example, L$^7$ is imidazole in case that N,N'-carbonyldiimidazole is used, and L$^7$ is chlorine atom in case that phosgene is used. The reaction may be carried out in a solvent and under reaction conditions of the above Preparation 2, 2).

A compound of formula (1-8) is commercially available, or may be prepared according to known methods.
(Preparation 7)

A compound of formula (1) wherein A is —SO$_2$R$^7$ in which R$^7$ is the same as defined above may be prepared by reacting a compound of formula (1-1) with a compound of formula (1-9):

L$^1$-SO$_2$—R$^7$ (1-9)

wherein L$^1$ and R$^7$ are the same as defined above.

The reaction of a compound of formula (1-1) with a compound of formula (1-9) is carried out in a solvent or under neat. The solvent used therein should be optionally selected depending on types of starting compounds, etc., and for example, includes aromatic hydrocarbon such as benzene, toluene or xylene, ether such as diethylether, tetrahydrofuran, cyclopentylmethyl ether or dioxane, halogenated hydrocarbon such as methylene chloride or chloroform, ketone such as acetone or methylethyl ketone, ethyl acetate, acetonitrile, N,N-dimethylformamide, or dimethylsulfoxide. The solvent may be used alone or in a mixture.

The reaction may be carried out in the presence of a base as appropriate, and the base includes alkali hydroxide such as sodium hydroxide or potassium hydroxide, alkali carbonate such as sodium carbonate or potassium carbonate, alkali bicarbonate such as sodium bicarbonate or potassium bicarbonate, or an organic base such as triethylamine, tributylamine, diisopropylethylamine or N-methylmorpholine. Excess amount of a compound of formula (1-1) may be used as the base. The reaction temperature depends on types of starting compounds, etc., usually about –20° C. to about 150° C., preferably about –10° C. to about 80° C.

A compound of formula (1-9) is commercially available, or may be prepared according to known methods.
(Preparation 8)

A compound of formula (1) wherein A is optionally substituted alkyl, optionally substituted alkenyl or optionally substituted alkynyl may be prepared by reacting a compound of formula (1-2) or formula (1-10):

OHC-A$^2$ (1-10)

wherein A$^2$ is optionally substituted alkyl, optionally substituted alkenyl or optionally substituted alkynyl.

The reaction of a compound of formula (1-1) with a compound of formula (1-2) may be carried out by the alkylation reaction of the above Preparation 2, 2). The reaction of a compound of formula (1-1) with a compound of formula (1-10) may be carried out by the reductive alkylation reaction of the above Preparation 2, 3).

A compound of formula (1-2) or formula (1-10) is commercially available, or may be prepared according to known methods.
(Preparation 9)

A compound of formula (1) wherein A is cyano may be prepared by reacting a compound of formula (1-1) with a compound of formula (1-11):

L$^1$-CN (1-11)

wherein L$^1$ is the same as defined above.

The reaction of a compound of formula (1-1) with a compound of formula (1-11) may be carried out under a similar condition to that of the alkylation reaction of the following Preparation 2, 2).

A compound of formula (1-11) is commercially available, or may be prepared according to known methods.
(Preparation 10)

A compound of formula (1) may be also prepared by reacting a compound of formula (2-6) or a reactive derivative thereof with a compound of formula (10-1):

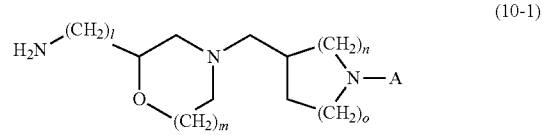

wherein A, l, m, n and o are the same as defined above.

The reactive derivative of a compound of formula (2-6) may include the same reactive derivative of a compound of formula (1-3). The reaction of a carboxylic acid compound of formula (2-6) or a reactive derivative thereof with a compound of formula (10-1) may be carried out under a similar condition of the reaction of a compound of formula (1-3) with a compound of formula (1-1).

(Preparation 11)

A compound of formula (10-1) may be prepared by the following preparation step.

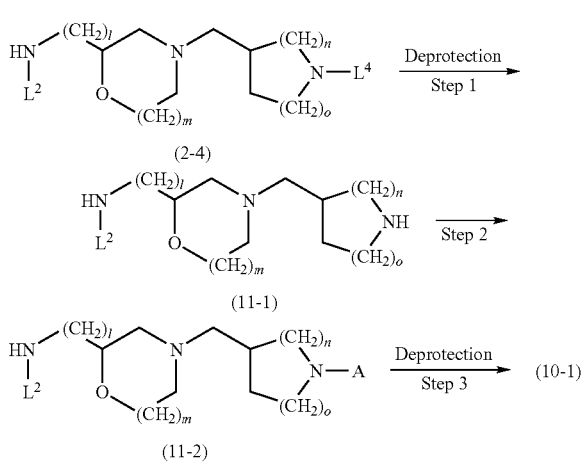

In the above scheme, $L^2$, $L^4$, A, l, m, n and o are the same as defined above.

The reaction of the above step 2 may be carried out according to any one of methods described in the above Preparations 1 to 9. The reactions of the above steps 1 and 3 may be carried out by using a deprotection reaction of the above Preparation 2, 1).

Compounds of formula (11-1) and formula (11-2) may be also prepared according to methods described in the following Reference Examples 12 to 19.

(Preparation 12)

A compound of formula (1) may be also prepared according to the following Preparation.

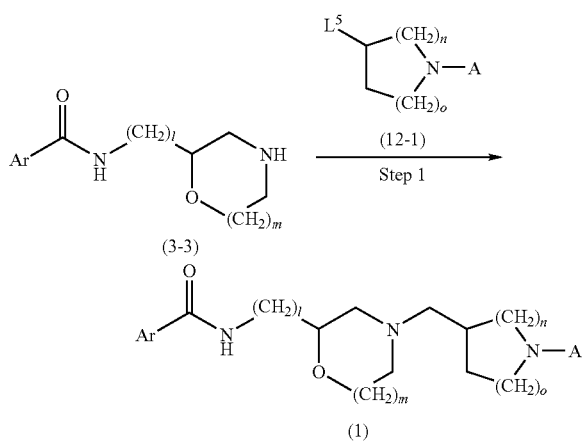

In the above scheme, Ar, A, l, m, n, o and $L^5$ are the same as defined above.

Specifically, a compound of formula (1) may be prepared by reacting a compound of formula (3-3) of the above Preparation 3 with a compound of formula (12-1). The reaction may be carried out in a similar manner to the step 2 in the above Preparation 2 and the step 9 in the above Preparation 3.

A compound of formula (12-1) may be prepared according to the following Preparation. Specifically, a compound of formula (12-3) may be treated according to methods described in the above Preparations 2 and 3 to give a compound of formula (12-1) via a compound of formula (12-7).

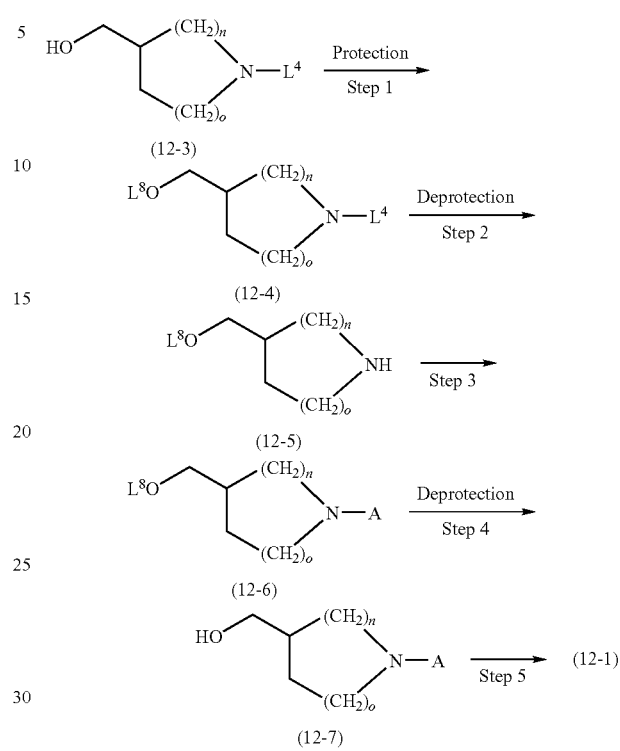

In the above scheme, A, n, o and $L^4$ have the same meanings as defined above, and $L^8$ is a protective group.

A compound of formula (12-3) is commercially available, or may be prepared according to known methods. Protection and deprotection reactions of the step 1, 2 and 4 may be carried out according to the above Preparation 2, 1). A protective group $L^4$ should be selected so as to be deprotected under different conditions from that of a protective group $L^8$.

In the step 3, a compound of formula (12-5) is reacted under a similar condition to that described in the above Preparations 1 to 9 to give a compound of formula (12-6).

A compound of formula (12-7) may be treated according to methods described in the above Preparations 2 and 3 to give a compound of formula (12-1).

A compound of formula (1) wherein A is —$CSR^7$, —$COOR^7$ or —CO—$COR^7$ may be prepared in a similar manner to Preparation 1.

A compound of formula (1) wherein A is —CO—$COOR^8$ may be prepared in a similar manner to Preparation 1 or a method described in Example 110.

A compound of formula (1) wherein A is —$CONR^9$—$OR^{10}$ may be prepared in a similar manner to Preparation 1 or a method described in Example 205.

A compound of formula (1) may be obtained in the form of a free base or an acid addition salt depending on selections or reaction or treatment conditions of starting compounds, etc. The acid addition salt may be converted into a free base by a conventional method, for example treatment with a base such as alkali carbonate or alkali hydroxide. On the other hand, the free base may be converted into an acid addition salt by a conventional method, for example treatment with various acids.

A protection or deprotection technique may be applied to a compound of formula (1) or an intermediate thereof which has a functional group such as amino, carboxy, hydroxy or oxo, as needed. A preferable protective group and a preferable method for protection and deprotection may include a method described in the above Preparation 2, 1) as well as a conventional method in the field of chemistry, particularly peptide chemistry. For example, see "Protective Groups in Organic Chemistry, T. W. Greene, Wiley-Interscience, New York, 2nd edition, 1991", in detail. The present invention also encompasses a compound of formula (1) or an intermediate thereof which is protected by a protective group.

A compound of formula (1) or an intermediate for preparing the same may be purified according to a method known to those skilled in the art. For example, it may be isolated and/or purified by column chromatography (e.g., silica gel column chromatography or ion-exchange column. chromatography), recrystallization or reprecipitation, etc.

A compound of formula (1) which has one or more asymmetric centers may be prepared by starting from any starting compounds with the corresponding asymmetric centers, or introducing asymmetric centers in any middle steps of a series of reaction steps according to a conventional method. For example, optical isomers may be obtained by starting from any optically-active starting materials, or optically resolving in an appropriate step of preparation. The optical resolution may be carried out by a diastereomer method wherein a compound of formula (1) or an intermediate thereof with a basic group is treated with an optically-active acid such as mandelic acid, N-benzyloxyalanine, lactic acid, tartaric acid, o-diisopropylidene tartaric acid, malic acid, camphorsulfonic acid or bromocamphorsulfonic acid to form a salt in an appropriate solvent. The optical resolution may be also carried out by treating a compound of formula (1) or an intermediate thereof with an acidic group with an optically-active base such as a-phenethylamine, quinine, quinidine, cinchonidine, cinchonine or strychnine to form a salt. The optically-resolved salt may be treated with an acid or a base in a conventional manner to give a compound of formula (1).

A compound of formula (1) or a pharmaceutically acceptable salt thereof shows an agonistic effect on serotonin 4 receptors, and is useful as an active ingredient of a pharmaceutical composition.

Pharmacological test results of typical compounds in the present invention are shown below.

Test Example 1

Serotonin 4 (5-HT$_4$) Receptor Binding Assay

5-HT$_4$ receptor binding assay and preparations of receptor membrane preparations were carried out according to a method of Grossman et al. [see British J. Pharmacol., (1993) 109, 618].

Slc-Hartley guinea pigs (body weight 300 to 400 g) were decapitated to remove brain rapidly, and striatum was isolated. To the obtained tissues were added fifteenfold of Hepes buffer (50 mM, pH7.4, 4° C.), and the mixture was homogenized by Teflon® homogenizer and centrifuged at 48,000×g (4° C.) for 15 minutes. To the resulting precipitate was added Hepes buffer (1 ml) to 30 mg by wet weight of tissues, and the mixture was suspended to give receptor membrane preparations.

0.1 nM [$^3$H]-GR113808 {chemical name: [1-[2-(methylsulfonylamino)ethyl]-4-piperidinyl]methyl 1-methylindole-3-carboxylate}, receptor membrane preparations, and Hepes buffer (50 mM, pH7.4, 4° C., 1 ml) containing test compounds or 30 µM serotonin were placed in an assay tube, and incubated at 37° C. for 30 minutes. On quenching the reaction, the mixture was rapidly filtered on whatman GF/B filter, which was presoaked in 0.1% polyethyleneimine for 1 hour, by using Brandel cell Harvester, and washed with ice-cooled 50 mM Tris-HCl (pH7.7, 4 ml) three times. To the filter after filtration was added ACS II scintillator, and then a radioactivity was determined by a liquid scintillation counter.

50% inhibition concentrations (IC$_{50}$) were determined from inhibition rates of test compounds to specific bindings which were obtained by subtracting nonspecific bindings from total binding amounts of [$^3$H]-GR113808. Table 1 shows results of serotonin 4 (5-HT$_4$) receptor binding assay. The term "test compound" in Table means the following Example number.

TABLE 1

| Test Compound | IC$_{50}$ (nM) |
|---|---|
| 47 | 8.04 |
| 52 | 1.94 |
| 53 | 1.46 |
| 54 | 5.91 |
| 56 | 2.90 |
| 57 | 1.82 |
| 58 | 1.97 |
| 59 | 2.83 |
| 60 | 1.86 |
| 61 | 3.70 |
| 62 | 2.51 |
| 63 | 8.60 |
| 72 | 9.04 |
| 89 | 7.33 |
| 90 | 6.98 |
| 93 | 9.36 |
| 94 | 11.85 |
| 98 | 9.62 |
| 102 | 6.79 |
| 106 | 6.12 |
| 107 | 3.43 |
| 112 | 3.01 |
| 113 | 2.23 |
| 114 | 2.22 |
| 115 | 2.48 |
| 116 | 0.68 |
| 117 | 0.04 |
| 118 | 1.70 |
| 119 | 2.05 |
| 120 | 2.63 |
| 121 | 0.23 |
| 122 | 0.87 |
| 123 | 2.11 |
| 124 | 1.95 |
| 125 | 3.51 |
| 126 | 2.32 |
| 131 | 6.96 |
| 134 | 1.50 |
| 135 | 6.04 |
| 136 | 4.26 |
| 138 | 2.80 |
| 140 | 2.84 |
| 157 | 5.54 |
| 158 | 2.80 |
| 159 | 3.53 |
| 162 | 7.90 |
| 163 | 6.58 |
| 164 | 7.50 |
| 166 | 6.93 |
| 167 | 6.36 |
| 168 | 5.17 |
| 169 | 6.09 |
| 170 | 5.65 |
| 171 | 2.16 |
| 172 | 0.87 |
| 174 | 8.52 |
| 175 | 6.13 |
| 176 | 0.72 |
| 177 | 1.62 |

TABLE 1-continued

| Test Compound | IC$_{50}$ (nM) |
|---|---|
| 178 | 1.24 |
| 194 | 10.14 |
| 198 | 25.85 |
| 201 | 4.45 |
| 202 | 4.52 |
| 206 | 10.63 |
| 208 | 4.79 |
| 220 | 25.85 |
| 221 | 45.2 |
| 222 | 17.2 |
| 223 | 18.6 |
| 224 | 14.5 |
| 225 | 20.2 |
| 226 | 21.2 |
| 227 | 6.2 |
| 228 | 13.1 |
| 229 | 18.1 |
| 230 | 0.64 |
| 231 | 9.18 |
| 232 | 7.34 |
| 233 | 12.1 |
| Cisapride | 23.0 |

Test Example 2

Mouse Defecation Assay

Male Slc-ddy mice (body weight 25 to 30 g) were used and allowed to ingest food and water ad libitum until commencement of experiments.

A group of 25 mice was divided into 5 groups, which 5 mice each per group were respectively transferred to fasting cages to adjust to new environments for about 1 hour. Then, each mouse was orally administered 3 mg/kg suspension of a test compound in 0.5% tragacanth solution to measure each stool weight of each group 30, 60, and 120 minutes after oral administration. Results of mouse defecation assay are shown in Table 2. The term "test compound" in Table means the following Example number.

Efficacies were evaluated by Dunnett assay between test compounds and control.

−: No Effect, +: Moderately Improved (p<0.05), ++: Significantly Improved (p<0.01)

TABLE 2

| Test Compound | Effect |
|---|---|
| 52 | − |
| 54 | + |
| 58 | + |
| 72 | ++ |
| 80 | + |
| 88 | ++ |
| 89 | + |
| 92 | + |
| 94 | ++ |
| 100 | ++ |
| 115 | + |
| 116 | + |
| 119 | + |
| 121 | ++ |
| 122 | + |
| 124 | + |
| 125 | ++ |
| 132 | ++ |
| 135 | ++ |
| 138 | ++ |

TABLE 2-continued

| Test Compound | Effect |
|---|---|
| 166 | ++ |
| 169 | ++ |
| 182 | ++ |
| 197 | ++ |
| 198 | ++ |
| 207 | ++ |
| 220 | ++ |
| 221 | ++ |
| 222 | ++ |
| 223 | ++ |
| 224 | ++ |
| 225 | ++ |
| 226 | ++ |
| 227 | ++ |
| 228 | ++ |
| 229 | ++ |
| 230 | ++ |
| 231 | ++ |
| 232 | ++ |
| 233 | ++ |
| Cisapride | − |

Test Example 3

Electrocardiographic Assay for Guinea Pig

Male Slc-Hartley guinea pigs were anesthetized to determine electrocardiogram (lead II) under artificial respiration. A drug solution was continuously and intravenously infused via cannula indwelled in cervical veins at a flow rate: 0.2 ml/kg/min for 15 minutes. Table 3 shows doses extending 5% of QTc (ED$_{5\%}$). The term "test compound" in Table means the following Example number.

TABLE 3

| Test Compound | ED$_{5\%}$ (mg/kg, i.v.) |
|---|---|
| 72 | >30 |
| 80 | >30 |
| 92 | >30 |
| 94 | >30 |
| 100 | >30 |
| 116 | >30 |
| 119 | >30 |
| 121 | >30 |
| 122 | >30 |
| 124 | >30 |
| 125 | >30 |
| 132 | >30 |
| 135 | >30 |
| 166 | >30 |
| 169 | >30 |
| 182 | >30 |
| 197 | >30 |
| 198 | >30 |
| 207 | >30 |
| 220 | >30 |
| 221 | >30 |
| 222 | >30 |
| 224 | >30 |
| 225 | >30 |
| 226 | >30 |
| 228 | >30 |
| 229 | >30 |
| Cisapride | 0.3 |

As is obvious from the above Tests, a compound of formula (1) or a pharmaceutically acceptable salt thereof may be used as a highly safety 5-HT$_4$ receptor agonist for treating or preventing diseases or disorders resulting from lacks of stimuli of 5-HT$_4$ receptors, since it shows (1) a strong affinity for 5-HT$_4$ receptors, (2) a gastrointestinal prokinetic activity such as a strong defecation improvement effect in oral administration, and (3) no effect on the heart (QTc extension).

Specifically, said diseases or disorders include the following conditions of (i) to (v):

(i) digestive system diseases, including an irritable bowel syndrome, an atonic constipation, a habitual constipation, a chronic constipation, a constipation induced by drug such as morphine or an antipsychotic agent, a constipation associated with Parkinson disease, a constipation associated with multiple sclerosis, a constipation associated with diabetes, or a constipation or defecation disorder by contrast agents (as a pretreatment of endoscopy or barium enema X-ray examination);

(ii) digestive system diseases, including functional dyspepsia, acute-chronic gastritis, reflux esophagitis, gastric ulcer, duodenal ulcer, gastric neurosis, postoperative paralytic ileus, senile ileus, non-diffuse gastroesophageal reflux disease, NSAID ulcer, diabetic gastroparesis, post-gastrectomy syndrome, or pseudo-bowel obstruction;

(iii) digestive system diseases, including digestive system diseases described in the above (i) and (ii), scleroderma, diabetes, anorexia in esophagus-biliary diseases, nausea, vomiting, abdomen enlarged feeling, upper abdominal discomfort, abdominal pains, heartburn, or eructations;

(iv) neuropsychiatric diseases, including schizophrenia, Alzheimer disease, depression, memory disorder, or anxiety; or (v) urinary system diseases associated with dysuria by urinary obstruction or enlarged prostate.

The compound of the present invention may be used for treating and preventing the above diverse diseases, particularly digestive system diseases, or various functional gastrointestinal disorders associated with treatment of the above diverse diseases. In other words, the compound of the present invention is useful as an enterokinesis-promoting agent or a digestive tract function-improving agent with strong defecation improving effects, particularly a therapeutic or preventive agent for the above diseases of (1), due to its significant locomotor stimulant effect on the gastrointestinal tract, particularly a lower digestive tract of colon or rectum.

The "preventive agent" used herein refers to an agent for preventing patients who do not suffer from diseases or do not have poor health at the time of administration from affecting with diseases, or for preventing symptoms thereof from worsening. Particularly, "preventing" is expected to be appropriate to a person who has had previous diseases or who has an increasing risk of affecting with diseases.

An administration route of a compound of formula (1) or a pharmaceutically acceptable salt thereof may be oral, parenteral or rectal administration, but it is not limited thereto. A dosage depends on types of compounds, administration methods, conditions or ages of patients, usually in the range of 0.01 to 30 mg/kg/day, preferably 0.05 to 10 mg/kg/day. The frequency of administration is one or more times a day, for example 1, 2 or 3 doses each time.

A preparation for oral administration may include tablet, capsule, granule, powder, syrup, subtle granule, liquid, suspension, etc., and a preparation for parenteral administration may include a formulation for injection, drop, suppository (colorectal administration), transnasal, sublingual, percutaneous absorption [lotion, emulsion, ointment, cream, jelly, gel, patch including tape, transdermal patch or poultice, or external powder], etc.

A pharmaceutical carrier includes a substance which is conventionally used in the pharmaceutical field and may not react with a compound of formula (1) or a pharmaceutically acceptable salt thereof. Specifically, a pharmaceutical composition comprising a compound of formula (1) or a pharmaceutically acceptable salt thereof may comprise a pharmaceutical carrier such as excipient, binder, lubricant, stabilizer, disintegrant, buffer, solubilizing agent, tonicity agent, solubilizing agent, pH regulator, surfactant, emulsion, suspension, dispersant, anti-setting agent, thickener, viscosity modifier, gelator, soothing agent, preservative, plasticizer, transdermal enhancing agent, antioxidant, humectant, antiseptic, perfume, and two or more pharmaceutical carriers may be also optionally selected among them.

A pharmaceutical carrier specifically includes lactose, inositol, glucose, sucrose, fructose, mannitol, dextran, sorbitol, cyclodextrin, starch (potato starch, cornstarch, amylopectin, etc.), partly pregelatinized starch, saccharose, magnesium aluminometasilicate, synthetic aluminum silicate, sodium alginate, crystalline cellulose, carboxymethylcellulose sodium, hydroxypropyl starch, carboxymethylcellulose calcium, ion-exchange resin, methylcellulose, gelatin, gum arabic, pullulan, hydroxypropylcellulose, low-substituted hydroxypropylcellulose, hydroxypropylmethylcellulose, carboxymethylcellulose, hydroxyethylcellulose, polyvinylpyrrolidone, polyvinyl alcohol, gelatin, alginic acid, sodium alginate, light anhydrous silicic acid, magnesium stearate, calcium stearate, aluminum stearate, cetostearyl alcohol, wax, paraffin, talc, tragacanth, bentonite, VEE-GUM®, carboxyvinylpolymer, titanium oxide, fatty acid ester, sorbitan fatty acid ester, sodium lauryl sulfate, glycerin, glycerin fatty acid ester, purified lanolin, glycerogelatin, polysorbate, macrogol, squalane, silicone oil, vegetable oil (sesame oil, olive oil, soy oil, cotton oil, castor oil, etc.), liquid paraffin, soft paraffin, white vaseline, yellow vaseline, paraffin, wool fat, wax (bees wax, carnauba wax, bleached wax, etc.), water, propylene glycol, polyethylene glycol, glycerol, lauryl alcohol, myristyl alcohol, oleyl alcohol, cetyl alcohol, ethanol, sodium chloride, sodium hydroxide, hydrochloric acid, citric acid, lauric acid, myristic acid, stearic acid, oleic acid, benzylalcohol, glutamic acid, glycine, methyl paraoxybenzoate, propyl paraoxybenzoate, p-hydroxybenzoic acid ester, cholesterol ester, ethylene glycol monoalkyl ester, propyleneglycol monoalkyl ester, glyceryl monostearate, sorbitan fatty acid ester, isopropyl myristate, isopropyl palmitate, carboxypolymethylene, saccharin, strawberry flavor, peppermint flavor, cacao butter, polyisobutylene, vinyl acetate copolymer, acrylic copolymer, triethyl citrate, acetyl triethyl citrate, diethyl phthalate, diethyl sebacate, dibutyl sebacate, acetylated monoglyceride, diethylene glycol, dodecylpyrrolidone, urea, ethyl laurate, azone, kaolin, bentonite, zinc oxide, agarose, carrageenan, acacia gum, xanthan gum, potassium laurate, potassium palmitate, potassium myristate, sodium cetylsulfate, castor oil sulfoxide (turkey red oil), Span (sorbitan stearate, sorbitan monooleate, sorbitan sesquioleate, sorbitan trioleate, etc.), Tween (polysorbate 20, polysorbate 40, polysorbate 60, polysorbate 65, polysorbate 80, polysorbate 85, polyoxyethylene sorbitan fatty acid ester, etc.), polyoxyethylene hydrogenated castor oil (so-called HCO), polyoxyethylene lauryl ether, polyoxyethylene cetyl ether, polyoxyethylene oleyl ether, polyethylene glycol monolaurate, polyethylene glycol monostearate, poloxamer (so-called Pluronice®), lecitin (including a purified phospholipid isolated from lecitin such as phosphatidylcholine or phosphatidylserine), a hydrogen additive of lecitin, etc.

A compound of formula (1) or a pharmaceutically acceptable salt thereof for the above pharmaceutical use may be usually administered in the form of a formulation prepared by mixing with a pharmaceutical carrier according to a conventional method. For example, a pharmaceutical composition may comprise a compound of formula (1) or a pharmaceutically acceptable salt thereof as the active ingredient in the range of 0.01 to 99% by weight, preferably 0.05 to 80% by weight, more preferably 0.1 to 70% by weight, more preferably 0.1 to 50% by weight. The formulation may further comprise a therapeutically effective additive.

The present invention includes a combination therapy for diseases disclosed herein wherein a compound of formula (1), a pharmaceutically acceptable salt thereof, or a pharmaceutical composition comprising the same is sequentially or simultaneously administered in combination with one or more other agents as below.

Specifically, the other agents for digestive system diseases associated with constipation include a saline purgative such as magnesium sulfate, magnesium oxide or magnesium citrate, an invasive purgative such as dioctyl sodium sulfosuccinate or casanthranol, a distensible purgative such as carmellose, a colon-irritant purgative such as bisacodyl, picosulfate, senna or sennoside, a small intestine-irritant purgative such as castor oil, an intestinal lavage solution such as Magcorol® or Niflec®, etc.

The other agents for digestive system diseases such as functional dyspepsia, acute-chronic gastritis, reflux esophagitis, non-diffuse gastroesophageal reflux disease, diabetic gastroparesis, gastric ulcer, duodenal ulcer, NSAID ulcer, gastric neurosis, postoperative paralytic ileus, senile ileus, postgastrectomy syndrome, or pseudo-bowel obstruction include a proton pump inhibitor such as omeprazole, rabeprazole or lansoprazole, an antacid such as a histamine $H_2$ receptor inhibitor including cimetidine, ranitidine or famotidine, a digestive tract functional regulator such as mosapride or domperidone, a gastric mucosa-protective agent, an antiflatulent, etc. The other agents for depression or anxiety include an antidepressant or antianxiety drug including a selective serotonin reuptake inhibitor (SSRI) such as paroxetine or sertraline, a serotonin-norepinephrine reuptake inhibitor (SNRI) such as venlafaxine or duloxetine, a tricyclic antidepressant such as amitriptyline or imipramine, a tetracyclic antidepressant such as mianserin or maprotiline, etc. The other agents for memory disorder include a cholinesterase inhibitor such as donepezil or rivastigmine, an impaired cognition improving agent such as memantine, etc. The other agents for dysuria associated with prostatic hyperplasia include a therapeutic agent for dysuria such as tamsulosin or terazosin, etc.

The present invention is specifically illustrated by the following Reference Examples and Examples, but is not limited thereto. Obtained compounds were identified by element assay, mass spectrum, IR spectrum, liquid chromatography mass spectrometry (LC-MS), hydrogen nuclear magnetic resonance spectroscopy ($^1$H-NMR spectrum), powder X-ray diffraction measurement (XRD), etc. A powder X-ray diffraction measurement was carried out by using X'Pert Pro manufactured by Spectris Co., Ltd. under conditions of CuKα1 ray (wave length: 1.54060 angstrom) in the range of diffraction angles of 2θ4° to 65°, X-ray tube current: 40 milliamperes, voltage: 45 kilovolts, step: 0.01700° and measurement time: 101.41770 seconds/step.

The following abbreviations may be also used for the simplification in the following Reference Examples and Examples.

Me: methyl, Et: ethyl, Pr: propyl, $^i$Pr: isopropyl, Bu: butyl, $^i$Bu: isobutyl, $^t$Bu: tert-butyl, Ph: phenyl, Ac: acetyl, Boc: tert-butoxycarbonyl, THF: tetrahydrofuran, E: ethanol, M: methanol, IP: isopropanol, A: acetone, H: hexane, DE: diethylether, EA: ethyl acetate, DIP: diisopropyl ether, AN: acetonitrile, DMF: N,N-dimethylformamide, TEA: triethylamine, s: singlet, d: doublet, t: triplet, q: quartet, quint: quintet, dd: double doublet, td: triple doublet, ddd: tetra doublet, sex: sextet, m: multiplet, br s: broad singlet, br d: broad doublet, br t: broad triplet, br q: broad quartet, br dd: broad double doublet, J: coupling constant.

EXAMPLES

Reference Example 1

Preparation of 1-(tert-butoxycarbonyl)-3-[(p-toluenesulfonyloxy)methyl]azetidine

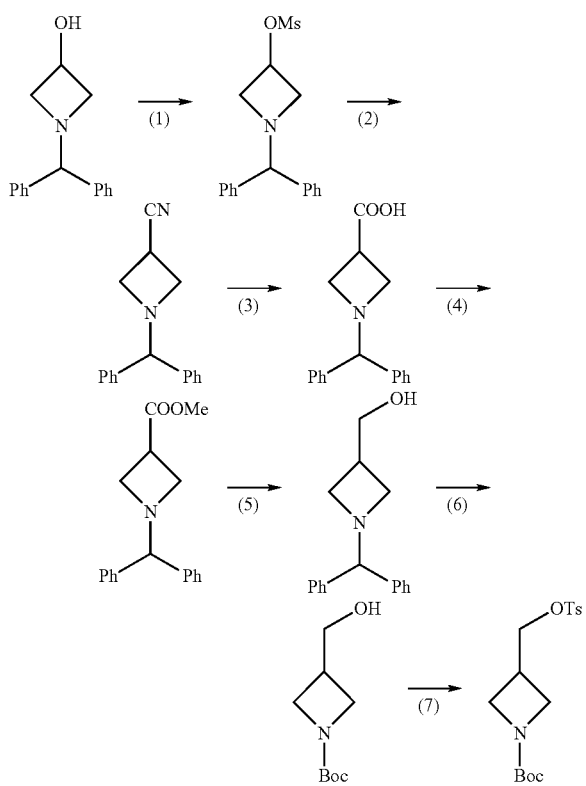

(1) To a solution of 1-diphenylmethyl-3-hydroxyazetidine (1.0 g) and TEA (1.11 ml) in methylene chloride (5 ml) was added dropwise a solution of methanesulfonyl chloride (0.72 g) in methylene chloride (5 ml) over 20 minutes under ice-cooling. After the addition, the reaction solution was allowed to warm to room temperature, and stirred for 2 hours. To the reaction solution was added water, and the mixture was extracted with chloroform. The extract was sequentially washed with water and brine, then dried over anhydrous magnesium sulfate, and the solvent was removed in vacuo. The residue was purified by silica gel column chromatography (eluent: hexane to hexane/ethyl acetate=7/3) to give 1-diphenylmethyl-3-methanesulfonyloxyazetidine (1.0 g) as a white powder.

$^1$H-NMR (CDCl$_3$, δppm); 2.98 (3H, s), 3.14-3.25 (2H, m), 3.59-3.68 (2H, m), 4.40 (1H, s), 5.10 (1H, quint, J=5.9 Hz), 7.15-7.3, 7.3-7.4 (10H, m). LC-MS, m/z; 318 (MH$^+$).

(2) A mixture of the above product (0.77 g), sodium cyanide (0.18 g) and DMF (7 ml) was warmed to 70° C. for 7 hours with stirring. To the reaction solution was added ice water, and the precipitated solid was filtered under reduced pressure, washed with water and dried to give 3-cyano-1-diphenylmethylazetidine (0.48 g) as a yellow powder.

$^1$H-NMR (CDCl$_3$, δppm); 3.2-3.33 (3H, m), 3.42-3.53 (2H, m), 4.36 (1H, s), 7.15-7.3, 7.3-7.45 (10H, m). LC-MS, m/z; 249 (MH$^+$).

(3) A mixture of the above product (5.79 g), sodium hydroxide (2.57 g) and 50% aqueous ethanol (50 ml) was heated to reflux for 6 hours with stirring. After cooled to 0° C., the mixture was adjusted to pH3 with concentrated hydrochloric acid, and extracted with chloroform. The extract was sequentially washed with water and brine, and then dried over anhydrous magnesium sulfate. The solvent was removed in vacuo to give 1-diphenylmethylazetidine-3-carboxylic acid (about 6.5 g) as a yellow amorphous solid. The solid was used in the next step without any purification.

(4) To a solution of the above product (about 6.5 g) in methanol (60 ml) was added concentrated sulfuric acid (6 ml), and the mixture was heated to reflux for 1 hour with stirring. After cooled to room temperature, the solvent was removed in vacuo, and the residue was dissolved in chloroform. The solution was washed with water, 5% sodium bicarbonate aqueous solution, water and brine in that order, and then dried over anhydrous magnesium sulfate. The solvent was removed in vacuo to give 1-diphenylmethylazetidine-3-carboxylic acid methyl ester (4.9 g) as a brown powder.

$^1$H-NMR (CDCl$_3$, δppm); 3.2-3.4, 3.4-3.5 (5H, m), 3.69 (3H, s), 4.39 (1H, s), 7.2-7.3, 7.3-7.45 (10H, m). LC-MS, m/z; 282 (MH$^+$).

(5) To a suspension of lithium aluminum hydride (1.32 g) in anhydrous THF (50 ml) was added dropwise a solution of the above product (4.9 g) in anhydrous THF (20 ml) at 0° C. of inside temperature over 15 minutes. After stirring for 30 minutes at the same temperature, to the reaction solution was gradually added dropwise an aqueous solution of saturated potassium sodium tartrate, and an excess amount of lithiurryaluminum hydride was degraded. Supernatant THF was filtered and the insoluble was washed with THF, and then the combined THF was dried over anhydrous magnesium sulfate and the solvent was removed in vacuo. The residue was purified by silica gel column chromatography (eluent: chloroform/methanol=97/3) to give 1-diphenylmethyl-3-azetidine -methanol (3.56 g) as a yellow oil. The oil was used in the next step without any purification.

(6) To a solution of the above product (3.74 g) in ethanol (70 ml) was added 10% palladium carbon (1.1 g), and the mixture was hydrogenated at 50° C. under normal pressure. After absorption of theoretical amount of hydrogen, the reaction solution was cooled to room temperature and filtered through Celite® to remove catalysts. To the filtrate was added di-tert-butyl dicarbonate (3.56 g), and the mixture was stirred at room temperature for 2 hours. The reaction solution was dried under reduced pressure to be solidified, and the residue was purified by silica gel column chromatography (eluent: chloroform/methanol=96/4) to give 1-(tert-butoxycarbonyl)-3-azetidine -methanol (2.66 g) as a white oil.

$^1$H-NMR (CDCl$_3$, δppm); 1.44 (9H, s), 1.7 (1H, br. s), 2.70 (1H, m), 3.69 (2H, dd, J=5.1, 8.6 Hz), 3.78 (2H, br t, J=5.1 Hz), 3.99 (2H, dd, J=8.6, 8.6 Hz). LC-MS, m/z; 188 (MH$^+$).

(7) A mixture of the above product (2.66 g), p-toluenesulfonyl chloride (2.40 g), TEA (2.98 ml), 4-dimethylaminopyridine (0.17 g) and methylene chloride (27 ml) was stirred at room temperature for 1 day. The reaction solution was dried under reduced pressure to be solidified, and to the residue was added ethyl acetate. Then, the mixture was sequentially washed with water, 30% aqueous sodium bicarbonate solution, 30% aqueous solution of citric acid, water and brine, and then dried over anhydrous magnesium sulfate. The solvent was removed in vacuo to give the titled compound (3.99 g) as a yellow oil.

$^1$H-NMR (CDCl$_3$, δppm); 1.42 (9H, s), 2.46 (3H, s), 2.85 (1H, m), 3.59 (2H, br dd, J=5.3, 8.7 Hz), 3.96 (2H, dd, J=8.7, 8.7 Hz), 4.14 (2H, d, J=7.0 Hz), 7.37 (2H, d, J=8.1 Hz), 7.80 (2H, d, J=8.1 Hz). LC-MS, m/z; 242.

Reference Example 2

Preparation of 4-amino-5-chloro-2-methoxy-N-(2-morpholinylmethyl)benzamide

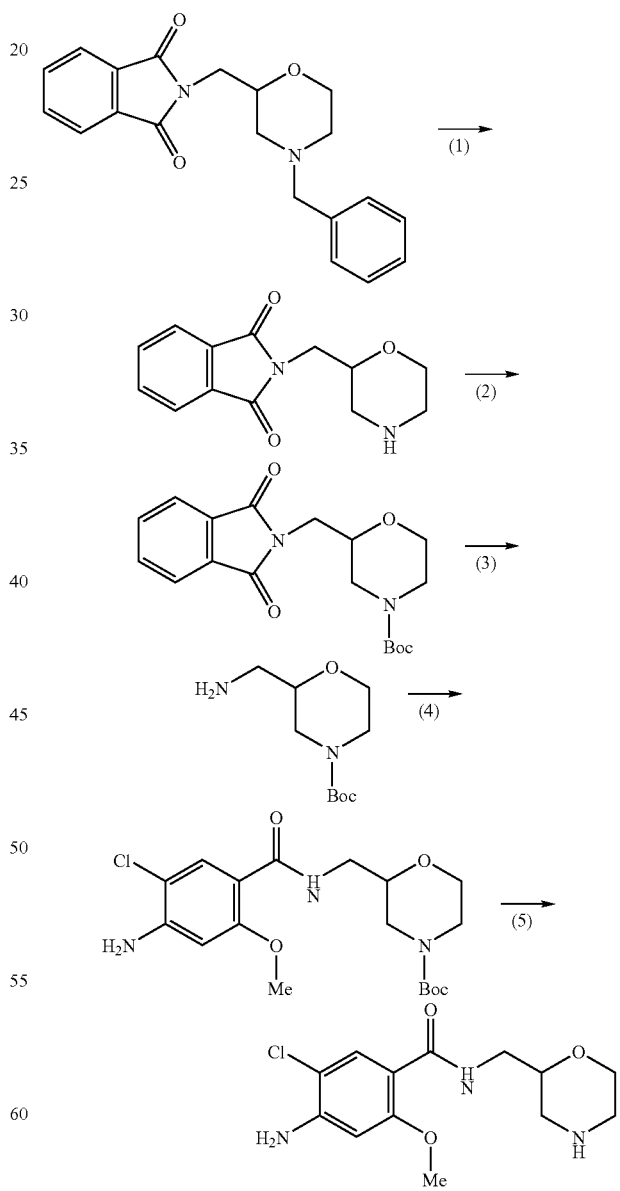

(1) To a suspension of N-[(4-benzyl-2-morpholinyl)methyl] phthalimide (S. Kato, et al., J. Med. Chem., (1990) 33, 1406-1413) (2.0 g) in 3N hydrochloric acid (48 ml), water (10 ml) and ethanol (15 ml) was added 10% palladium carbon (0.3 g), and the mixture was hydrogenated at room temperature under 4 kgf/cm$^2$ for 18 hours. After affirmation of disappearance of a starting material, the reaction solution was filtered through Celite® to remove catalysts, and the filtrate was alkalified by addition of excess amounts of potassium carbonate powder. Then; the filtrate was extracted with chloroform. The extract was dried over anhydrous magnesium sulfate, and the solvent was removed in vacuo to give N-(2-morpholinylmethyl)phthalimide (1.45 g) as a solid.

$^1$H-NMR (CDCl$_3$, δppm); 2.66 (1H, dd, J=9.5, 12.1 Hz), 2.77 (1H, br d, J=12.3 Hz), 2.86 (1H, dd, J=3.3, 14.1 Hz), 2.96 (1H, dd, J=2.0, 12.5 Hz), 3.52 (1H, td, J=2.9, 13.9 Hz), 3.63 (1H, dd, J=3.9, 16.8 Hz), 3.73-3.88 (4H, m), 7.68-7.78 (2H, m), 7.82-7.92 (2H, m). LC-MS, m/z; 247 (MH$^+$).

(2) To a solution of the above product (1.0 g) and TEA (0.41 g) in methanol (10 ml) was gradually added a solution of di-tert-butyl dicarbonate (0.98 g) in methanol (5 ml), and after completion of addition, the mixture was stirred at room temperature for 4 hours. The reaction solution was dried under reduced pressure to be solidified. The residue was dissolved in chloroform, and then sequentially washed with water and brine, and dried over anhydrous magnesium sulfate. The solvent was removed in vacuo, and the residue was purified by silica gel column chromatography (eluent: chloroform/methanol=10/1) to give N-[{4-(tert-butoxycarbonyl)-2-morpholinyl}methyl]phthalimide (1.4 g) as a white powder.

$^1$H-NMR (CDCl$_3$, δppm); 1.46 (9H, s), 2.75 (1H, br d like), 3.0 (1H, br t like), 3.45 (1H, m), 3.6-4.1 (6H, m), 7.7-7.85 (2H, m), 7.85-8.0 (2H, m). LC-MS, m/z; 247.

(3) A solution of the above product (1.4 g) and hydrazine monohydrate (0.18 g) in ethanol (10 ml) was heated to reflux for 1.5 hours with stirring. After cooling to room temperature, the solvent was removed in vacuo, and to the residue was added 30% aqueous solution of citric acid. Then, the insoluble was filtered off under reduced pressure. The filtrate was washed with chloroform, adjusted to pH10 by 2N aqueous sodium hydroxide solution, and then extracted with chloroform. The extract was washed with brine, dried over anhydrous magnesium sulfate, and then the solvent was removed in vacuo to give 2-aminomethyl-4-(tert-butoxycarbonyl)morpholine (0.34 g) as a pale yellow oil.

$^1$H-NMR (CDCl$_3$, δppm); 1.46 (9H, s), 1.8 (2H, br s), 2.55-2.85 (3H, m), 2.93 (1H, br d like), 3.37 (1H, m), 3.53 (1H, td, J=2.8, 14.4 Hz), 3.7-3.95 (3H, m). LC -MS, m/z; 217 (MH$^+$), 117.

(4) To a suspension of 4-amino-5-chloro-2-methoxybenzoic acid (0.32 g) and N,N'-carbonyldiimidazole (0.30 g) in THF (10 ml) was added a solution of the above product (0.34 g) in THF (2 ml), and the mixture was stirred at room temperature for 3 days. To the reaction solution was added water, and the mixture was concentrated in vacuo. The precipitated insoluble was filtered in vacuo, and then washed with water and dried to give 4-amino-N-[{4-(tert-butoxycarbonyl)-2-morpholinyl}methyl]-5-chloro-2-methoxybenzamide (0.5 g) as a white powder. LC-MS; m/z; 400 (MH$^+$), 300.

(5) To a solution of the above product (8.0 g) in ethanol (40 ml) was added concentrated hydrochloric acid (40 ml), and the mixture was stirred at room temperature for 1 hour. The reaction solution was concentrated in vacuo and adjusted to pH10 by 2N aqueous sodium hydroxide solution under ice-cooling, and then extracted with chloroform. The extract was washed with water, then brine, and dried over anhydrous magnesium sulfate. Then, the solvent was removed in vacuo to give the titled compound (6.0 g) as a white powder. LC-MS, m/z; 300 (MH$^+$).

Reference Example 3

Preparation of 4-amino-5-chloro-N-[(1,4-hexahydroxazepin-2-yl)methyl]-2-methoxy-benzamide

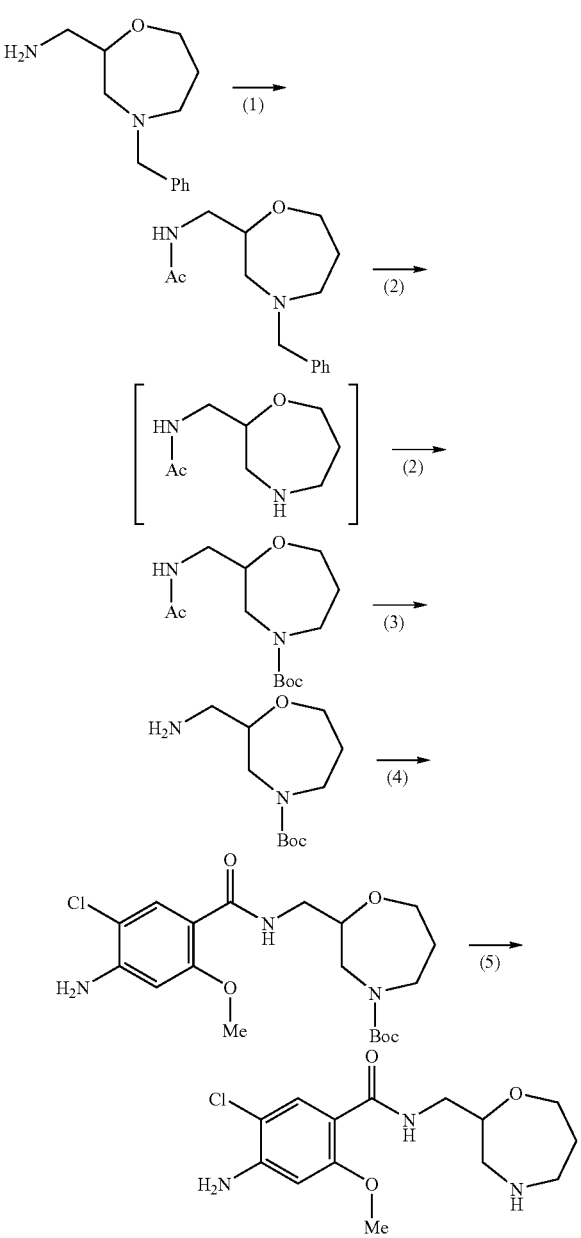

(1) To a mixed solution of 2-aminomethyl-4-benzyl-1,4-hexahydroxazepine (H. Harada, et al., Chem. Pharm, Bull., (1995) 43, 1364-1378) (1.75 g) and sodium bicarbonate (2.0 g) in methylene chloride (10 ml) and water (10 ml) was added dropwise acetyl chloride (1.73 ml) at 0° C. After completion of addition, the mixture was stirred at the same temperature for 0.5 hours. The organic layer was separated, washed with water, then brine, and dried over anhydrous magnesium sulfate, and then the solvent was removed in vacuo. The residue was purified by silica gel column chromatography (eluent: chloroform/methanol=95/5) to give 2-acetylaminomethyl-4-benzyl-1,4-hexahydroxazepine (1.66 g) as a yellow oil.

$^1$H-NMR (CDCl$_3$, δppm); 1.75-2.0 (2H, m), 1.94 (3H, s), 2.44 (1H, dd, J=5.9, 13.6 Hz), 2.55-2.8 (3H, m), 3.0 (1H, m), 3.45 (1H, m), 3.64 (2H, dd like), 3.65-3.85 (2H, m), 3.9 (1H, m), 5.75 (1H, br s), 7.2-7.45 (5H, m). LC-MS, m/z; 263 (MH$^+$).

(2) To a mixed solution of the above product (1.66 g) in ethanol (20 ml) and acetic acid (3 ml) was added 10% palladium carbon (0.5 g), and the mixture was hydrogenated at 50° C. under normal pressure. After absorption of theoretical amount of hydrogen (about 2 hours), the reaction solution was filtered through Celite® to remove catalyst. To the filtrate were added TEA (5 ml) and di-tert-butyl dicarbonate (1.60 g), and the solution was stirred at room temperature for 1 day. The reaction solution was dried under reduced pressure to be solidified. The residue was dissolved in chloroform, and then washed with water, then brine, and dried over anhydrous magnesium sulfate. The solvent was removed in vacuo to give 2-acetylaminomethyl-4-(tert-butoxycarbonyl)-1,4-hexahydroxazepine (1.68 g) as a yellow oil.

$^1$H-NMR (CDCl$_3$, δppm); 1.47 (9H, s), 1.75 (1H, m), 1.8-2.0 (2H, m), 2.00 (3H, s), 2.9-3.7 (6H, m), 3.76 (1H, dd, J=3.0, 14.4 Hz), 4.05 (1H, m), 5.85, 6.00 (1H, br s). LC-MS, m/z; 173.

(3) A solution of the above product (1.68 g) and granulated sodium hydroxide (2.23 g) in 50% aqueous ethanol (16 ml) was heated to reflux for 4 hours with stirring. After cooling to room temperature, the reaction solution was dried under reduced pressure to be solidified, and the residue was dissolved in chloroform, washed with water, then brine, and dried over anhydrous magnesium sulfate. The solvent was removed in vacuo to give 2-aminomethyl-4-(tert-butoxycarbonyl)-1,4-hexahydroxazepine (1.18 g) as a yellow oil.

$^1$H-NMR (CDCl$_3$, δppm); 1.47 (9H, s), 1.7-2.1 (3H, m), 2.7 (1H, m), 2.95 (1H, m), 3.3 (1H, m), 3.45 (2H, m), 3.7 (2H, m), 4.1 (1H, m). LC-MS, m/z; 231 (MH$^+$), 131.

(4) A mixture of the above product (1.18 g), 4-amino-5-chloro-2-methoxybenzoic acid (1.03 g), 1-ethyl-3-(3-dimethylaminopropyl)carbodiimide hydrochloride (1.28 g) and methylene chloride (10 ml) was stirred at room temperature overnight. The reaction solution was sequentially washed with water, 1N aqueous sodium hydroxide solution, water and brine, and then dried over anhydrous magnesium sulfate, and the solvent was removed in vacuo. The residue was purified by silica gel column chromatography (eluent: chloroform/methanol=99/1) to give 4-amino-N-[[4-(tert-butoxycarbonyl)-1,4-hexahydroxazepin-2-yl]methyl]-5-chloro-2-methoxybenzamide (1.24 g) as a white amorphous solid.

$^1$H-NMR (CDCl$_3$, δppm); 1.45 (9H, s), 1.75-2.05 (2H, m), 3.05 (1H, m), 3.1-3.5, 3.5-4.0 (7H, m), 3.90 (3H, s), 4.1 (1H, m), 4.40 (2H, br s), 6.29 (1H, s), 8.05 (1H, br s like), 8.10 (1H, s). LC-MS, m/z; 414 (MH$^+$), 314.

(5) In place of 4-amino-N-[{4-(tert-butoxycarbonyl)-2-morpholinyl}methyl]-5-chloro-2-methoxybenzamide in Reference Example 2(5), the above product was treated in the similar manner to Reference Example 2(5) to give the titled compound as a white powder.

$^1$H-NMR (DMSO-d$_6$, δppm); 1.7-1.8 (2H, m), 2.7 (1H, m), 2.75-3.0 (1H, m), 3.10 (1H, m), 3.35 (1H, m), 3.5-3.7 (2H, m), 3.8-4.0 (2H, m), 3.83 (3H, s), 5.94 (2H, s), 6.48 (1H, s), 7.70 (1H, s), 8.05 (1H, t like, J=5.2 Hz). LC-MS, m/z; 314 (MH$^+$).

Compounds of Reference Examples 4 to 9 were prepared in the similar manner to Reference Example 2. Each product was a white powder.

TABLE 4

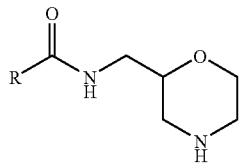

| Reference Example | Compound Name | R— | LC-MS, m/z |
|---|---|---|---|
| 4 | 4-amino-5-chloro-N-(2-morpholinylmethyl)-2-propoxybenzamide | 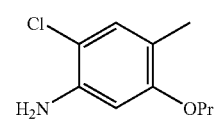 | 328 (MH$^+$) |
| 5 | 4-amino-5-chloro-2-isopropoxy-N-(2-morpholinylmethyl)benzamide | 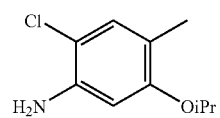 | 328 (MH$^+$) |
| 6 | 4-amino-5-chloro-N-(2-morpholinylmethyl)-2,3-dihydrobenzo[b]furan-7-carboxamide | 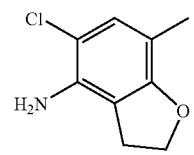 | 312 (MH$^+$) |

TABLE 4-continued

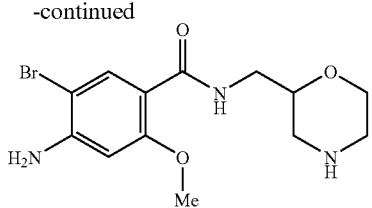

| Reference Example | Compound Name | R— | LC-MS, m/z |
|---|---|---|---|
| 7 | 2-allyloxy-4-amino-5-chloro-N-(2-morpholinylmethyl)benzamide | (Cl, H₂N, O-allyl substituted phenyl) | 326 (MH⁺) |
| 8 | 6-amino-5-chloro-2-methoxy-N-(2-morpholinylmethyl)pyridine-3-carboxamide | (Cl, H₂N, OMe substituted pyridine) | 301 (MH⁺) |
| 9 | 4-amino-5-bromo-2-methoxy-N-(2-morpholinylmethyl)benzamide | (Br, H₂N, OMe substituted pyridine) | 346 (MH⁺) |

Reference Example 9 (Alternative Method)

Preparation of 4-amino-5-bromo-2-methoxy-N-(2-morpholinylmethyl)benzamide

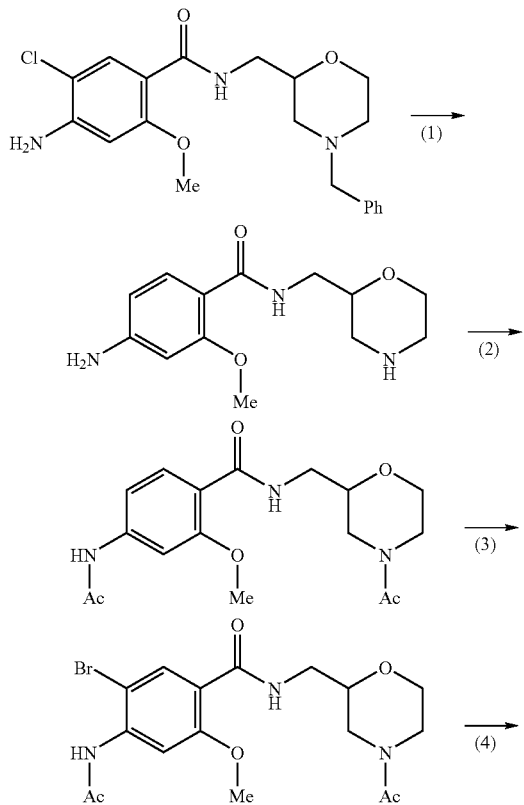

(1) 4-Amino-N-[(4-benzyl-2-morpholinyl)methyl]-5-chloro-2-methoxybenzamide (S. Kato, et al., J. Med. Chem., (1990) 33, 1406-1413) (45.0 g) was dissolved in a mixed solvent of ethanol (650 ml), acetic acid (100 ml) and water (50 ml), and then thereto was added 10% palladium carbon (4 g). The mixture was hydrogenated at about 50° C. under normal pressure. After absorption of theoretical amount of hydrogen (about 3 hours), the reaction solution was cooled to room temperature and filtered through Celite® to remove catalysts. The filtrate was concentrated in vacuo, and alkalified with 30% aqueous potassium hydroxide solution. Then, the precipitated powder was filtered in vacuo, washed with water and dried to give 4-amino-2-methoxy-N-(2-morpholinylmethyl)benzamide (23.2 g). LC-MS, m/z; 266 (MH⁺).

(2) To a suspension of the above product (48.5 g) in methanol (400 ml) was added acetic anhydride (52.8 g), and the mixture was stirred at room temperature for 3 hours. The solvent was removed in vacuo, and the residue was dissolved in water, alkalified with 30% aqueous potassium hydroxide solution under ice-cooling, and then extracted with chloroform. The extract was washed with water, then brine, and dried over anhydrous magnesium sulfate. The solvent was removed in vacuo to give N-[(4-acetyl-2-morpholinyl)methyl]-4-acetylamino-2-methoxybenzamide (50.0 g) as a light brown amorphous solid. LC-MS, m/z; 350 (MH⁺).

(3) A solution of the above product (50.0 g) and N-bromosuccinic imide (24.4 g) in DMF (300 ml) was stirred at 70°

C. for 1 hour. After cooling to room temperature, the reaction solution was dried under reduced pressure to be solidified, and then to the residue was added water. The precipitated crystal was filtered in vacuo to give white N-[(4-acetyl-2-morpholinyl)methyl]-4-acetylamino-5-bromo-2-methoxybenzamide. The crystal was used in the next step without dryness. LC-MS, m/z; 430 (MH⁺).

(4) To the above compound was added 10% hydrochloric acid (360 ml), and the suspension was heated to reflux for 3 hours with stirring. The reaction solution was ice-cooled, and then alkalified with 30% aqueous potassium hydroxide solution and extracted with chloroform. The extract was washed with water, then brine, and dried over anhydrous magnesium sulfate. Then, the solvent was removed in vacuo to give the titled compound (25.0 g) as a white powder.

The following compounds of Reference Examples 10 to 11 were prepared in the similar manner to Reference Example 9 (Alternative Method). Each product was a white powder.

TABLE 5

| Reference Example | Compound Name | R— | LC-MS, m/z |
|---|---|---|---|
| 10 | 6-amino-5-bromo-2-methoxy-N-(2-morpholinyl-methyl)pyridine-3-carboxamide | Br, H₂N—pyridine—OMe | 347 (MH⁺) |
| 11 | 4-amino-5-bromo-2-ethoxy-N-(2-morpholinyl-methyl)benzamide | Br, H₂N—phenyl—OEt | 360 (MH⁺) |

Reference Example 12

Preparation of 2-aminomethyl-4-[1-(tert-butoxycarbonyl)-4-piperidinyl)methyl]morpholine

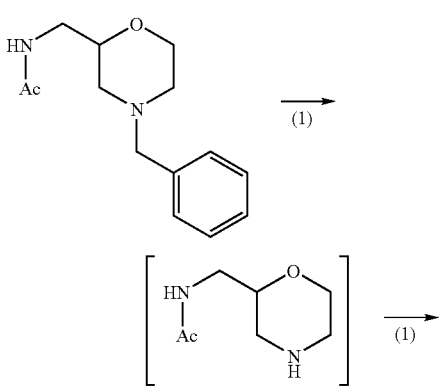

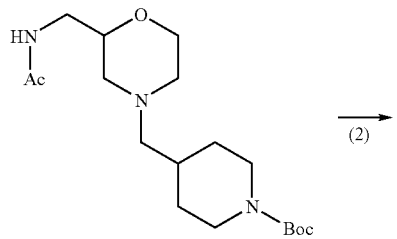

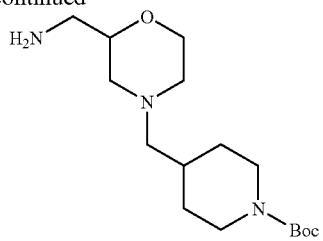

(1) To a solution of 2-acetylaminomethyl-4-benzylmorpholine (S. Kato, et al., J. Med. Chem., (1990) 33, 1406-1413) (56.2 g) in ethanol (800 ml), acetic acid (80 ml) and water (20 ml) was added 10% palladium carbon (6 g), and the mixture was hydrogenated at about 50° C. under normal pressure. After absorption of theoretical amount of hydrogen, the reaction solution was cooled to room temperature and filtered through Celite® to remove catalysts. The filtrate was removed in vacuo. To the colorless oily residue containing 2-acetylaminomethylmorpholine were added 1-(tert-butoxycarbonyl)-4-[(p-toluenesulfonyloxy)methyl]piperidine (83.7 g), anhydrous potassium carbonate (156.6 g), potassium iodide (5 g) and acetonitrile (1500 ml), and the mixture was heated to reflux with stirring for 1 day. After cooling to room temperature, the reaction solution was dried under reduced pressure to be solidified, and the residue was dissolved in chloroform. The solution was washed with water, then brine, and then dried over anhydrous magnesium sulfate. The solvent was removed in vacuo, and the residue was purified by silica gel column chromatography (eluent: ethyl acetate to ethyl acetate/methanol=9/1) to give 2-acetylaminomethyl-4-[{1-(tert-butoxycarbonyl)-4-piperidinyl}methyl]morpholine (58.5 g) as a fawn oil. LC-MS, m/z; 356 (MH$^+$).

(2) To a solution of the above product (46.8 g) in ethanol (300 ml) was added aqueous potassium hydroxide solution (potassium hydroxide (73.3 g)/water (500 ml)), and the mixture was heated to reflux with stirring for 62 hours. After cooling to room temperature, the solvent was removed in vacuo, and the residue was dissolved in chloroform. The solution was washed with water, then brine, and then dried over anhydrous magnesium sulfate. The solvent was removed in vacuo to give the titled compound (39.3 g) as a pale yellow oil.

$^1$H-NMR (CDCl$_3$, δppm); 0.95-1.25 (3H, m), 1.46 (9H, s), 1.5-1.8 (5H, m), 2.0-2.2 (3H, m), 2.6-2.8 (6H, m), 3.45 (1H, m), 3.65 (1H, td, J=2.4, 13.7 Hz), 3.86 (1H, d like, J=9.7 Hz), 4.07 (2H, br d). LC-MS, m/z; 314 (MH$^+$).

Reference Example 12 (Alternative Method 1)

Preparation of 2-aminomethyl-4-[{1-(tert-butoxycarbonyl)-4-piperidinyl}methyl]morpholine

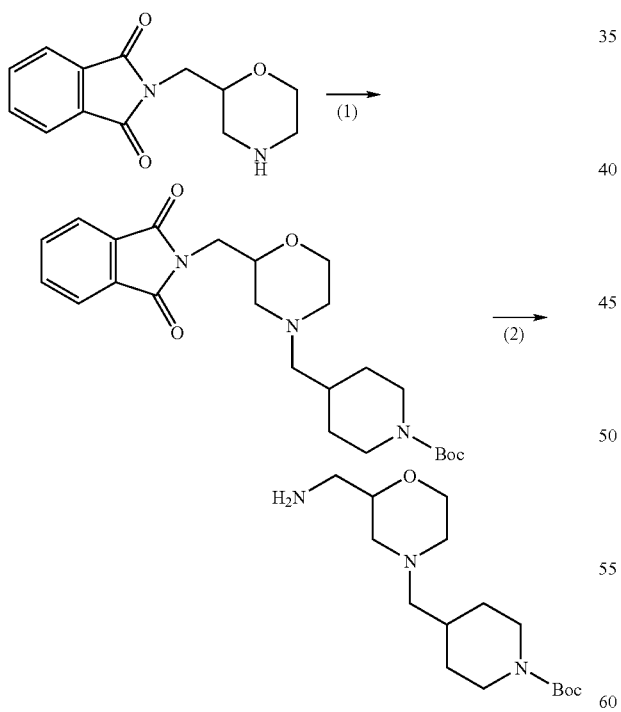

(1) A mixture of N-(2-morpholinylmethyl)phthalimide (Reference Example 2(2)) (1.5 g), 1-(tert-butoxycarbonyl)-4-[(p-toluenesulfonyloxy)methyl]piperidine (2.15 g), anhydrous potassium carbonate (2.52 g), potassium iodide (0.91 g) and acetonitrile (35 ml) was heated to reflux with stirring overnight. After cooling to room temperature, the reaction solution was dried under reduced pressure to be solidified, and the residue was dissolved in ethyl acetate. The solution was washed with water, then brine, and then dried over anhydrous magnesium sulfate. The solvent was removed in vacuo to give N-[{4-[(1-(tert-butoxycarbonyl)-4-piperidinyl)methyl]-2-morpholinyl}methyl]phthalimide (1.75 g) as a white solid.

$^1$H-NMR (CDCl$_3$, δppm); 0.9-1.15 (2H, m), 1.45 (9H, s), 1.5-1.8 (3H, m), 1.98 (1H, t, J=10.1 Hz), 2.16 (3H, d like, J=6.8 Hz), 2.5-2.85 (4H, m), 3.5-3.8 (2H, m), 3.8-4.9 (3H, m), 4.1 (2H, br s), 7.6-7.8 (2H, m), 7.8-7.9 (2H, m). LC-MS, m/z; 444 (MH$^+$).

(2) In place of N-[{4-(tert-butoxycarbonyl)-2-morpholinyl}methyl]phthalimide in Reference Example 2(3), the above product was treated in the similar manner to Reference Example 2(3) to give the titled compound as a pale yellow oil.

Reference Example 12 (Alternative Method 2)

Preparation of 2-aminomethyl-4-[{1-(tert-butoxycarbonyl)-4-piperidinyl}methyl]morpholine

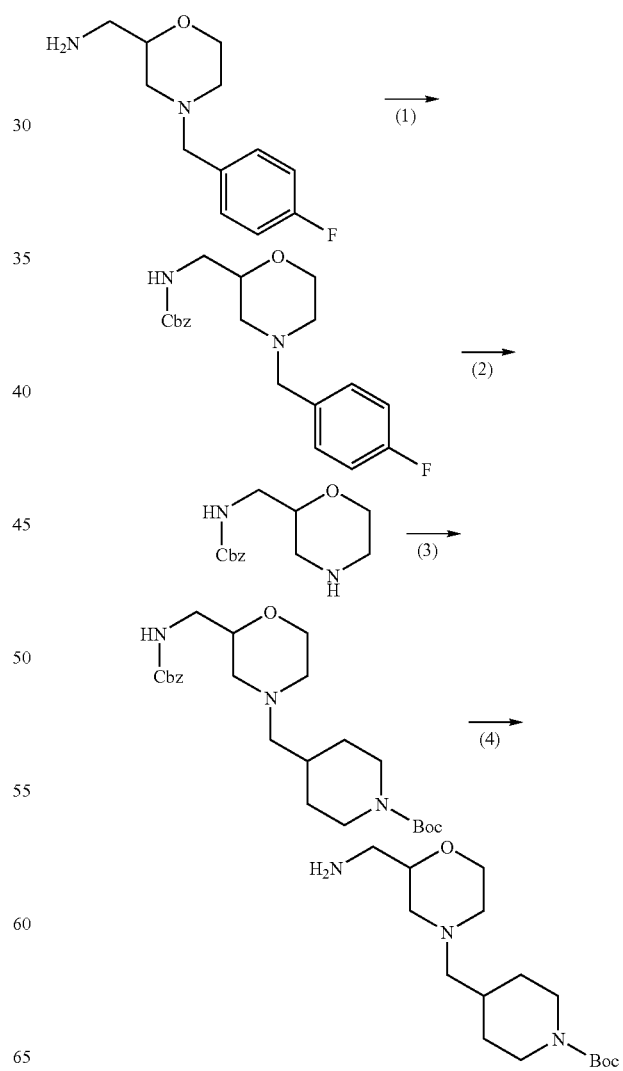

(1) To a mixture of a solution of 2-aminomethyl-4-(4-fluorobenzyl)morpholine (S. Kato, et al., J. Med. Chem., (1991) 34, 616-624) (22.9 g) in chloroform (200 ml) and 1N aqueous sodium hydroxide solution (100 ml) was added dropwise a solution of benzyl chloroformate (18.7 g) in chloroform (20 ml) under ice-cooling with vigorously stirring. After completion of addition, the internal temperature of the reaction solution was warmed to room temperature, and the solution was Stirred for additional 2 hours. The organic layer was separated, washed with water, then brine, and dried over anhydrous magnesium sulfate. Then, the solvent was removed in vacuo to give 2-benzyloxycarbonylaminomethyl-4-(4-fluorobenzyl)morpholine (34.0 g) as a light brown amorphous solid. LC-MS, m/z; 359 (MH$^+$).

(2) To a solution of the above product (65.1 g) in methylene chloride (500 ml) was added 98% α-chloroethyl chloroformate (3.4 g), and the mixture was stirred at room temperature for 4 hours. The solvent was removed in vacuo, and the residue was dissolved in methanol (500 ml), and then heated to reflux with stirring for 1 hour. After cooling to room temperature, the solvent was removed in vacuo again. The residue was dissolved in ice water, and the iced solution was washed with ethyl acetate three times, alkalified with 30% aqueous potassium hydroxide solution, and then extracted with chloroform. The extract was washed with water, then brine, and then dried over anhydrous magnesium sulfate. The solvent was removed in vacuo to give 2-benzyloxycarbonylamino methylmorpholine (43.6 g) as a pale yellow oil. The oil was used in the next step without any purification. LC-MS, m/z; 251 (MH$^+$).

(3) A mixture of the above product (43.6 g), 1-(tert-butoxycarbonyl)-4-[(p-toluenesulfonyloxy)methyl]piperidine (64.4 g), anhydrous potassium carbonate (48.2 g), potassium iodide (2 g) and acetonitrile (500 ml) was heated to reflux with stirring overnight. After cooling to room temperature, the reaction solution was dried under reduced pressure to be solidified, and the residue was dissolved in chloroform. The solution was washed with water, then brine, and then dried over anhydrous magnesium sulfate, and the solvent was removed in vacuo. The residue was purified by silica gel column chromatography (eluent: ethyl acetate/hexane=1/1 to ethyl acetate) to give 2-benzyloxycarbonylaminomethyl-4-[{1-(tert-butoxycarbonyl)-4-piperidinyl}methyl]morpholine (45.7 g) as a pale yellow oil. LC-MS, m/z; 448 (MH$^+$).

(4) To a solution of the above product (5.0 g) in ethanol (100 ml) was added 10% aqueous palladium carbon (1.5 g), and the mixture was hydrogenated at room temperature under normal pressure. After absorption of theoretical amount of hydrogen, the reaction solution was filtered through Celite® to remove catalysts, and the filtrate was dried under reduced pressure to be-solidified. The residue was dissolved in chloroform, washed with brine, and dried over anhydrous magnesium sulfate, and then the solvent was removed in vacuo to give the titled compound (about 3.8 g) as a pale yellow oil. LC-MS, m/z; 314 (MH$^+$).

Optically-active compounds (T. Morie, et al., Heterocycles, (1994) 38, 1033-1040) were treated as starting materials in the similar manner to Reference Example 12 (Alternative Method 2) to give the following compounds of Reference Examples 13 to 14. Each product was a pale yellow oil.

TABLE 6

| Reference Example | Compound Name | LC-MS, m/z |
|---|---|---|
| 13 | (S)-2-aminomethyl-4-[{1-(tert-butoxycarbonyl)-4-piperidinyl}-methyl]morpholine | 314 (MH$^+$) |
| 14 | (R)-2-aminomethyl-4-[{1-(tert-butoxycarbonyl)-4-piperidinyl}-methyl]morpholine | 314 (MH$^+$) |

Reference Example 15

Preparation of 4-[(1-acetyl-4-piperidinyl)methyl]-2-(tert-butoxycarbonyl)aminomethyl-morpholine

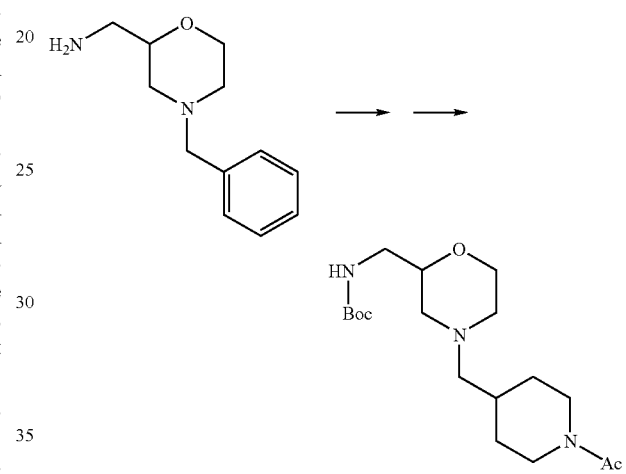

(1) To a solution of 2-aminomethyl-4-benzylmorpholine (S. Kato, et al., J. Med. Chem., (1990) 33, 1406-1413) (1.0 g) in methylene chloride (10 ml) was added di-tert-butyl dicarbonate (1.08 g), and the mixture was stirred at room temperature overnight. The solvent was removed in vacuo, and the residue was purified by silica gel column chromatography (eluent: chloroform/methanol=30/1) to give 4-benzyl-2-(tert-butoxycarbonyl)aminomethylmorpholine (1.4 g) as a yellow oil.
$^1$H-NMR (CDCl$_3$, δppm); 1.42 (9H, s), 1.90 (1H, t, J=10.5 Hz), 2.15 (1H, td, J=3.4, 14.7 Hz), 2.68 (2H, dd, J=11.3, 33.3 Hz), 3.05 (1H, m), 3.28 (1H, m), 3.49 (2H, s), 3.5-3.7 (2H, m), 3.83 (1H, m), 4.86 (1H, br s), 7.2-7.35 (5H, m). LC-MS, m/z; 307 (MH$^+$).

(2) To a solution of the above product (1.4 g) in ethanol (15 ml) was added 10% palladium carbon (0.3 g), and the mixture was hydrogenated at room temperature under normal pressure. After absorption of theoretical amount of hydrogen, the reaction solution was filtered through Celite® to remove catalysts, and the filtrate was dried under reduced pressure to be solidified. To the residue containing 2-(tert-butoxycarbonyl)aminomethylmorpholine were added 1-acetyl-4-(p-toluenesulfonyloxy)methylpiperidine (1.71 g), anhydrous potassium carbonate (1.89 g), sodium iodide (0.68 g) and acetonitrile (30 ml), and the mixture was heated to reflux with stirring overnight. After cooling to room temperature, the reaction solution was dried under reduced pressure to be solidified, and the residue was dissolved in ethyl acetate, washed with water, then brine, and dried over anhydrous magnesium sulfate. The solvent was removed in vacuo, and the residue was purified by silica gel column chromatography (eluent: chloroform/methanol=30/1) to give the titled compound (1.43 g) as a pale yellow oil.

¹H-NMR (CDCl₃, δppm); 0.95-1.15 (2H, m), 1.45 (9H, s), 1.52-1.9 (4H, m), 2.08 (3H, s), 2.16 (3H, d like, J=6.8 Hz), 2.45-2.75 (3H, m), 2.95-3.13 (2H, m), 3.3 (1H, m), 3.5-3.7 (2H, m), 3.82 (2H, t like, J=12.1 Hz), 4.59 (1H, br d, J=13.4 Hz), 4.88 (1H, br s). LC-MS, m/z; 356 (MH⁺).

Reference Example 16

Preparation of 2-aminomethyl-4-[(1-dimethylcarbamoyl-4-piperidinyl)methyl]morpholine

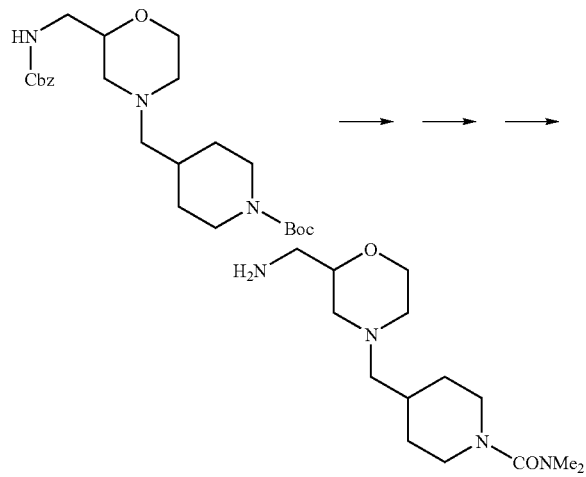

(1) To a solution of 2-benzyloxycarbonylaminomethyl-4-[{1-(tert-butoxycarbonyl)-4-piperidinyl}methyl]morpholine (Reference Example 12 (Alternative Method 2) (3)) (25.0 g) in methanol (50 ml) was added 6N hydrochloric acid (100 ml), and the mixture was stirred at room temperature for 3 hours. The internal temperature of the reaction solution was adjusted to 0° C. or less, and then the reaction solution was alkalified with granulated sodium hydroxide and extracted with chloroform. The extract was washed with a small amount of brine and dried over anhydrous magnesium sulfate, and the solvent was removed in vacuo to give 2-benzyloxycarbonylaminomethyl-4-(4-piperidinyl)methyl)morpholine (18.6 g) as a pale yellow oil.

¹H-NMR (CDCl₃, δppm); 1.0-1.2 (2H, m), 1.5-1.8 (5H, m), 2.0-2.2 (3H, m), 2.5-2.75 (4H, m), 3.0-3.25 (3H, m), 3.35 (1H, m), 3.5-3.7 (2H, m), 3.73 (1H, d like), 5.1 (1H, m), 5.11 (2H, s), 7.25-7.9 (5H, m). LC-MS, m/z; 348 (MH⁺).

(2) To a solution of the above product (5.0 g) and TEA (3.0 ml) in methylene chloride (75 ml) was added dropwise dimethylcarbamoyl chloride (1.6 ml) under ice-cooling. After addition, the internal temperature of the reaction solution was warmed to room temperature, and the solution was stirred overnight. The reaction solution was washed with water twice and sequentially washed with 10% aqueous solution of citric acid and brine, and then dried over anhydrous magnesium sulfate, and the solvent was removed in vacuo. The residue was purified by silica gel column chromatography (eluent: chloroform/methanol=40/1) to give 2-benzyloxycarbonylaminomethyl-4-[(1-dimethylcarbamoyl-4-piperidinyl)methyl]morpholine (4.1 g) as a pale yellow oil.

¹H-NMR (CDCl₃, δppm); 1.0-1.25 (2H, m), 1.65-1.9 (4H, m), 2.0-2.25 (3H, m), 2.5-2.8 (4H, m), 2.81 (6H, s), 3.15 (1H, m), 3.4 (1H, m), 3.5-3.8 (4H, m), 3.83 (1H, d like, J=9.7 Hz), 5.1 (1H, m), 5.11 (2H, s), 7.25-7.5 (5H, m). LC-MS, m/z; 419 (MH⁺).

(3) To a solution of the above product (10.7 g) in ethanol (100 ml) was added 10% palladium carbon (2.0 g), and the mixture was hydrogenated at room temperature under 4 kgf/cm². After absorption of theoretical amount of hydrogen, the reaction solution was filtered through Celite® to remove catalysts, and the filtrate was dried under reduced pressure to be solidified. The residue was dissolved in chloroform, washed with brine, and dried over anhydrous magnesium sulfate, and then the solvent was removed in vacuo to give the titled compound (about 7.3 g) as a pale yellow oil.

¹H-NMR (CDCl₃, δppm); 1.0-1.25 (2H, m), 1.55-1.7 (3H, m), 1.91 (1H, t, J=10.4 Hz), 2.19 (3H, d like, J=6.8 Hz), 2.55-2.7 (5H, m), 2.81 (6H, s), 2.85-3.15 (3H, m), 3.52 (2H, br s), 3.5-4.0 (3H, m). LC-MS, m/z; 285 (MH⁺).

An optically-active compound (S)-2-benzyloxycarbonylaminomethyl-4-[{1-(tert-butoxycarbonyl)-4-piperidinyl}methyl]morpholine (a synthetic intermediate of Reference Example 13) was treated as a starting material in the similar manner to Reference Example 16 to give a compound of Reference Example 17. The starting material was prepared with reference to methods described in (1) to (3) of Reference Example 12 (Alternative Method 2).

TABLE 7

| Reference Example | Compound Name | Form | LC-MS, m/z |
| --- | --- | --- | --- |
| 17 | (S)-2-aminomethyl-4-[(1-dimethylcarbamoyl-4-piperidinyl)methyl]morpholine | pale yellow oil | 285 (MH⁺) |

Reference Example 18

Preparation of 2-aminomethyl-4-[(1-methylcarbamoyl-4-piperidinyl)methyl]morpholine

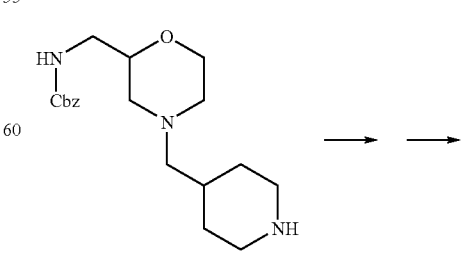

-continued

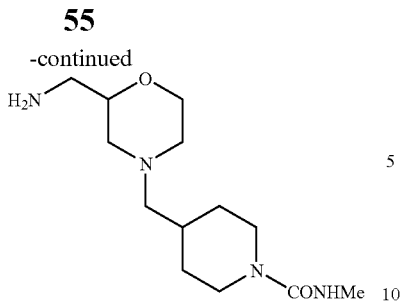

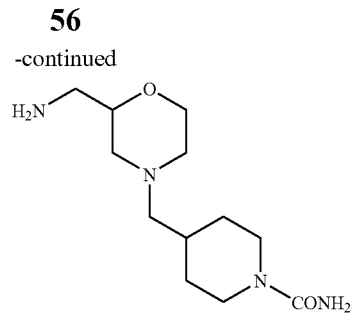

(1) To a solution of trichloromethyl chloroformate (0.35 ml) in methylene chloride (10 ml) was added dropwise 2-benzyloxycarbonylaminomethyl-4-(4-piperidinyl)methyl)morpholine (Reference Example 16(1)) (2.0 g) in methylene chloride (20 ml) over 20 minutes with ice-cooling. The internal temperature of the reaction solution was warmed to room temperature, and then stirred for 1.5 hours. The reaction solution was ice-cooled again, and then thereto were added dropwise 2N solution of methylamine in THF (11.6 ml) and a solution of TEA (3.2 ml) in methylene chloride (10 ml) over 15 minutes. After completion of addition, the internal temperature of the reaction solution was warmed to room temperature. The reaction solution was stirred overnight, and then washed with water, then brine. Then, the solution was dried over anhydrous magnesium sulfate, and the solvent was removed in vacuo. The residue was purified by silica gel column chromatography (eluent: chloroform/methanol=30/1) to give 2-benzyloxycarbonylaminomethyl-4-[(1-methylcarbamoyl-4-piperidinyl)methyl]morpholine (2.3 g) as a pale yellow oil.

$^1$H-NMR (CDCl$_3$, δppm); 1.0-1.2 (2H, m), 1.55-1.8 (4H, m), 2.0-2.2 (3H, m), 2.55-2.8 (4H, m), 2.81 (3H, d like, J=4.3 Hz), 3.15 (1H, m), 3.38 (1H, m), 3.5-3.7 (2H, m), 3.25-4.0 (3H, m), 4.4 (1H, d like), 5.10 (2H, s), 5.1 (1H, m), 7.25-7.4 (5H, m). LC-MS, m/z; 405 (MH$^+$).

(2) In place of 2-benzyloxycarbonylaminomethyl-4-[(1-dimethylcarbamoyl-4-piperidinyl)methyl]morpholine of Reference Example 16(3), the above product was treated in the similar manner to Reference Example 16(3) to give the titled compound as a pale yellow oil.

$^1$H-NMR (CDCl$_3$, δppm); 1.1-1.3 (2H, m), 1.94 (2H, br t, J=14.6 Hz), 2.16 (1H, br s), 2.77 (3H, s), 2.7-2.9 (2H, m), 2.9-3.3 (10H, m), 3.7 (1H, m), 3.99 (2H, br d, J=13.0 Hz), 4.10 (1H, br d, J=11.5 Hz), 4.31 (1H, br t, J=12.2 Hz), 4.49 (1H, br s). LC-MS, m/z; 271 (MH$^+$).

Reference Example 19

Preparation of 2-aminomethyl-4-[(1-carbamoyl-4-piperidinyl)methyl]morpholine

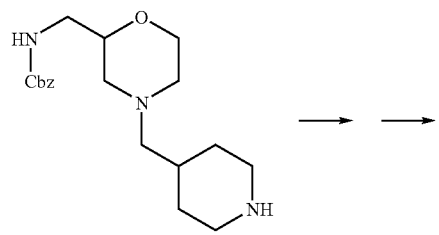

(1) To a solution of 2-benzyloxycarbonylaminomethyl-4-(4-piperidinylmethyl)morpholine (Reference Example 16(1)) (1.0 g) in methylene chloride (10 ml) was added trimethylsilyl isocyanate (0.40 g) at room temperature, and the mixture was stirred overnight. The reaction solution was washed with water, then brine, and then dried over anhydrous magnesium sulfate, and the solvent was removed in vacuo. The residue was purified by silica gel column chromatography (eluent: chloroform/methanol=30/1) to give 2-benzyloxycarbonylaminomethyl-4-[(1-carbamoyl-4-piperidinyl)methyl]morpholine (0.75 g) as a pale yellow oil.

$^1$H-NMR (CDCl$_3$, δppm), 1.12 (2H, ddd, J=3.9, 16.1, 40.2 Hz), 1.55-1.8 (4H, m), 2.05-2.2 (3H, m), 2.62 (1H, dd, J=10.9, 35.5 Hz), 2.80 (2H, t, J=12.2 Hz), 3.15 (1H, m), 3.4 (1H, m), 3.5-3.7 (2H, m), 3.83 (1H, d like, J=11.4 Hz), 3.92 (2H, br d, J=12.1 Hz), 4.45 (2H, s), 5.11 (2H, s), 5.15 (1H, m), 7.25-7.4 (5H, m). LC-MS, m/z; 391 (MH$^+$).

(2) In place of 2-benzyloxycarbonylaminomethyl-4-[(1-dimethylcarbamoyl-4-piperidinyl)methyl]-morpholine of Reference Example 16(3), the above product was treated in the similar manner to Reference Example 16(3) to give the titled compound as a pale yellow oil. LC-MS, m/z; 257 (MH$^+$).

Example 1

Preparation of 4-amino-N-[{4-[(1-(tert-butoxycarbonyl)-4-piperidinyl)methyl]-2-morpholinyl}-methyl]-5-chloro-2-methoxybenzamide

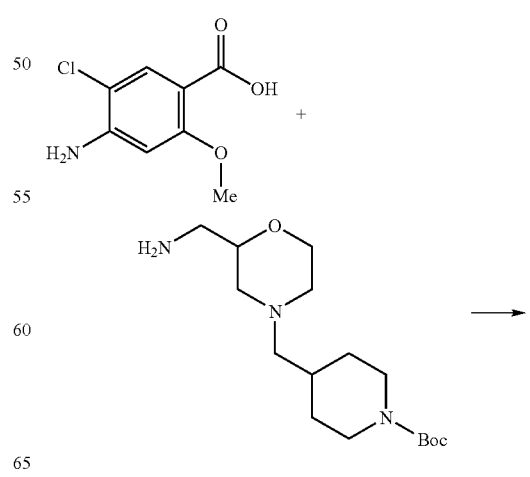

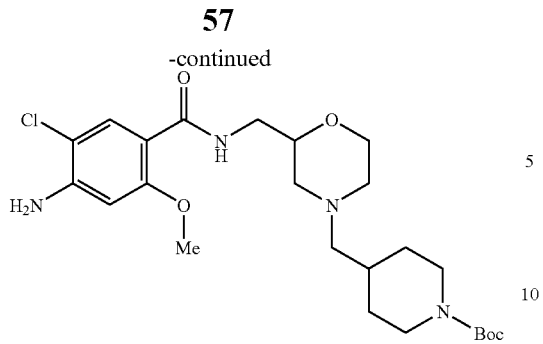

To a suspension of 4-amino-5-chloro-2-methoxybenzoic acid (27.6 g) in chloroform (200 ml) was added dropwise TEA (16.6 g) at room temperature with stirring. The internal temperature of the reaction solution was ice-cooled, and then thereto was slowly added dropwise ethyl chloroformate (16.3 g) so that the internal temperature did not rise over 5° C. After completion of addition, the mixture was stirred at internal temperature of 0 to 5° C. for 1 hour. To the reaction solution was slowly added dropwise a solution of 2-aminomethyl-4-[1-(tert-butoxycarbonyl)-4-piperidinylmethyl]morpholine (Reference Example 12) (42.9 g) in chloroform (50 ml) so that the internal temperature did not rise over 5° C., and after completion of addition, the mixture was stirred overnight without an ice bath. The reaction solution was sequentially washed with water, 5% aqueous potassium hydroxide solution, water, 5% aqueous solution of citric acid, water and brine. The solution was dried over anhydrous magnesium sulfate, and then the solvent was removed in vacuo. The residue was purified by silica gel column chromatography (eluent: ethyl acetate) to give the titled compound (32.4 g) as an amorphous solid.

$^1$H-NMR (DMSO-d$_6$, δppm); 0.8-1.0 (2H, br q, J=11.6 Hz), 1.38 (9H, s), 1.65 (2H, br d, J=11.3 Hz), 1.74 (1H, t, J=10.6 Hz), 1.95 (1H, m), 2.10 (2H, d, J=7.7 Hz), 2.55-2.8 (4H, m), 3.2-3.6 (5H, m), 3.83 (3H, s), 3.75-4.0 (3H, m), 5.96 (2H, s), 6.48 (1H, s), 7.68 (1H, s), 7.97 (1H, br t, J=5.6 Hz). LC-MS, m/z; 497 (MH$^+$).

Example 1 (Alternative Method)

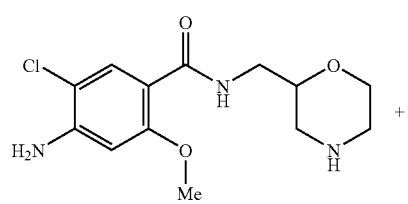 +

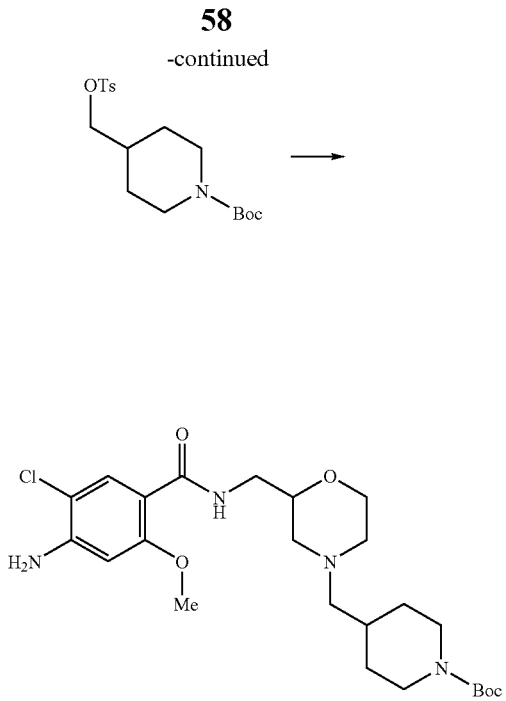

A mixture of 4-amino-5-chloro-2-methoxy-N-(2-morpholinylmethyl)benzamide (Reference Example 2) (16.2 g), 1-(tert-butoxycarbonyl)-4-[(p-toluenesulfonyloxy)methyl]piperidine (28.5 g), anhydrous potassium carbonate (22.4 g), sodium iodide (12.2 g) and acetonitrile (220 ml) was heated to reflux overnight with stirring. After cooling to room temperature, the reaction solution was dried under reduced pressure to be solidified, and to the residue was added water and the mixture was extracted with ethyl acetate. The extract was washed with brine and dried over anhydrous magnesium sulfate, and the solvent was removed in vacuo. The residue was purified by silica gel column chromatography (eluent: ethyl acetate) to give the titled compound (27.0 g) as an amorphous solid.

Optically-active compounds (Reference Example 13, Reference Example 14) were treated as starting materials in the similar manner to Example 1 to give the following compounds of Example 2 to 3.

TABLE 8

| Example | Compound Name | Form | LC-MS, m/z |
|---|---|---|---|
| 2 | (S)-4-amino-N-[{4-[(1-(tert-butoxycarbonyl)-4-piperidinyl)methyl]-2-morpholinyl}methyl]-5-chloro-2-methoxybenzamide | amorphous solid | 497 (MH$^+$) |
| 3 | (R)-4-amino-N-[{4-[(1-(tert-butoxycarbonyl)-4-piperidinyl)methyl]-2-morpholinyl}methyl]-5-chloro-2-methoxybenzamide | amorphous solid | 497 (MH$^+$) |

Example 4

Preparation of 4-amino-N-[{4-[(1-(tert-butoxycarbonyl)-4-piperidinyl)methyl]-2-morpholinyl}-methyl]-5-chloro-2-ethoxybenzamide 1.5 fumarate

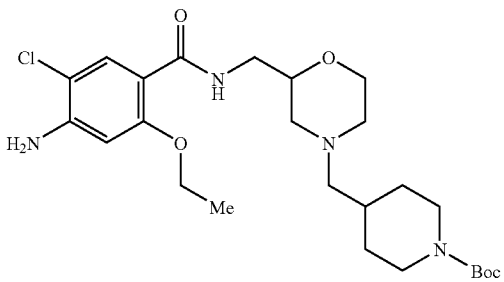

In place of 4-amino-5-chloro-2-methoxybenzoic acid of Example 1, 4-amino-5-chloro-2-ethoxybenzoic acid was treated in the similar manner to Example 1 to give an amorphous solid which was sequentially treated with fumaric acid to give the titled compound as a powder. Melting point 167-169° C. (recrystallized from E/DE)

$^1$H-NMR (DMSO-d$_6$, δppm); 0.8-1.0 (2H, br q, J=10.4 Hz), 1.3-1.5 (4H, m), 1.37 (9H, s), 1.40 (3H, t, J=7.0 Hz), 1.65 (2H, br d, J=10.6 Hz), 1.81 (1H, t, J=10.6 Hz), 2.02 (1H, t like, J=10.6 Hz), 2.13 (2H, d, J=6.0 Hz), 2.5-2.75 (4H, m), 3.2 (1H, m), 3.35-3.6 (3H, m), 3.80 (1H, d, J=11.3 Hz), 3.89 (2H, d like, J=12.1 Hz), 4.06 (2H, q, J=7.0 Hz), 5.93 (2H, s), 6.46 (1H, s), 6.61 (3H, s), 7.70 (1H, s), 8.06 (1H, t like, J=4.8 Hz). LC-MS, m/z; 511 (MH$^+$).

Optically-active compounds (Reference Example 13, Reference Example 14) were treated as starting materials in the similar manner to Example 4 to give the following compounds of Examples 5 to 6.

TABLE 9

| Example | Compound Name | Form | LC-MS, m/z |
| --- | --- | --- | --- |
| 5 | (S)-4-amino-N-[{4-[(1-(tert-butoxycarbonyl)-4-piperidinyl)methyl]-2-morpholinyl}methyl]-5-chloro-2-ethoxybenzamide | amorphous solid | 511 (MH$^+$) |
| 6 | (R)-4-amino-N-[{4-[(1-(tert-butoxycarbonyl)-4-piperidinyl}methyl]-2-morpholinyl}methyl]-5-chloro-2-ethoxybenzamide | amorphous solid | 511 (MH$^+$) |

Example 7

Preparation of 4-amino-N-[{4-[(1-(tert-butoxycarbonyl)-4-piperidinyl)methyl]-2-morpholinyl}-methyl]-5-chloro-2,3-dihydrobenzo[b]furan-7-carboxamide

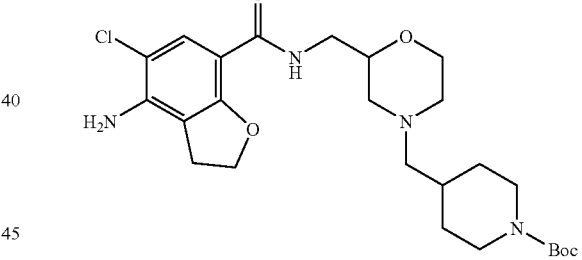

In place of 4-amino-5-chloro-2-methoxybenzoic acid of Example 1, 4-amino-5-chloro-2,3-dihydrobenzo[b]furan-7-carboxylic acid was treated in the similar manner to Example 1 to give the titled compound as an amorphous solid.

$^1$H-NMR (CDCl$_3$, δppm); 0.92-1.13 (2H, m), 1.45 (9H, s), 1.5-1.8 (4H, m), 1.87 (1H, d, J=10.3 Hz), 2.05-2.2 (3H, m), 2.55-2.85 (4H, m), 3.06 (2H, t, J=8.8 Hz), 3.35 (1H, m), 3.6-3.75 (3H, m), 3.87 (1H, br d, J=9.7 Hz), 3.95-4.2 (2H, br d), 4.2 (1H, m), 4.78 (2H, t, J=8.8 Hz), 7.61 (1H, br t, J=5.9 Hz), 7.86 (1H, s). LC-MS, m/z; 509 (MH$^+$).

Example 7 (Alternative Method)

In place of 4-amino-5-chloro-2-methoxy-N-(2-morpholinylmethyl)benzamide of Example 1 (Alternative Method), 4-amino-5-chloro-N-(2-morpholinylmethyl)-2,3-dihydrobenzo[b]furan-7-carboxamide (Reference Example 6) was treated in the similar manner to Example 1 (Alternative Method) to give the titled compound as an amorphous solid.

Optically-active compounds (Reference Example 13, Reference Example 14) were treated as starting materials in the similar manner to Example 7 to give the following compounds of Examples 8 to 9.

TABLE 10

| Example | Compound Name | Form | LC-MS, m/z |
|---|---|---|---|
| 8 | (S)-4-amino-N-[{4-[(1-(tert-butoxycarbonyl)-4-piperidinyl)methyl]-2-morpholinyl}methyl]-5-chloro-2,3-dihydrobenzo[b]furan-7-carboxamide | amorphous solid | 509 (MH+) |
| 9 | (R)-4-amino-N-[{4-[(1-(tert-butoxycarbonyl)-4-piperidinyl)methyl]-2-morpholinyl}methyl]-5-chloro-2,3-dihydrobenzo[b]furan-7-carboxamide | amorphous solid | 509 (MH+) |

The following compounds of Examples 10 and 12 to 17 were prepared in the similar manner to Example 1 and Example 1 (Alternative Method). Each product was an amorphous solid.

TABLE 11

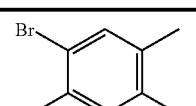

| Example | Compound Name | R— | LC-MS, m/z |
|---|---|---|---|
| 10 | 4-amino-5-bromo-N-[{4-[(1-(tert-butoxycarbonyl)-4-piperidinyl)methyl]-2-morpholinyl}methyl]-2-methoxybenzamide | 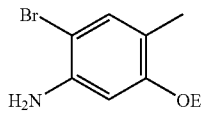 | 543 (MH+) |
| 12 | (S)-4-amino-5-bromo-N-[{4-[(1-(tert-butoxycarbonyl)-4-piperidinyl)methyl]-2-morpholinyl)methyl]-2-ethoxybenzamide | 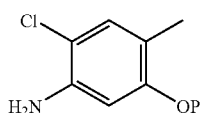 | 557 (MH+) |
| 13 | 4-amino-N-[{4-[(1-(tert-butoxycarbonyl)-4-piperidinyl)methyl]-2-morpholinyl}methyl]-5-chloro-2-propoxybenzamide | 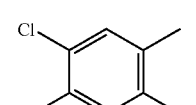 | 525 (MH+) |
| 14 | 4-amino-N-[{4-[(1-(tert-butoxycarbonyl)-4-piperidinyl)methyl]-2-morpholinyl}methyl]-5-chloro-2-isopropoxybenzamide | | 525 (MH+) |
| 15 | 2-allyloxy-4-amino-N-[{4-[(1-(tert-butoxycarbonyl)-4-piperidinyl)methyl]-2-morpholinyl}methyl]-5-chlorobenzamide | 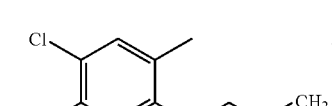 | 523 (MH+) |
| 16 | 6-amino-N-[{4-[(1-(tert-butoxycarbonyl)-4-piperidinyl)methyl]-2-morpholinyl}methyl]-5-chloro-2-methoxypyridine-3-carboxamide | 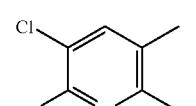 | 498 (MH+) |
| 17 | 6-amino-5-bromo-N-[{4-[(1-(tert-butoxycarbonyl)-4-piperidinyl)methyl]-2-morpholinyl}methyl]-2-methoxypyridine-3-carboxamide | 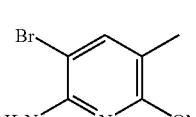 | 544 (MH+) |

Example 11

Preparation of 4-amino-5-bromo-N-[{4-[(1-(tert-butoxycarbonyl)-4-piperidinyl)methyl]-2-morpholinyl}methyl]-2-ethoxybenzamide 1.5 fumarate

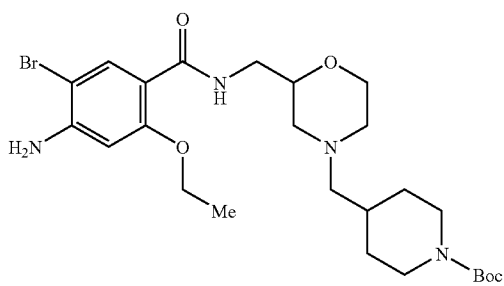

In place of 4-amino-5-chloro-2-methoxybenzoic acid of Example 1, 4-amino-5-bromo-2-ethoxybenzoic acid was treated in the similar manner to Example 1 to give an amorphous solid which was sequentially treated with fumaric acid to give the titled compound as a powder. Melting point 171-172° C. (recrystallized from E)

¹H-NMR (DMSO-d₆, δppm); 0.8-1.0 (2H, m), 1.37 (9H, s), 1.40 (3H, t, J=7.1 Hz), 1.65 (3H, br d, J=10.8 Hz), 1.81 (1H, t, J=10.5 Hz), 2.01 (1H, br t), 2.12 (2H, d like, J=6.4 Hz), 2.70 (4H, dd, J=11.4, 29.3 Hz), 3.2 (1H, m), 3.4-3.6 (3H, m), 3.80 (1H, d, J=10.6 Hz), 3.89 (2H, br d, J=12.3 Hz), 4.06 (2H, q, J=7.1 Hz), 5.87 (2H, s), 6.47 (1H, s), 6.61 (3H, s), 7.85 (1H, s), 8.04 (1H, t like). LC-MS, m/z; 557 (MH⁺).

Example 18

Preparation of 4-amino-N-[{4-[(1-(tert-butoxycarbonyl)-4-piperidinyl)methyl]-1,4-hexahydroxazepin-2-yl}methyl]-5-chloro-2-methoxybenzamide

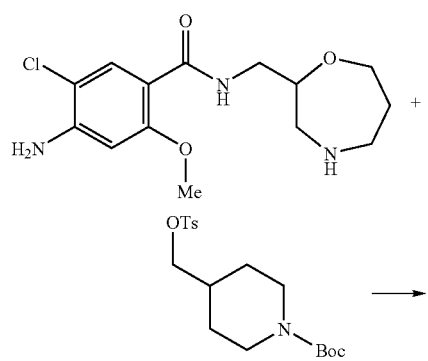

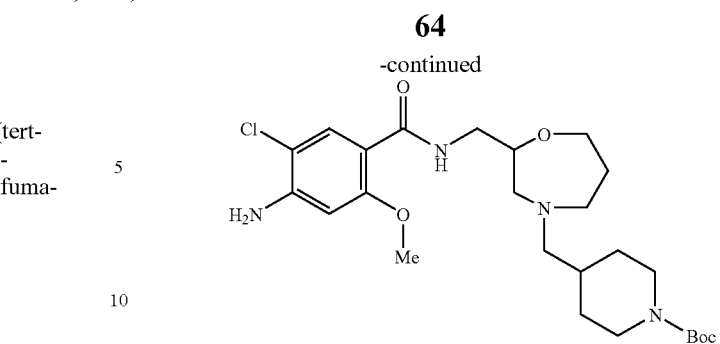

In place of 4-amino-5-chloro-2-methoxy-N-(2-morpholinylmethyl)benzamide of Example 1 (Alternative Method), 4-amino-5-chloro-N-[(1,4-hexahydroxazepin-2-yl)methyl]-2-methoxybenzamide (Reference Example 3) was treated in the similar manner to Example 1 (Alternative Method) to give the titled compound as an amorphous solid.

¹H-NMR (CDCl₃, δppm); 0.95-1.1 (2H, m), 1.44 (9H, s), 1.5-2.0 (5H, m), 2.32 (2H, d, J=7.1 Hz), 2.45 (1H, m), 2.55-2.85 (5H, m), 3.15 (1H, m), 3.65-3.8 (3H, m), 3.89 (3H, s), 3.9 (1H, m), 4.0-4.15 (2H, m), 4.37 (2H, s), 6.29 (1H, s), 8.04 (1H, br t like), 8.10 (1h, s). LC-MS, m/z; 511 (MH⁺), 411.

Example 19

Preparation of 4-amino-N-[{4-[(1-(tert-butoxycarbonyl)-3-piperidinyl)methyl]-2-morpholinyl}-methyl]-5-chloro-2-ethoxybenzamide

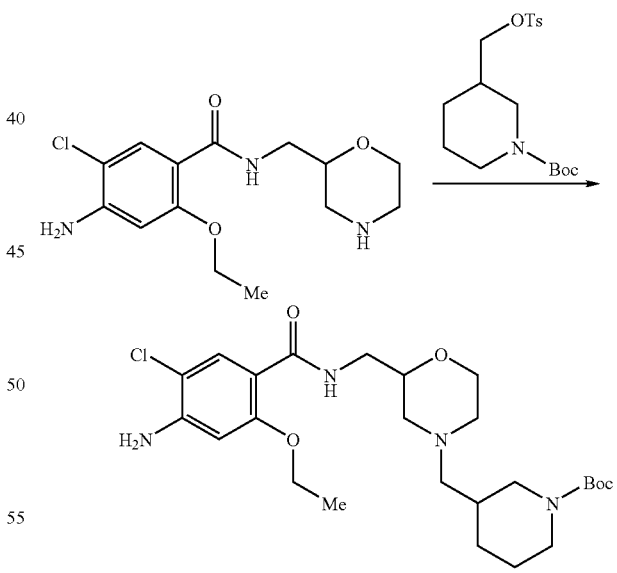

In place of 1-(tert-butoxycarbonyl)-4-[(p-toluenesulfonyloxy)methyl]piperidine of Example 1 (Alternative Method), 1-(tert-butoxycarbonyl)-3-[(p-toluenesulfonyloxy)methyl]piperidine was treated in the similar manner to Example 1 (Alternative Method) to give the titled compound as a white amorphous solid.

¹H-NMR (CDCl₃, δppm); 1.1 (1H, m), 1.45 (9H, s), 1.50 (3H, t, J=7.0 Hz), 1.5-2.2 (8H, m), 2.6-2.8 (4H, m), 3.35 (1H, m), 3.6-3.75 (3H, m), 3.8-4.0 (3H, m), 4.08 (2H, q, J=7.0 Hz), 4.35 (2H, s), 6.27 (1H, s), 8.11 (1H, s), 8.22 (1H, t like). LC-MS, m/z; 511 (MH+).

Example 20

Preparation of 4-amino-N-[{4-[(1-(tert-butoxycarbonyl)-3-azetidinyl)methyl]-2-morpholinyl}-methyl]-5-chloro-2-ethoxybenzamide

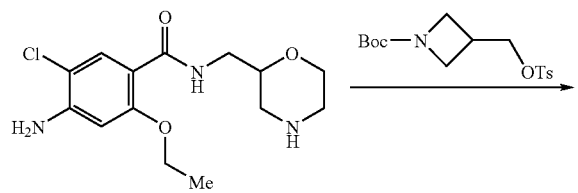

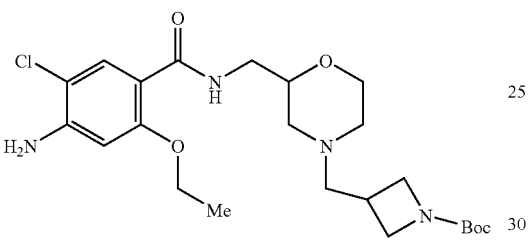

In place of 1-(tert-butoxycarbonyl)-4-[(p-toluenesulfonyloxy)methyl]piperidine of Example 1 (Alternative Method), 1-(tert-butoxycarbonyl)-3-[(p-toluenesulfonyloxy)methyl] azetidine (Reference Example 1) was treated in the similar manner to Example 1 (Alternative Method) to give the titled compound as a white amorphous solid.

$^1$H-NMR (CDCl$_3$, δppm); 1.43 (9H, s), 1.50 (3H, t, J=7.0 Hz), 1.97 (1H, br t, J=10.5 Hz), 2.17 (1H, td, J=3.3, 11.2 Hz), 2.5-2.65, 2.65-2.8 (5H, m), 3.2-3.4 (2H, m), 3.5-3.75 (6H, m), 3.87 (1H, m), 4.09 (2H, q, J=7.0 Hz), 4.35 (2H, s), 6.27 (1H, s), 8.11 (1H, s), 8.21 (1H, t like). LC-MS, m/z; 314.

Example 21

Preparation of 4-amino-N-[{4-[(1-(tert-butoxycarbonyl)-3-pyrrolidinyl)methyl]-2-morpholinyl}methyl]-5-chloro-2-ethoxybenzamide

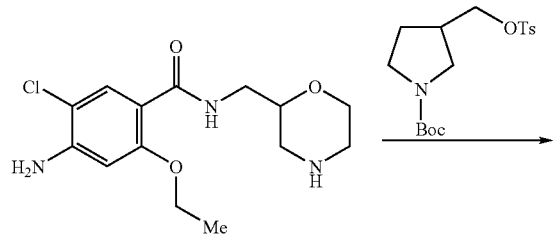

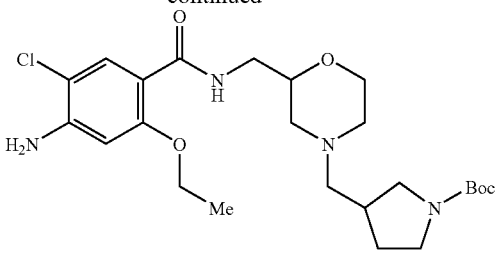

In place of 1-(tert-butoxycarbonyl)-4-[(p-toluenesulfonyloxy)methyl]piperidine of Example 1 (Alternative Method), 1-(tert-butoxycarbonyl)-3-[(p-toluenesulfonyloxy)methyl] pyrrolidine was treated in the similar manner to Example 1 (Alternative Method) to give the titled compound as a white amorphous solid.

$^1$H-NMR (CDCl$_3$, δppm); 1.46 (9H, s), 1.50 (3H, t, J=7.0 Hz), 1.8-2.0 (2H, m), 2.15 (1H, m), 2.2-2.45 (3H, m), 2.65-2.8 (2H, m), 3.0 (1H, m), 3.1-3.55 (5H, m), 3.67 (3H, br s), 3.86 (1H, br d, J=10.3 Hz), 4.09 (2H, q, J=7.0 Hz), 4.34 (2H, s), 6.27 (1H, s), 8.11 (1H, s), 8.21 (1H, t like). LC-MS, m/z; 497 (MH+), 397.

Example 22

Preparation of 4-amino-5-chloro-2-ethoxy-N-[[4-(4-piperidinylmethyl)-2-morpholinyl]methyl]-benzamide 2 fumarate

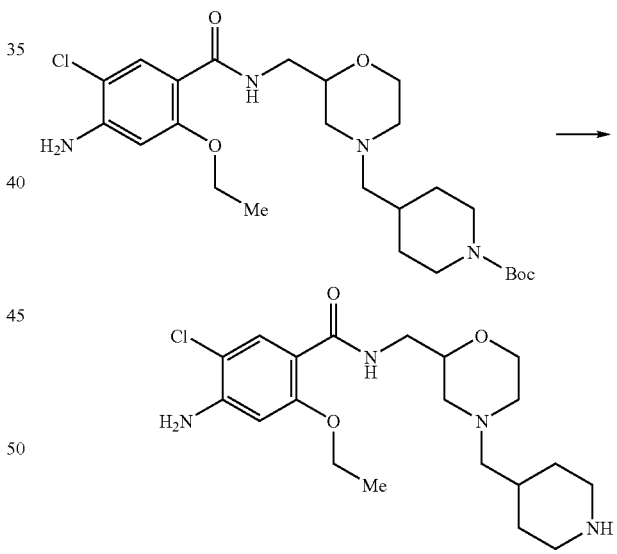

To a solution of 4-amino-N-[{4-[(1-(tert-butoxycarbonyl)-4-piperidinyl)methyl]-2-morpholinyl}methyl]-5-chloro-2-ethoxybenzamide (Example 4) (43.0 g) in methanol (20 ml) was added 6N hydrochloric acid (100 ml) under ice-cooling, and then the mixture was stirred at room temperature overnight. The reaction solution was alkalified by adding granulated sodium hydroxide under ice-cooling, and then diluted with ice water. The precipitated solid was filtered in vacuo, washed with water, and then dried to give a base of the titled compound (35.6 g). The solid was treated with fumaric acid to give the titled compound as a solid. Melting point 138-140° C. (recrystallized from E)

1H-NMR (DMSO-d6, δppm); 1.23 (2H, br q, J=11.7 Hz), 1.41 (3H, t, J=6.9 Hz), 1.7-1.95 (4H, br d), 2.01 (1H, br t, J=9.8 Hz), 2.13 (2H, br d, J=6.2 Hz), 2.65 (1H, d like, J=11.2 Hz), 2.78 (3H, br q, J=10.8 Hz), 3.23 (3H, br d, J=12.3 Hz), 3.35-3.65 (3H, m), 3.81 (1H, br d, J=11.2 Hz), 4.07 (2H, q, J=6.9 Hz), 5.96 (2H, s), 6.47 (1H, s), 6.54 (4H, s), 7.71 (1H, s), 8.08 (1H, t like, J=4.7 Hz). LC-MS, m/z; 411 (MH+).

Examples 23-42

In place of 4-amino-N-[{4-[(1-(tert-butoxycarbonyl)-4-piperidinyl)methyl]-2-morpholinyl}-methyl]-5-chloro-2-ethoxybenzamide of Example 22, the corresponding amide compounds were treated in the similar manner to Example 22 to give the following compounds of Examples 23-42 as a powder or an amorphous solid.

TABLE 12

| Example | V | *1) | R1 | Y | l | m | n | Q | LC-MS m/z (MH+) |
|---|---|---|---|---|---|---|---|---|---|
| 23 | CH | RS | Me | Cl | 1 | 2 | 1 | 2F2) | 397/ |
| 24 | CH | S | Me | Cl | 1 | 2 | 1 | — | 397 |
| 25 | CH | R | Me | Cl | 1 | 2 | 1 | — | 397 |
| 26 | CH | S | Et | Cl | 1 | 2 | 1 | — | 411 |
| 27 | CH | R | Et | Cl | 1 | 2 | 1 | — | 411 |
| 28 | C— | RS | —CH2—CH2 | Cl | 1 | 2 | 1 | — | 409 |
| 29 | C— | S | —CH2—CH2 | Cl | 1 | 2 | 1 | — | 409 |
| 30 | C— | R | —CH2—CH2 | Cl | 1 | 2 | 1 | — | 409 |
| 31 | CH | RS | Me | Br | 1 | 2 | 1 | — | 443 |
| 32 | CH | RS | Et | Br | 1 | 2 | 1 | — | 457 |
| 33 | CH | S | Et | Br | 1 | 2 | 1 | — | 457 |
| 34 | CH | RS | Pr | Cl | 1 | 2 | 1 | — | 425 |
| 35 | CH | RS | iPr | Cl | 1 | 2 | 1 | — | 425 |
| 36 | CH | RS | CH2CH=CH2 | Cl | 1 | 2 | 1 | — | 423 |
| 37 | N | RS | Me | Cl | 1 | 2 | 1 | — | 398 |
| 38 | N | RS | Me | Br | 1 | 2 | 1 | — | 444 |
| 39 | CH | RS | Me | Cl | 2 | 2 | 1 | — | 411 |
| 40 | CH | RS | Et | Cl | 1 | 1 | 2 | — | 411 |
| 41 | CH | RS | Et | Cl | 1 | 1 | 0 | — | 383 |
| 42 | CH | RS | Et | Cl | 1 | 1 | 1 | — | 397 |

1)Symbols refer to configurations.
2)"F" refers to fumaric acid. Melting point of a compound of Example 23 was 104-107° C. (recrystallizing solvent: E).

Example 43

Preparation of 4-amino-N-[{4-((1-carbamoyl-4-piperidinyl)methyl)-2-morpholinyl}methyl]-5-chloro-2-ethoxybenzamide

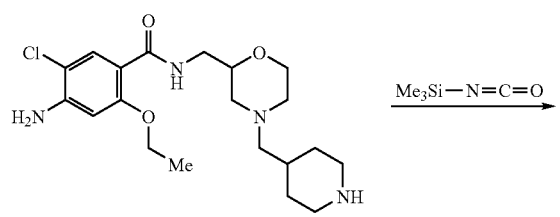

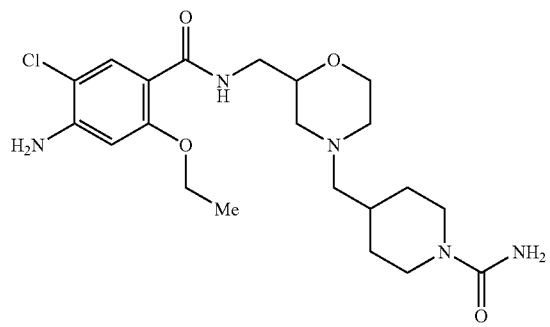

To a solution of 4-amino-5-chloro-2-ethoxy-N-[{4-(4-piperidinylmethyl)-2-morpholinyl}-methyl]benzamide (Example 22) (1.0 g) in methylene chloride (15 ml) was added trimethylsilyl isocyanate (0.34 g) at room temperature, and the mixture was stirred for 2.5 hours. The solvent was removed in vacuo, and then to the residue was added water. The precipitated solid was filtered in vacuo, washed with aqueous ethanol and dried to give the titled compound (1.0 g) as a white solid. Melting point 201-207° C. (recrystallized from E/H)

1H-NMR (CDCl3, δppm); 1.12 (2H, ddd, J=3.7, 12.0, 20.4 Hz), 1.50 (3H, t, J=7.0 Hz), 1.64 (2H, s), 1.62-1.82 (2H, m), 1.92 (1H, t, J=10.5 Hz), 2.08-2.22 (3H, m), 2.62 (1H, d like, J=9.9 Hz), 2.78 (3H, br q, J=12.2 Hz), 3.38 (1H, m), 3.58-3.77 (3H, m), 3.8-4.0 (3H, m), 4.05 (2H, q, J=7.0 Hz), 4.24-4.44 (3H, m), 6.27 (1H, s), 8.11 (1H, s), 8.23 (1H, t like). LC-MS, m/z; 454 (MH+).

Example 43 (Alternative Method)

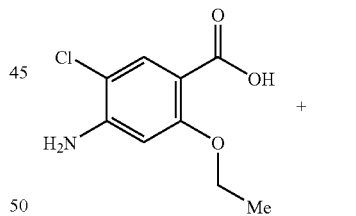

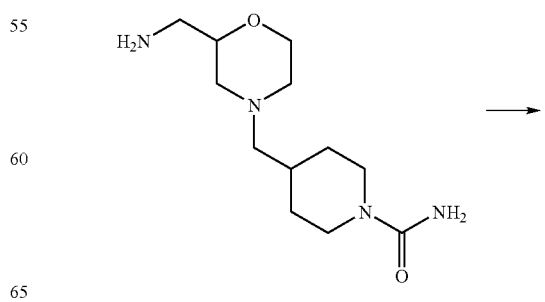

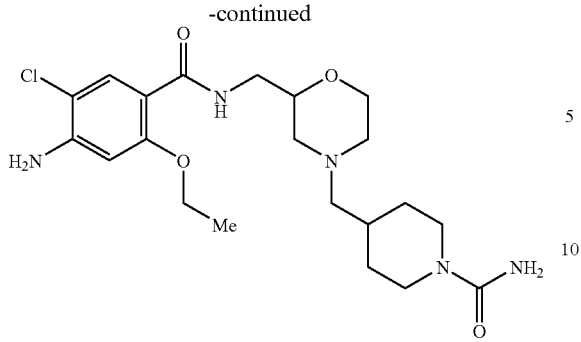

A solution of 4-amino-5-chloro-2-ethoxybenzoic acid (0.36 g) and N,N'-carbonyldiimidazole (0.30 g) in DMF (15 ml) was stirred at room temperature for 1 hour. To the reaction solution was added 2-aminomethyl-4-(1-carbamoyl-4-piperidinylmethyl)morpholine (Reference Example 19) (0.49 g), and the mixture was stirred at room temperature overnight. The reaction solution was dried under reduced pressure to be solidified. The residue was dissolved in chloroform, washed with water, then brine, and then dried over anhydrous magnesium sulfate. The solvent was removed in vacuo. The residue was purified by silica gel column chromatography (eluent: chloroform/methanol=30/1) to give the titled compound (0.45 g) as a white solid.

Examples 44-66

In place of 4-amino-5-chloro-2-ethoxy-N-[{4-(4-piperidinylmethyl)-2-morpholinyl}methyl]-benzamide of Example 43, the corresponding amide compounds and the corresponding isocyanates were treated in the similar manner to Example 43 to give the following compounds of Table 4 as an amorphous solid or a powder. Certain amorphous solids were treated with fumaric acid to form a salt.

TABLE 13

| Example | *[1] | R[1] | B | Q | LC-MS m/z; (MH+) |
|---|---|---|---|---|---|
| 44 | S | Et | $NH_2$ | — | 454 |
| 45 | RS | Me | NHMe | —[2] | 454 |
| 46-1 | RS | Et | NHMe | —[3] | 468 |
| 47 | S | Et | NHMe | — | 468 |
| 48 | R | Et | NHMe | — | 468 |
| 49 | S | Me | NHEt | — | 468 |
| 50 | RS | Et | NHEt | 3/2F[4] | 482 |
| 51 | S | Me | NH$^t$Bu | — | 496 |
| 52 | S | Me | NHPh | — | 516 |
| 53 | S | Me | NH(2-MeOC$_6$H$_4$) | — | 546 |
| 54 | S | Me | NH(3-CF$_3$C$_6$H$_4$) | — | 584 |
| 55 | S | Me | NH(4-CO$_2$EtC$_6$H$_4$) | — | 588 |
| 56 | S | Me | NH(3-COMeC$_6$H$_4$) | — | 558 |
| 57 | S | Me | NH(3,5-Me$_2$C$_6$H$_3$) | — | 544 |
| 58 | S | Me | NH(3,4-Cl$_2$C$_6$H$_3$) | — | 586 |
| 59 | S | Me | NHCH$_2$Ph | — | 530 |
| 60 | S | Me | NHCH$_2$(2-MeC$_6$H$_4$) | — | 544 |
| 61 | S | Me | NHCH$_2$(4-MeOC$_6$H$_4$) | — | 560 |
| 62 | S | Me | NHCH$_2$(2,4-Cl$_2$C$_6$H$_3$) | — | 600 |
| 63 | S | Me | NH(CH$_2$)$_2$Ph | — | 544 |
| 64 | S | Me | NHCH$_2$CO$_2$Et | —[5] | 526 |
| 65 | S | Me | NH(CH$_2$)$_2$CO$_2$Et | —[6] | 540 |
| 66 | S | Me | NH(CH$_2$)$_3$CO$_2$Et | —[7] | 554 |

[1] Symbols refer to configurations.
[2] Melting point of a compound of Example 45 was 155-156° C. (recrystallizing solvent: EA/DE).
[3] Melting point of a compound of Example 46-1 was 161-162° C. (recrystallizing solvent: EA).
[4] "F" refers to fumaric acid. Melting point of a compound of Example 50 was 176-178° C. (recrystallizing solvent: E/DE).
[5] Melting point of a compound of Example 64 was 135-137° C. (recrystallizing solvent: E/EA).
[6] Melting point of a compound of Example 65 was 47-149° C. (recrystallizing solvent: E/EA).
[7] Melting point of a compound of Example 66 was 160-162° C. (recrystallizing solvent: E/EA).

1) Symbols refer to configurations.
2) Melting point of a compound of Example 45 was 155-156° C. (recrystallizing solvent: EA/DE).
3) Melting point of a compound of Example 46-1 was 161-162° C. (recrystallizing solvent: EA).
4) "F" refers to fumaric acid. Melting point of a compound of Example 50 was 176-178° C. (recrystallizing solvent: E/DE).
5) Melting point of a compound of Example 64 was 135-137° C. (recrystallizing solvent: E/EA).
6) Melting point of a compound of Example 65 was 147-149° C. (recrystallizing solvent: E/EA).
7) Melting point of a compound of Example 66 was 160-162° C. (recrystallizing solvent: E/EA).

Example 46 (Alternative Method)

Preparation of 4-amino-5-chloro-2-ethoxy-N-[{4-[(1-methylcarbamoyl-4-piperidinyl)methyl]-2-morpholinyl}methyl]benzamide In place of 2-aminomethyl-4-(1-carbamoyl-4-piperidinylmethyl)morpholine of Example 43 (Alternative Method), 2-aminomethyl-4-[(1-methylcarbamoyl-4-piperidinyl)methyl]morpholine (Reference Example 18) was treated in the similar manner to Example 43 (Alternative Method) to give the titled compound as a solid.

$^1$H-NMR (CDCl$_3$, δppm); 0.8-1.2 (2H, m), 1.50 (3H, t, J=7.0 Hz), 1.5-1.8 (3H, m), 1.91 (1H, t, J=10.4 Hz), 2.0-2.3 (3H, m), 2.3-3.0 (4H, m), 2.81 (3H, d, J=4.6 Hz), 3.35 (1H, m), 3.5-3.8 (3H, m), 3.75-4.1 (3H, m), 4.09 (2H, q, J=7.0 Hz), 4.35 (2H, s), 4.4 (1H, m), 6.27 (1H, s), 8.11 (1H, s), 8.22 (1H, t like).

Example 67

Preparation of 4-amino-5-chloro-N-[{4-[(1-dimethylcarbamoyl-4-piperidinyl)methyl]-2-morpholinyl}methyl]-2-methoxybenzamide

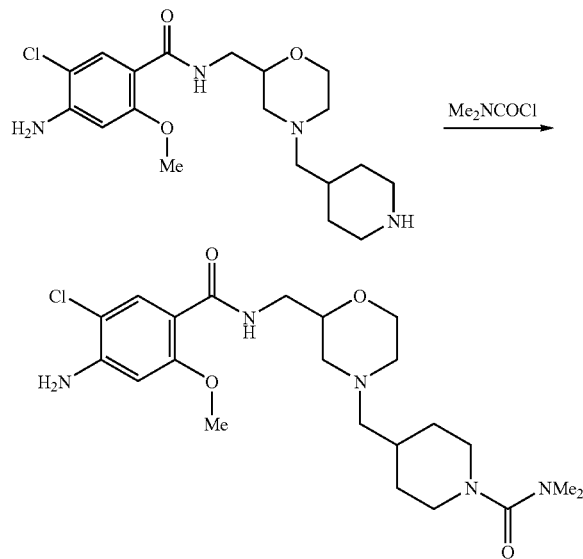

To 4-amino-5-chloro-2-methoxy-N-[{4-(4-piperidinylmethyl)-2-morpholinyl}methyl]-benzamide (Example 23) (1.0 g) and a solution of TEA (0.53 ml) in methylene chloride (20 ml) was added dropwise dimethylcarbamoyl chloride (0.30 g) under ice-cooling. After completion of addition, the internal temperature of the reaction solution was warmed to room temperature, and the solution was stirred for 3 hours. The reaction solution was washed with water, then brine, and then dried over anhydrous magnesium sulfate. The solvent was removed in vacuo. The residue was purified by silica gel column chromatography (eluent: chloroform/methanol=30/1) to give the titled compound (1.1 g) as a white solid. Melting point 179-180° C. (recrystallized from EA)

$^1$H-NMR (CDCl$_3$, δppm); 1.0-1.2 (2H, m), 1.55-1.8 (3H, m), 1.89 (1H, t, J=10.4 Hz), 2.05-2.2 (3H, m), 2.55-2.8 (4H, m), 2.81 (6H, s), 3.33 (1H, m), 3.55-3.75 (5H, m), 3.86 (1H, m), 3.89 (3H, s), 4.37 (2H, br s), 6.29 (1H, s), 8.00 (1H, br t), 8.09 (1H, s). LC-MS, m/z; 468 (MH$^+$).

Examples 68-133

In place of 4-amino-5-chloro-2-methoxy-N-[{4-(4-piperidinylmethyl)-2-morpholinyl}methyl]-benzamide of Example 67, the corresponding amide compounds and the corresponding acid chlorides were treated in the similar manner to Example 67 to give the following compounds of Tables 14 to 16 as an amorphous solid or a powder. Certain amorphous solids were treated with fumaric acid or hydrochloric acid to form a salt.

TABLE 14

| Example*[1] | Y | V | R[1] | R | l | m | n | Q | LC-MS: m/z(MH$^+$)/ mp (Recrystallizing Solvent) |
|---|---|---|---|---|---|---|---|---|---|
| 68 | S | Cl | CH | Me | CONMe$_2$ | 1 | 2 | 1 | — | 468/ 196-197° C. (EA) |
| 69 | R | Cl | CH | Me | CONMe$_2$ | 1 | 2 | 1 | — | 468/ 169° C. (E) |
| 70 | RS | Br | CH | Me | CONMe$_2$ | 1 | 2 | 1 | 3/2F[2] | 514/ 182-183° C. (E) |
| 71 | RS | Cl | CH | Et | CONMe$_2$ | 1 | 2 | 1 | — | 482/ 180-181° C. (E/DE) |
| 72 | S | Cl | CH | Et | CONMe$_2$ | 1 | 2 | 1 | — | 482/ 157-158° C. (EA) |
| 73 | R | Cl | CH | Et | CONMe$_2$ | 1 | 2 | 1 | — | 482/ 153-154° C. (EA/DE) |
| 74 | RS | Br | CH | Et | CONMe$_2$ | 1 | 2 | 1 | F[2] | 528/ 180-182° C.[2] (E) |
| 75 | RS | Cl | CH | Me | CONMe$_2$ | 2 | 2 | 1 | F[2] | 482/ 135-137° C. (E) |
| 76 | RS | Cl | CH | Et | CONMe$_2$ | 1 | 1 | 2 | F[2] | 482/ 110° C. (E/EA) |
| 77 | RS | Cl | CH | Et | CONMe$_2$ | 1 | 1 | 0 | 4/5F[2] | 454/ 158° C. (E) |
| 78 | RS | Cl | CH | Et | CONMe$_2$ | 1 | 1 | 1 | 3/2F[2] | 468/ 169° C.[2] (E) |

TABLE 14-continued

[Structure: Y and H2N substituted pyridine/benzene (V position) with OR¹, connected via amide to CH2-CH*(morpholine-like ring with (CH2)l)-CH2-N-CH2-(pyrrolidine-like ring with (CH2)m and (CH2)n)-N-R, salt ·Q]

| Example *[1] | Y | V | R¹ | R | l | m | n | Q | LC-MS: m/z(MH+)/ mp (Recrystallizing Solvent) |
|---|---|---|---|---|---|---|---|---|---|
| 79 | RS | Cl | CH | Et | CSNMe₂ | 1 | 2 | 1 | — | 498/ 169° C. (E) |
| 80 | S | Cl | CH | Me | SO₂NMe₂ | 1 | 2 | 1 | F[2] | 504/ 132-134° C. (E) |
| 81 | RS | Cl | CH | Et | SO₂NMe₂ | 1 | 2 | 1 | F[2] | 518/ 200° C.[2] (E) |
| 82 | RS | Cl | CH | Pr | CONMe₂ | 1 | 2 | 1 | — | 496/ 148-150° C. (EA) |
| 83 | RS | Cl | CH | ⁱPr | CONMe₂ | 1 | 2 | 1 | 2F[2] | 496/ 170-173° C. (E) |
| 84 | RS | Cl | CH | CH₂CH=CH₂ | CONMe₂ | 1 | 2 | 1 | — | 494/ 69-71° C. (EA) |
| 85 | RS | Cl | N | Me | CONMe₂ | 1 | 2 | 1 | — | 469/ 149-151° C. (EA/DE) |
| 86 | RS | Br | N | Me | CONMe₂ | 1 | 2 | 1 | 3/2F[2] | 515/ 182-183° C. (E) |
| 87 | RS | Cl | CH | Et | CONEt₂ | 1 | 2 | 1 | — | 510/ 178-180° C. (EA/DE) |
| 88 | S | Cl | CH | Me | CONⁱPr₂ | 1 | 2 | 1 | HCl | 524/ 211-213° C. (AN) |
| 89 | S | Cl | CH | Me | [acetyl-pyrrolidine] | 1 | 2 | 1 | — | 494/ 150-152° C. (EA/H) |
| 90 | RS | Cl | CH | Et | [acetyl-pyrrolidine] | 1 | 2 | 1 | 3/2F[2] | 508/ 201-202° C. (E) |
| 91 | RS | Cl | CH | Et | [acetyl-morpholine] | 1 | 2 | 1 | — | 524/ 150-160° C. (E/DE) |
| 92 | S | Cl | CH | Me | CO₂Me | 1 | 2 | 1 | — | 455 |
| 93 | RS | Cl | CH | Et | CO₂Me | 1 | 2 | 1 | F[2] | 469/ 175° C.[2] (E) |
| 94 | S | Cl | CH | Me | SO₂Me | 1 | 2 | 1 | — | 475 |
| 95 | RS | Cl | CH | Et | SO₂Me | 1 | 2 | 1 | — | 489/ 178-179° C. (E) |
| 96 | S | Cl | CH | Me | CO₂Et | 1 | 2 | 1 | — | 469/— |
| 97 | RS | Cl | CH | Me | SO₂Et | 1 | 2 | 1 | — | 489/— |
| 98 | S | Cl | CH | Me | CO₂Pr | 1 | 2 | 1 | — | 483/— |
| 99 | S | Cl | CH | Me | CO₂ⁱPr | 1 | 2 | 1 | — | 483/— |
| 100 | S | Cl | CH | Me | CO₂CH₂CH=CH₂ | 1 | 2 | 1 | — | 481/— |
| 101 | S | Cl | CH | Me | CO₂Bu | 1 | 2 | 1 | — | 497/— |
| 102 | S | Cl | CH | Me | CO₂ⁱBu | 1 | 2 | 1 | — | 497/— |
| 103 | S | Cl | CH | Me | CO₂CH₂ᵗBu | 1 | 2 | 1 | — | 511/— |
| 104 | S | Cl | CH | Me | CO₂(CH₂)₇Me | 1 | 2 | 1 | — | 553/— |

[1] Symbols refer to configurations.
[2] "F" refers to fumaric acid.

TABLE 15

| Example | *[1] | Y | V | R[1] | R | l | m | n | Q | LC-MS: m/z(MH+)/ mp (Recrystallizing Solvent) |
|---|---|---|---|---|---|---|---|---|---|---|
| 105 | S | Cl | CH | Me | CO$_2$(CH$_2$)$_9$Me | 1 | 2 | 1 | — | 581 |
| 106 | S | Cl | CH | Me | CO$_2$Ph | 1 | 2 | 1 | — | 517 |
| 107 | S | Cl | CH | Me | CO$_2$(2-MeOC$_6$H$_4$) | 1 | 2 | 1 | — | 547 |
| 108 | S | Cl | CH | Me | CO$_2$(4-NO$_2$C$_6$H$_4$) | 1 | 2 | 1 | — | 562 |
| 109 | RS | Cl | CH | Et | SO$_2$CH$_2$Ph | 1 | 2 | 1 | 3/2F[2] | 565/ 194-198° C. (E) |
| 110 | S | Cl | CH | Me | COCO$_2$Et | 1 | 2 | 1 | F[2] | 497/ 134-136° C. (E) |
| 111 | RS | Cl | CH | Me | COMe | 1 | 2 | 1 | F[2] | 439/ 150-152° C. (IP) |
| 112 | RS | Cl | CH | Et | COPh | 1 | 2 | 1 | — | 515/ 198-200° C. (E/EA) |
| 113 | S | Cl | CH | Me | CO(3-FC$_6$H$_4$) | 1 | 2 | 1 | — | 519 |
| 114 | RS | Cl | CH | Et | CO(3-FC$_6$H$_4$) | 1 | 2 | 1 | — | 533/ 183-185° C. (E/DE) |
| 115 | S | Cl | CH | Me | CO(4-ClC$_6$H$_4$) | 1 | 2 | 1 | — | 537 |
| 116 | S | Cl | CH | Et | CO(4-ClC$_6$H$_4$) | 1 | 2 | 1 | — | 551 |
| 117 | S | Cl | CH | Me | CO(3-BrC$_6$H$_4$) | 1 | 2 | 1 | — | 581 |
| 118 | S | Cl | CH | Me | CO(2-MeC$_6$H$_4$) | 1 | 2 | 1 | — | 515 |
| 119 | S | Cl | CH | Me | CO(3-MeC$_6$H$_4$) | 1 | 2 | 1 | — | 515 |
| 120 | S | Cl | CH | Me | CO(4-MeC$_6$H$_4$) | 1 | 2 | 1 | — | 515 |
| 121 | S | Cl | CH | Et | CO(4-MeC$_6$H$_4$) | 1 | 2 | 1 | — | 529 |
| 122 | S | Cl | CH | Me | CO(4-EtC$_6$H$_4$) | 1 | 2 | 1 | — | 529 |
| 123 | S | Cl | CH | Me | CO(4-$^t$BuC$_6$H$_4$) | 1 | 2 | 1 | — | 557 |
| 124 | S | Cl | CH | Me | CO(3-MeOC$_6$H$_4$) | 1 | 2 | 1 | — | 531 |
| 125 | S | Cl | CH | Me | CO(4-MeOC$_6$H$_4$) | 1 | 2 | 1 | — | 531 |
| 126 | S | Cl | CH | Et | CO(4-MeOC$_6$H$_4$) | 1 | 2 | 1 | — | 545 |

[1] Symbols refer to configurations.
[2] "F" refers to fumaric acid.

TABLE 16

| Example | *[1] | Y | V | R[1] | R | l | m | n | Q | LC-MS: m/z(MH+)/mp (Recrystallizing Solvent) |
|---|---|---|---|---|---|---|---|---|---|---|
| 127 | S | Cl | CH | Me | COCH$_2$OAc | 1 | 2 | 1 | — | 497 |
| 128 | RS | Cl | CH | Et | COCH$_2$OAc | 1 | 2 | 1 | ½F[1] | 511/ 182° C.[3] (E) |
| 129 | S | Cl | CH | Et | COCH$_2$OAc | 1 | 2 | 1 | — | 511 |
| 130 | RS | Cl | CH | Et | COCMe$_2$OAc | 1 | 2 | 1 | F[1] | 539/ 160° C. (E) |
| 131 | S | Cl | CH | Me | 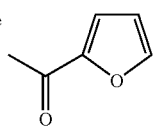 | 1 | 2 | 1 | — | 491 |
| 132 | S | Cl | CH | Me | COCH$_2$OMe | 1 | 2 | 1 | — | 469 |
| 133 | S | Cl | CH | Et | COCH$_2$OMe | 1 | 2 | 1 | — | 483 |

[1] Symbols refer to configurations.
[2] "F" refers to fumaric acid.
[3] Values refer to a collapse temperature.

Examples 134-141

In place of 4-amino-5-chloro-2-methoxy-N-[{4-(4-piperidinylmethyl)-2-morpholinyl}methyl]-benzamide of Example 67, racemic or optically-active 4-amino-5-chloro-N-[{4-(4-piperidinylmethyl)-2-morpholinyl}methyl]-2,3-dihydrobenzo[b]furan-7-carboxamide and the corresponding acid chlorides were treated in the similar manner to Example 67 to give the following compounds of Table 17 as an amorphous form or a solid. Certain amorphous solids were treated with fumaric acid to form a salt.

TABLE 17

[Structure: 5-chloro-6-amino-2,3-dihydrobenzofuran-7-carboxamide with morpholinylmethyl-piperidinyl-N-R, ·Q]

| Example | *[1] | R | Q | LC-MS: m/z(MH+)/ mp (Recrystallizing Solvent) |
|---|---|---|---|---|
| 134 | RS | [acetyl-pyrrolidine: C(O)-N-pyrrolidinyl] | — | 506 |
| 135 | RS | CONMe$_2$ | ½F[2] | 480/ 183-184° C. (E) |
| 136 | S | CONMe$_2$ | — | 480/ 145-148° C. (EA/DE) |
| 137 | R | CONMe$_2$ | — | 480/ 142-146° C. (EA/DE) |

TABLE 17-continued

| Example | *[1] | R | Q | LC-MS: m/z(MH+)/ mp (Recrystallizing Solvent) |
|---|---|---|---|---|
| 138 | RS | CO$_2$Me | — | 467 |
| 139 | RS | COMe | — | 451 |
| 140 | RS | SO$_2$Me | — | 487 |
| 141 | RS | COCH$_2$OAc | — | 509 |

[1]Symbols refer to configurations.
[2]"F" refers to fumaric acid.

Compounds of Example 70, Example 71, Example 82, Example 83, Example 84, Example 85 and Example 86 were prepared according to Alternative Method (a method described in Example 43 (Alternative Method)) to give a solid. The data is shown in Table 18.

TABLE 18

[Structure: R-C(O)-NH-CH$_2$-morpholinyl-CH$_2$-piperidinyl-C(O)-NMe$_2$]

| Example | Compound Name | R— | $^1$H—NMR |
|---|---|---|---|
| 70 (Alternative) | 4-amino-5-bromo-N-[{4-[(1-dimethylcarbamoyl-4-piperidinyl)methyl]-2-morpholinyl}methyl]-2-methoxybenzamide 1.5 fumarate | [Br, H$_2$N, OMe-substituted phenyl] | (DMSO-d$_6$, δ ppm); 0.9-1.15 (2H, m), 1.65 (3H, br d, J = 10.8 Hz), 1.78 (1H, t, J = 10.7 Hz), 2.00 (1H, br t, J = 11.6 Hz), 2.14 (2H, br d, J = 6.6 Hz), 2.4-2.9 (5H, m), 2.68 (6H, s), 3.0-4.0 (6H, m), 3.81 (3H, s), 5.89 (2H, s), 6.47 (1H, s), 6.61 (3H, s), 7.82 (1H, s), 7.96 (1H, t like, J = 5.3 Hz). |
| 71 (Alternative) | 4-amino-5-chloro-N-[{4-[(1-dimethylcarbamoyl-4-piperidinyl)methyl]-2-morpholinyl}methyl]-2-ethoxybenzamide | [Cl, H$_2$N, OEt-substituted phenyl] | (CDCl$_3$, δ ppm); 1.0-1.25 (2H, m), 1.50 (3H, t, J = 6.9 Hz), 1.55-1.8 (3H, m), 1.91 (1H, br t, J = 10.5 Hz), 2.05-2.25 (3H, m), 2.55-2.85 (4H, m), 2.81 (6H, s), 3.35 (1H, m), 3.55-3.8 (5H, m), 3.86 (1H, m), 4.09 (2H, s), 4.33 (2H, br d like), 6.27 (1H, s), 8.11 (1H, s), 8.22 (1H, t like). |
| 82 (Alternative) | 4-amino-5-chloro-N-[{4-[(1-dimethylcarbamoyl-4-piperidinyl)methyl]-2-morpholinyl}methyl]-2-propoxybenzamide | [Cl, H$_2$N, OPr-substituted phenyl] | (CDCl$_3$, δ ppm); 1.06 (3H, t, J = 7.4 Hz), 1.0-1.25 (2H, m), 1.5-1.8 (3H, m), 1.90 (2H, sex, J = 7.0 Hz), 2.05-2.25 (3H, m), 2.55-2.85 (5H, m), 2.81 (6H, s), 3.35 (1H, m), 3.55-3.75 (5H, m), 3.85 (1H, br d like, J = 11.5 Hz), 3.99 (2H, td, J = 1.8, 6.4 Hz), 4.34 (2H, br d like), 6.28 (1H, s), 8.11 (1H, s), 8.18 (1H, t like). |

TABLE 18-continued

[Structure: R-C(O)-NH-CH2-morpholine-N-CH2-piperidine-N-C(O)-NMe2]

| Example | Compound Name | R— | ¹H—NMR |
|---|---|---|---|
| 83 (Alternative) | 4-amino-5-chloro-N-[{4-[(1-dimethylcarbamoyl-4-piperidinyl)methyl]-2-morpholinyl}methyl]-2-isopropoxybenzamide fumarate | [Cl, Me, H2N, OiPr substituted benzene] | (DMSO-d₆, δ ppm); 0.95-1.15 (3H, m), 1.33 (6H, d, J = 5.7 Hz), 1.65 (3H, br d like, J = 10.4 Hz), 1.79 (1H, t, J = 10.0 Hz), 2.00 (2H, t like, J = 9.8 Hz), 2.0-2.3 (2H, m), 2.5-2.8 (5H, m), 2.69 (6H, s), 2.8-4.0 (3H, m), 3.80 (1H, br d, J = 9.9 Hz), 4.61 (1H, m), 5.89 (2H, s), 6.51 (1H, s), 6.61 (4H, s), 7.71 (1H, s), 8.12 (1H, br t like). |
| 84 (Alternative) | 2-allyloxy-4-amino-5-chloro-N-[{4-[(1-dimethylcarbamoyl-4-piperidinyl)methyl]-2-morpholinyl}methyl]benzamide | [Cl, Me, H2N, O-CH2-CH=CH2 substituted benzene] | (CDCl₃, δ ppm); 1.05-1.25 (2H, m), 1.6-1.75 (2H, m), 1.90 (1H, t, J = 10.4 Hz), 2.05-2.25 (2H, m), 2.6-2.85 (5H, m), 2.81 (6H, s), 3.35 (1H, m), 3.6-3.75 (5H, m), 3.86 (1H, m), 4.35 (2H, s), 4.59 (2H, d, J = 5.7 Hz), 5.36 (1H, d, J = 10.4 Hz), 5.45 (1H, d, J = 17.0 Hz), 6.1 (1H, m), 6.28 (1H, s), 8.10 (1H, br t like), 8.11 (1H, s). |
| 85 (Alternative) | 6-amino-5-chloro-N-[{4-[(1-dimethylcarbamoyl-4-piperidinyl)methyl]-2-morpholinyl}methyl]-2-methoxypyridine-3-carboxamide | [Cl, Me, H2N, OMe substituted pyridine] | (CDCl₃, δ ppm); 1.0-1.25 (2H, m), 1.5-1.8 (5H, m), 1.88 (1H, t, J = 10.5 Hz), 2.0-2.25 (3H, m), 2.7 (1H, m), 2.81 (6H, s), 3.3 (1H, m), 3.5-3.8 (6H, m), 3.88 (1H, d, J = 11.2 Hz), 3.98 (3H, s), 5.06 (2H, br s), 8.11 (1H, br t), 8.29 (1H, s). |
| 86 (Alternative) | 6-amino-5-bromo-N-[{4-[(1-dimethylcarbamoyl-4-piperidinyl)methyl]-2-morpholinyl}methyl]-2-methoxypyridine-3-carboxamide 1.5 fumarate | [Br, Me, H2N, OMe substituted pyridine] | (DMSO-d₆, δ ppm); 0.9-1.15 (2H, m), 1.65 (3H, br d, J = 10.8 Hz), 1.78 (1H, t, J = 10.7 Hz), 2.00 (1H, br t, J = 11.6 Hz), 2.14 (2H, br d, J = 6.6 Hz), 2.4-2.9 (5H, m), 2.68 (6H, s), 3.0-4.0 (6H, m), 3.81 (3H, s), 5.89 (2H, s), 6.47 (1H, s), 6.61 (3H, s), 7.82 (1H, s), 7.96 (1H, t like, J = 5.3 Hz). |

Example 90 (Alternative Method)

Preparation of 4-amino-5-chloro-2-ethoxy-N-[{4-[(1-(1-pyrrolidinecarbonyl)-4-piperidinyl)-methyl]-2-morpholinyl}methyl]benzamide 1.5 fumarate

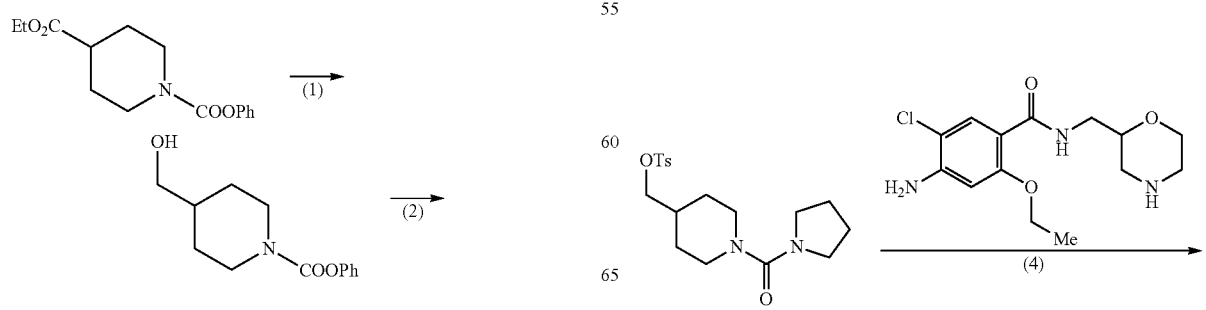

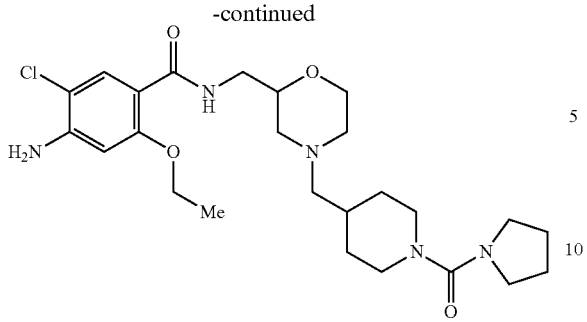

(1) To an anhydrous THF (1500 ml) were added calcium chloride (110.9 g), sodium borohydride (75.6 g), and sequentially ethyl 1-phenoxycarbonyl-4-piperidinecarboxylic acid (300 g), and then the internal temperature of the mixture was cooled to 10° C. or below. To the mixture was slowly added dropwise ethanol (1000 ml), and after completion of addition, the mixture was stirred about 20 hours under ice-cooling. The reaction solution which rose to room temperature was ice-cooled again, and thereto was gradually added dropwise 18% cooled hydrochloric acid so that the solution became acidic. The reaction solution in which an insoluble was precipitated was filtered through Celite® to remove the insoluble, and then the solvent was removed in vacuo. To the residue was added water, and the mixture was extracted with chloroform. The extract was sequentially washed with water, 2N aqueous sodium hydroxide solution, water and brine, and then dried over anhydrous magnesium sulfate. The solvent was removed in vacuo to give 1-phenoxycarbonyl-4-piperidine-methanol (232 g) as a pale yellow oil. The oil was used in the next step without any purification. LC-MS, m/z; 236 (MH$^+$).

(2) A mixture of the above product (232 g) and pyrrolidine (1200 ml) was heated to reflux for 6 hours with stirring. After cooling to room temperature, the reaction solution was dried under reduced pressure to be solidified. The residue was dissolved in chloroform, washed with water, 2N hydrochloric acid, 2N aqueous sodium hydroxide solution, water, then brine, and then dried over anhydrous magnesium sulfate. The solvent was removed in vacuo to give 1-pyrrolidinecarbonyl-4-piperidinemethanol (183.5 g) as a light brown oil. The oil was used in the next step without any purification. LC-MS, m/z; 213 (MH$^+$).

(3) To a solution of the above product (183.5 g), 4-dimethylaminopyridine (2.1 g) and TEA (131.1 g) in methylene chloride (1000 ml) was gradually added p-toluenesulfonyl chloride (198 g) at room temperature, and after completion of addition, the mixture was stirred for 2 days. The reaction solution was sequentially washed with water, 2N hydrochloric acid, 2N aqueous sodium hydroxide solution, water and brine, and then dried over anhydrous magnesium sulfate. The solvent was removed in vacuo to give 1-pyrrolidinecarbonyl-4-(p-toluenesulfonyloxymethyl)piperidine (215 g) as a light brown solid. LC-MS, m/z; 367 (MH$^+$).

(4) A mixture of the above product (2.34 g), 4-amino-5-chloro-2-ethoxy-N-(2-morpholinylmethyl)benzamide (S. Kato, et al., Chem. Pharm, Bull., (1995) 43, 699-702) (2.0 g), anhydrous potassium carbonate (1.3 g), potassium iodide (0.1 g) and acetonitrile (80 ml) was heated to reflux for 23 hours with stirring. After cooling to room temperature, the reaction solution was dried under reduced pressure to be solidified, and to the residue was added water and the mixture was extracted with chloroform. The extract was washed with brine and dried over anhydrous magnesium sulfate, and the solvent was removed in vacuo. The residue was purified by silica gel column chromatography (eluent: chloroform/methanol=19/1 to 9/1) to give an amorphous solid which was further treated with fumaric acid to give the titled compound (0.7 g) as a powder.

$^1$H-NMR (DMSO-d$_6$, δppm); 0.96-1.08 (2H, m), 1.41 (3H, t, J=6.9 Hz), 1.6-1.8 (7H, m), 1.8 (1H, t, J=10.5 Hz), 2.04 (1H, t like), 2.16 (2H, d like, J=6.4 Hz), 2.64-2.85 (4H, m), 3.2-3.3 (5H, m), 3.4-3.65 (5H, m), 3.81 (1H, d, J=11 Hz), 4.07 (2H, q, J=6.9 Hz), 5.95 (2H, s), 6.47 (1H, s), 6.62 (3H, s), 7.71 (1H, s), 8.07 (1H, t, J=5.1 Hz).

A compound of Example 135 was prepared according to Alternative Method (a method described in Example 43 (Alternative Method)) as a solid. The data is shown in Table 19.

TABLE 19

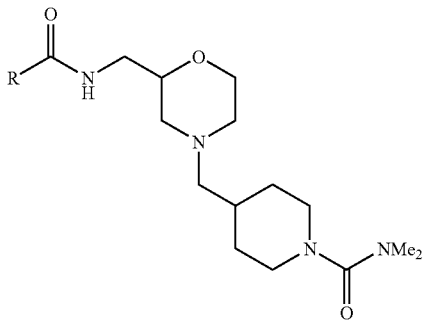

| Example | Compound Name | R— | $^1$H—NMR |
|---|---|---|---|
| 135 (Alternative) | 4-amino-5-chloro-N-[{4-[(1-dimethylcarbamoyl-4-piperidinyl)methyl]-2-morpholinyl}methyl]-2,3-dihydrobenzo[b]furan-7-carboxamide 1.5 fumarate | 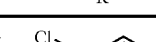 | (DMSO-d$_6$, δ ppm); 0.9-1.15 (2H, m), 1.65 (3H, br d, J = 10.6 Hz), 1.76 (1H, t, J = 10.7 Hz), 1.99 (1H, br t, J = 9.9 Hz), 2.13 (2H, br d, J = 6.6 Hz), 2.5-2.75 (4H, m), 2.68 (6H, s), 3.02 (2H, t, J = 8.8 Hz), 3.2 (1H, m), 3.3-3.7 (5H, m), 3.78 (1H, br d, J = 11.2 Hz), 4.71 (2H, t, J = 8.8 Hz), 5.88 (2H, s), 6.61 (2H, s), 7.45 (1H, s), 7.50 (1H, t like, J = 5.6 Hz). |

Example 139 (Alternative Method)

Preparation of N-[{4-(1-acetyl-4-piperidinylmethyl)-2-morpholinyl}methyl]-4-amino-5-chloro-2,3-dihydrobenzo[b]furan-7-carboxamide

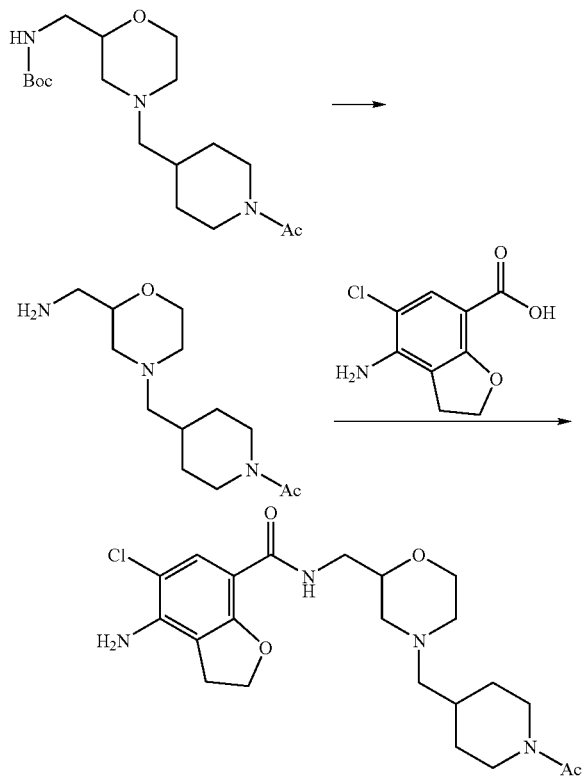

To a solution of 4-(1-acetyl-4-piperidinylmethyl)-2-(tert-butoxycarbonyl)-aminomethylmorpholine (Reference Example 15) (0.70 g) in methylene chloride (5 ml) was added trifluoroacetic acid (5 ml), and the mixture was stirred at room temperature for 2 hours. The reaction solution was dried under reduced pressure to be solidified, and the residue was dissolved in toluene, and then dried under reduced pressure to be solidified again. To the residue was added water, and the mixture was alkalified with 2N aqueous sodium hydroxide and extracted with chloroform. The extract was washed with water, then brine, and then dried over anhydrous magnesium sulfate. The solvent was removed in vacuo. A solution of the oily residue in DMF (5 ml) containing 4-(1-acetyl-4-piperidinylmethyl)-2-aminomethylmorpholine was added to a reaction solution which was obtained by stirring a solution of 4-amino-5-chloro-2, 3-dihydrobenzo[b]furan-7-carboxylic acid (0.42 g) and N,N'-carbonyldiimidazole (0.35 g) in DMF (10 ml) at room temperature for 1 hour. The mixture was stirred at room temperature overnight. To the reaction solution was added water, and the mixture was extracted with chloroform, and then the extract was sequentially washed with saturated sodium bicarbonate, water and brine, and dried over anhydrous magnesium sulfate. The solvent was removed in vacuo. The residue was purified by silica gel column chromatography (eluent: chloroform/methanol=30/1) to give the titled compound (0.85 g) as a white amorphous solid.

$^1$H-NMR (CDCl$_3$, δppm); 0.95-1.2 (2H, m), 1.6-2.0 (5H, m), 2.08 (3H, s), 2.16 (2H, d, J=6.8 Hz), 2.45-2.7 (2H, m), 2.75 (1H, m), 3.0 (1H, m), 3.06 (2H, t, J=8.8 Hz), 3.35 (1H, m), 3.55-3.75 (3H, m), 3.79 (1H, br d, J=13.5 Hz), 3.87 (1H, br d, J=10.4 Hz), 4.29 (2H, s), 4.58 (1H, br d, J=13.0 Hz), 4.78 (2H, t, J=8.8 Hz), 7.62 (1H, br t like), 7.85 (1H, s).

Example 142

Preparation of 4-amino-5-chloro-2-ethoxy-N-[{4-[(1-ethoxyacetyl-4-piperidinyl)methyl]-2-morpholinyl}methyl]benzamide 1.5 fumarate

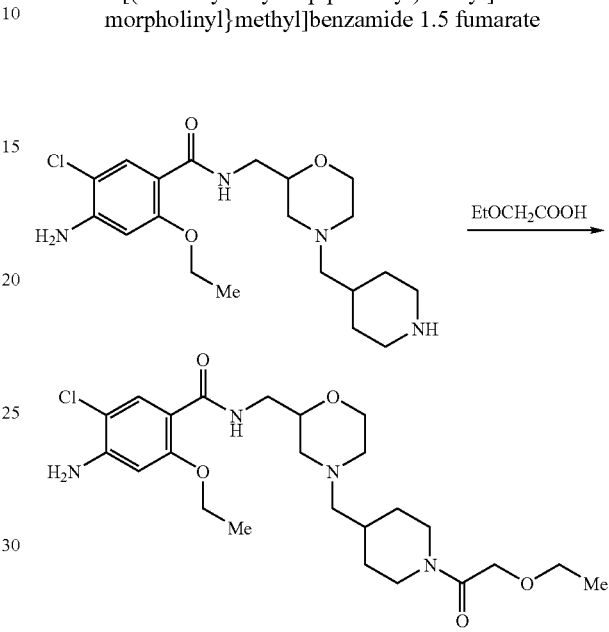

A solution of 4-amino-5-chloro-2-ethoxy-N-[{4-(4-piperidinylmethyl)-2-morpholinyl}methyl]-benzamide (Example 22) (1.0 g), ethoxyacetic acid (0.25 g) and 1-ethyl-3-(3-dimethylaminopropyl)carbodiimide hydrochloride (0.56 g) in methylene chloride (10 ml) was stirred at room temperature for 1 hour. The reaction solution was washed with water, then brine, and then dried over anhydrous magnesium sulfate. The solvent was removed in vacuo. The residue was purified by silica gel column chromatography (eluent: chloroform/methanol=10/1) to give a base of the titled compound (1.05 g) as a white amorphous solid. The solid was treated with fumaric acid to give the titled compound as a powder. Melting point 149° C. (degradation, recrystallized from E/EA)

$^1$H-NMR (DMSO-d$_6$, δppm); 0.8-1.2 (2H, m), 1.11 (3H, t, J=7.0 Hz), 1.41 (3H, t, J=6.9 Hz), 1.6-1.8 (4H, m), 2.03 (1H, dd, J=8.2, 11.4 Hz), 2.14 (2H, d like, J=6.6 Hz), 2.67 (1H, d, J=10.9 Hz), 2.77 (1H, d, J=10.9 Hz), 2.93 (1H, t like, J=12.4 Hz), 3.25 (1H, m), 3.35-3.65 (6H, m), 3.80 (2H, br t, J=11.8 Hz), 3.95-4.2 (4H, m), 4.29 (1H, br t, J=11.2 Hz), 5.94 (2H, s), 6.47 (1H, s), 6.63 (3H, s), 7.71 (1H, s), 8.07 (1H, t like, J=5.0 Hz). LC-MS, m/z; 497 (MH$^+$).

Examples 143-189

The corresponding starting compounds in place of 4-amino-5-chloro-2-methoxy-N-[{4-(4-piperidinylmethyl)-2-morpholinyl}methyl]benzamide of Example 142 and the corresponding carboxylic acids in place of ethoxyacetic acid were treated in the similar manner to Example 142 to give compounds of Tables 20 to 23 as an amorphous solid or a powder. Certain amorphous solids were treated with fumaric acid to form a salt.

TABLE 20

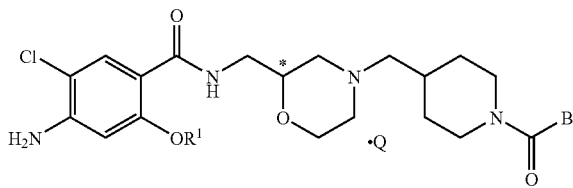

| Example | *1) | R1 | B | Q | LC-MS: m/z(MH+) |
|---|---|---|---|---|---|
| 143 | S | Et | CH$_2$OEt | — | 497 |
| 144 | S | Me | CH$_2$OEt | — | 483 |
| 145 | S | Me | CH$_2$NHAc | — | 496 |
| 146 | S | Et | CH$_2$NHAc | — | 510 |
| 147 | S | Me | CH$_2$NMe$_2$ | — | 482 |
| 148 | S | Me | (CH$_2$)$_2$CONH$_2$ | — | 496 |
| 149 | S | Me | (CH$_2$)$_2$CO$_2$Me | — | 511 |
| 150 | S | Me | (CH$_2$)$_2$CO$_2$Et | — | 525 |
| 151 | S | Me | (CH$_2$)$_2$NEt$_2$ | — | 524 |

TABLE 20-continued

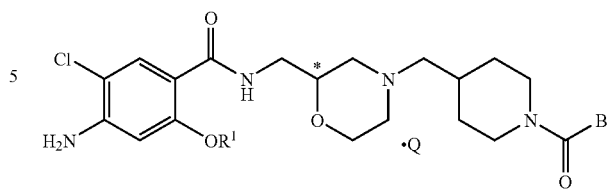

| Example | *1) | R1 | B | Q | LC-MS: m/z(MH+) |
|---|---|---|---|---|---|
| 152 | S | Me |  | — | 536 |
| 153 | S | Me | (CH$_2$)$_3$NHBoc | — | 582 |
| 154 | S | Me | (CH$_2$)$_3$NMe$_2$ | — | 510 |

1) Symbols refer to configurations.

TABLE 21

| Example | *1) | R1 | B | Q | LC-MS: m/z(MH+)/ mp (Recrystallizing Solvent) |
|---|---|---|---|---|---|
| 155 | RS | Et | 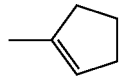 | — | 505/ 169° C. (E/EA) |
| 156 | RS | Et | CMe=CH$_2$ | ½F$^{2)}$ | 479/ 185-187° C.$^{2)}$ (E/EA) |
| 157 | RS | Et | 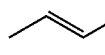 | ½F$^{2)}$ | 505/ 193° C.$^{2)}$ (E) |
| 158 | RS | Et | 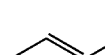 | ½F$^{2)}$ | 531/ 181-183° C. (E/A) |
| 159 | RS | Et | 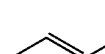 | — | 547/ 208° C. (E) |
| 160 | RS | Et | CH$_2$CH=CH$_2$ | ⅔F$^{2)}$ | 479/ 97-99° C. (E/EA) |
| 161 | RS | Et | (CH$_2$)$_2$CH=CH$_2$ | F$^{1)}$ | 493/ 92-95° C. (E) |
| 162 | RS | Et | (CH$_2$)$_4$CH=CH$_2$ | ½F$^{2)}$ | 521/ 135° C. (E/EA) |
| 163 | RS | Et | CH=CHCH=CH$_2$ | ½F$^{2)}$ | 491/ 175° C. (E) |
| 164 | RS | Et | CH=CH(CH$_2$)$_2$CH=CH$_2$ | ⅔F$^{2)}$ | 519/ 145° C.$^{3)}$ (E/EA) |
| 165 | RS | Et |  —≡—Me | F$^{2)}$ | 477/ 120° C. (E/EA) |
| 166 | S | Me | 2-AcOC$_6$H$_4$ | — | 559 |
| 167 | S | Et | 2-AcOC$_6$H$_4$ | — | 573 |
| 168 | S | Me | 3-AcOC$_6$H$_4$ | — | 559 |
| 169 | S | Me | 4-AcOC$_6$H$_4$ | — | 559 |
| 170 | S | Me | 2-PhOC$_6$H$_4$ | — | 593 |
| 171 | S | Me | 3-Me$_2$NC$_6$H$_4$ | — | 544 |
| 172 | S | Me | 4-Me$_2$NC$_6$H$_4$ | — | 544 |
| 173 | S | Me | 4-AcNHC$_6$H$_4$ | — | 558 |

1) Symbols refer to configurations.
2) "F" refers to fumaric acid.
3) A value refers to a decomposition point.

TABLE 22

| Example | *1) | R¹ | B | Q | LC-MS: m/z(MH⁺)/ mp (Recrystallizing Solvent) |
|---|---|---|---|---|---|
| 174 | S | Me | 4-CO₂MeC₆H₄ | — | 559 |
| 175 | S | Me | 4-PhC₆H₄ | — | 577 |
| 176 | S | Me | 3-Cl-4-NH₂C₆H₃ | — | 552 |
| 177 | S | Me | 2,3-dihydrobenzofuran-7-yl | — | 543 |
| 178 | S | Me | 2,5-dimethylthien-yl | — | 521 |
| 179 | S | Me | 1,2-dimethylpyrrol-yl | — | 504 |
| 180 | S | Me | (S)-tetrahydrofuran-2-yl | — | 495 |
| 181 | RS | Et | (S)-tetrahydrofuran-2-yl | ½F²⁾ | 509/ 168° C.³⁾ (E/EA) |
| 182 | S | Me | (R)-tetrahydrofuran-2-yl | — | 495/ 185-187° C. (EA/DIP) |
| 183 | RS | Et | (R)-tetrahydrofuran-2-yl | ½F²⁾ | 509/ 169° C. (E/EA) |
| 184 | S | Me | (S)-1-Boc-pyrrolidin-2-yl | — | 594 |
| 185 | S | Me | (R)-1-Boc-pyrrolidin-2-yl | — | 594 |
| 186 | S | Me | 1-Boc-3-methylpyrrolidinyl | — | 594 |

1) Symbols refer to configurations.
2) "F" refers to fumaric acid.
3) A value refers to a decomposition point.

TABLE 23

| Example | *1) | R¹ | B | Q | LC-MS: m/z(MH⁺) |
|---|---|---|---|---|---|
| 187 | S | Me | 4-(N-Boc-piperidinyl) | — | 608 |
| 188 | S | Me | 4-(N-Boc-piperidinyl)methyl | — | 622 |
| 189 | S | Me | 1-Me-piperidin-4-yl | — | 522 |

1) Symbols refer to configurations.

Examples 190-195

In place of 4-amino-N-[{4-[(1-(tert-butoxycarbonyl)-4-piperidinyl)methyl]-2-morpholinyl}-methyl]-5-chloro-2-ethoxybenzamide of Example 22, the corresponding starting compounds were treated in the similar manner to Example 22 to give the following compounds of Table 24 as an amorphous solid.

TABLE 24

| Example | B | LC-MS: m/z (MH⁺) |
|---|---|---|
| 190 | (S)-2-methylpyrrolidinyl | 494 |
| 191 | (R)-2-methylpyrrolidinyl | 494 |
| 192 | 3-methylpyrrolidinyl | 494 |
| 193 | 4-methylpiperidinyl | 508 |
| 194 | 4-ethylpiperidinyl | 522 |
| 195 | (CH₂)₃NH₂ | 482 |

Example 196

Preparation of 4-amino-5-chloro-2-ethoxy-N-[{4-[(1-hydroxyacetyl-4-piperidinyl)methyl]-2-morpholinyl}methyl]benzamide fumarate

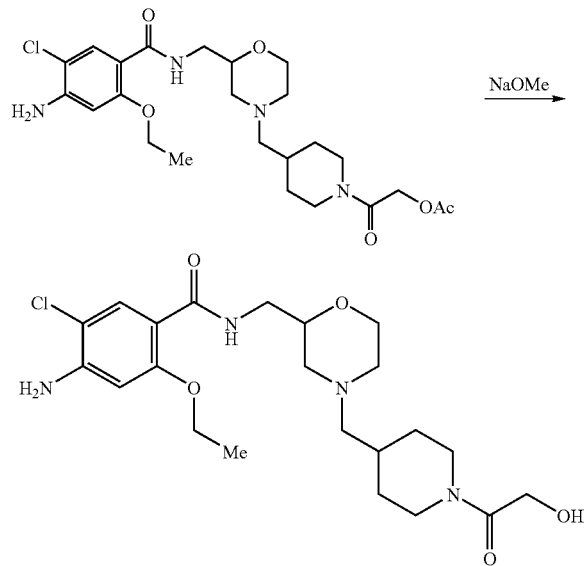

To a solution of N-[{4-[(1-acetoxyacetyl-4-piperidinyl)methyl]-2-morpholinyl}methyl]-4-amino-5-chloro-2-ethoxybenzamide (Example 128) (1.0 g) in methanol (10 ml) was added 28% sodium methoxide methanol solution (0.19 ml) at room temperature, and the mixture was stirred at room temperature for 3 hours. The reaction solution was dried under reduced pressure to be solidified. The residue was dissolved in chloroform, and then washed with water, then brine. The organic layer was dried over anhydrous magnesium sulfate, and the solvent was removed in vacuo. The residue was purified by silica gel column chromatography (eluent: chloroform/methanol=10/1) to give a base of the titled compound (0.82 g) as a white amorphous solid. The solid was treated with fumaric acid to give the titled compound as a powder. Melting point 195° C. (degradation, recrystallized from E)

$^1$H-NMR (DMSO-$d_6$, δppm); 0.8-1.2 (2H, m), 1.41 (3H, t, J=7.0 Hz), 1.6-1.8 (4H, m), 2.01 (1H, td, J=8.3, 2.9 Hz), 2.13 (2H, br d, J=6.8 Hz), 2.64 (1H, br t, J=13.0 Hz), 2.76 (1H, br d, J=11.5 Hz), 2.90 (2H, br t, J=12.5 Hz), 3.2 (1H, m), 3.35-3.7 (4H, m), 3.81 (1H, br d, J=11.5 Hz), 3.95-4.1 (4H, m), 4.31 (1H, br d, J=12.6 Hz), 4.4 (1H, br s), 5.94 (2H, s), 6.47 (1H, s), 6.63 (2H, s), 7.71 (1H, s), 8.07 (1H, t like, J=5.1 Hz). LC-MS, m/z; 469 (MH$^+$).

Examples 197-202

In place of N-[{4-[(1-acetoxyacetyl-4-piperidinyl)methyl]-2-morpholinyl}methyl]-4-amino-5-chloro-2-ethoxybenzamide of Example 196, the corresponding starting compounds were treated in the similar manner to Example 196 to give the following compounds of Table 25 as an amorphous solid. Certain amorphous solids were treated with hydrochloric acid or fumaric acid to form a salt.

TABLE 25

| Example | *[1] | R$^1$ | B | Q | LC-MS: m/z(MH$^+$)/ mp (Recrystallizing Solvent) |
|---|---|---|---|---|---|
| 197 | S | Et | CH$_2$OH | — | 469 |
| 198 | S | Me | CH$_2$OH | HCl | 455/ 164-167° C. (A) |
| 199 | RS | Et | CMe$_2$OH | F[2] | 497/ 142° C. (E) |
| 200 | S | Me | (CH$_2$)$_2$CO$_2$H | — | 497 |
| 201 | S | Me | 3-HOC$_6$H$_4$ | — | 517 |
| 202 | S | Me | 4-HOC$_6$H$_4$ | — | 517 |

[1] Symbols refer to configurations.
[2] "F" refers to fumaric acid.

Example 198 (Alternative Method)

Preparation of 4-amino-5-chloro-N-[{4-[(1-hydroxyacetyl-4-piperidinyl)methyl]-2-morpholinyl}methyl]-2-methoxybenzamide hydrochloride

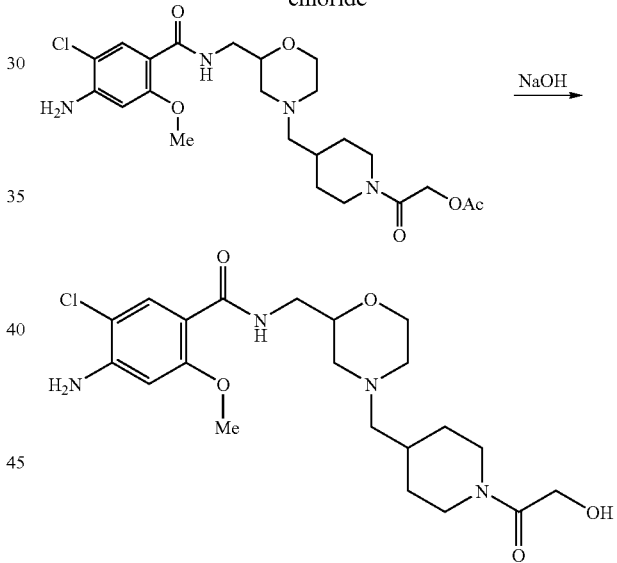

To a solution of N-[{4-[(1-acetoxyacetyl-4-piperidinyl)methyl]-2-morpholinyl}methyl]-4-amino-5-chloro-2-methoxybenzamide (Example 127) (6.6 g) in methanol (25 ml) was added 2N aqueous sodium hydroxide solution (6.7 ml) at room temperature, and the mixture was stirred at room temperature for 30 minutes. The reaction solution was dried under reduced pressure to be solidified, and the residue was dissolved in chloroform, and then washed with saturated sodium bicarbonate aqueous solution, then water. The organic layer was dried over anhydrous magnesium sulfate, and the solvent was removed in vacuo. The residue was purified by silica gel column chromatography (eluent: chloroform/methanol=10/1) to give a base of the titled compound (5.1 g) as a white amorphous solid. The solid was treated with 4N HCl ethyl acetate to give the titled compound as a powder. Melting point 164-167° C. (degradation)

$^1$H-NMR (DMSO-$d_6$, δppm); 0.97-1.20 (2H, m), 2.01 (2H, m), 2.13 (1H, m), 2.63 (1H, br t, J=12.0 Hz), 2.77 (1H, br q, J=11.2 Hz), 2.90-3.10 (4H, m), 3.27-3.62 (6H, m), 3.62 (1H, br d, J=13.2 Hz), 3.84 (3H, s), 3.84-4.12 (3H, m), 4.06 (2H, d, J=7.1 Hz), 4.31 (1H, br d, J=11.5 Hz), 6.02 (2H, s), 6.49 (1H, s), 7.70 (1H, s), 8.09 (1H, t like, J=7.7 Hz). LC-MS, m/z; 455 (MH$^+$).

Example 203

Preparation of 4-amino-5-chloro-N-[{4-[(1-hydroxyacetyl-4-piperidinyl)methyl]-2-morpholinyl}methyl]-2,3-dihydrobenzo[b]furan-7-carboxamide

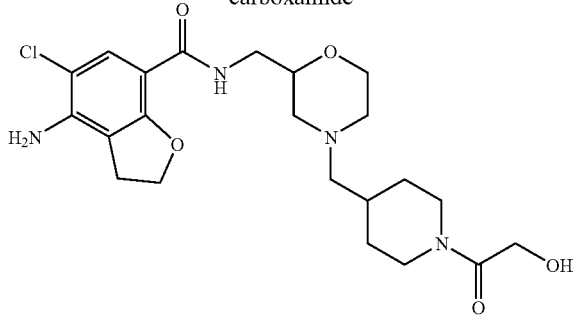

In place of N-[{4-[(1-acetoxyacetyl-4-piperidinyl)methyl]-2-morpholinyl}methyl]-4-amino-5-chloro-2-ethoxybenzamide of Example 196, N-[{4-[(1-acetoxyacetyl-4-piperidinyl)methyl]-2-morpholinyl}methyl]-4-amino-5-chloro-2,3-dihydrobenzo[b]furan-7-carboxamide (Example 141) was treated in the similar manner to Example 196 to give the titled compound as an amorphous solid.

$^1$H-NMR (CDCl$_3$, δppm); 0.9-1.2 (2H, m), 1.55-2.0 (4H, m), 2.18 (3H, br d, J=6.6 Hz), 2.55-2.85 (3H, m), 2.94 (1H, br d, J=11.6 Hz), 3.04 (2H, t, J=8.7 Hz), 3.35 (1H, m), 3.47 (1H, br d, J=13.4 Hz), 3.5-3.8 (4H, m), 3.88 (1H, br d, J=11.0 Hz), 4.13 (2H, s), 4.43 (2H, s), 4.54 (1H, br d, J=13.2 Hz), 4.76 (2H, t, J=8.7 Hz), 7.61 (1H, t like), 7.80 (1H, s). LC-MS, m/z; 467 (MH$^+$).

Example 204

Preparation of N-[{4-[(1-(N-allyl-N-methylcarbamoyl)-4-piperidinyl)methyl]-2-morpholinyl}-methyl]-4-amino-5-chloro-2-ethoxybenzamide 1.5 fumarate

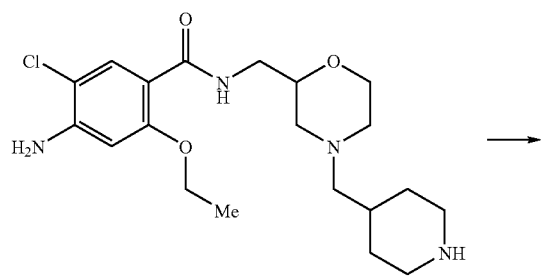

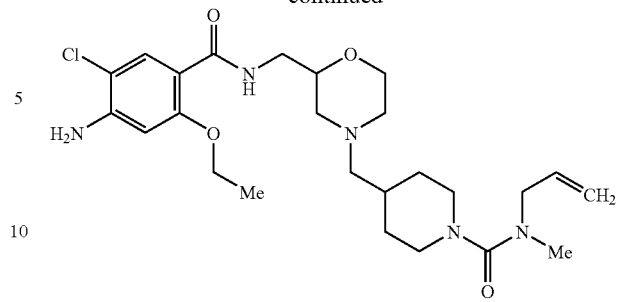

To a solution of trichloromethyl chloroformate (0.29 g) in methylene chloride (3 ml) was added dropwise a solution of N-methylallylamine (0.21 g) in methylene chloride (2 ml) under ice-cooling. The mixture was stirred for 10 minutes under ice-cooling, and then thereto was added dropwise a solution of 4-amino-5-chloro-2-ethoxy-N-[[4-(4-piperidinylmethyl)-2-morpholinyl]methyl]benzamide (Example 22) (1.0 g) and TEA (0.44 ml) in methylene chloride (5 ml). After completion of addition, the mixture was stirred at the same temperature for 3 hours. The reaction solution was washed with water, then brine, and then dried over anhydrous magnesium sulfate. The solvent was removed in vacuo. The residue was purified by silica gel column chromatography (eluent: chloroform/methanol=99/1 to 95/1) to give a base of the titled compound (0.47 g) as a white amorphous solid. The solid was treated with fumaric acid to give the titled compound as a powder. Melting point 170° C. (recrystallized from E)

$^1$H-NMR (DMSO-d$_6$, δppm); 0.95-1.0 (2H, m), 1.41 (3H, t, J=7.0 Hz), 1.67 (3H, d like, J=9.9 Hz), 1.82 (1H, t, J=10.4 Hz), 2.03 (1H, t like, J=9.7 Hz), 2.15 (2H, d like, J=6.1 Hz), 2.55-2.75 (2H, m), 2.66 (3H, s), 2.76 (1H, br d, J=11.0 Hz), 3.2 (1H, m), 3.35-3.65 (6H, m), 3.66 (2H, d like, J=5.5 Hz), 3.81 (1H, br d, J=11.0 Hz), 4.07 (2H, q, J=7.0 Hz), 5.14 (1H, s like), 5.18 (1H, d like, J=5.3 Hz), 5.82 (1H, m), 5.94 (2H, s), 6.47 (1¼, s), 6.63 (3H, s), 7.71 (1H, s), 8.09 (1H, t, J=5.2 Hz). LC-MS, m/z; 508 (MH$^+$).

Example 205

Preparation of (S)-4-amino-5-chloro-2-ethoxy-N-[{4-[(1-(N-methoxy-N-methylcarbamoyl)-4-piperidinyl)methyl]-2-morpholinyl}methyl]benzamide

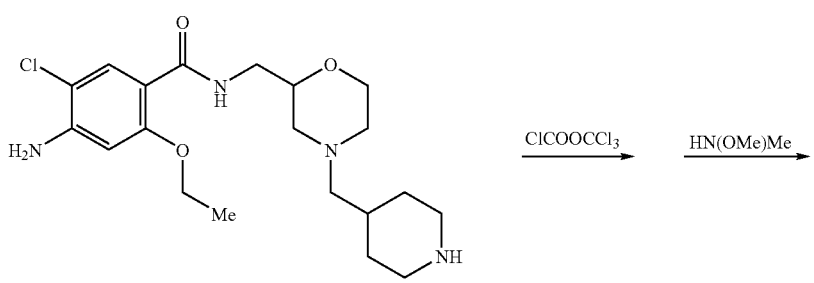

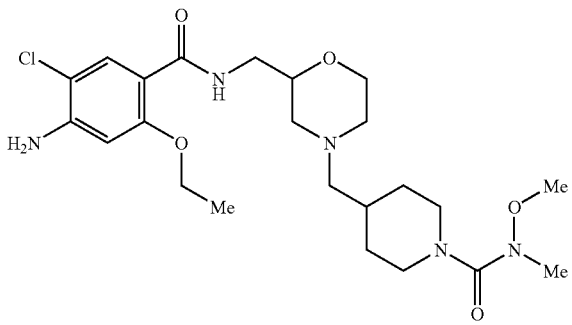

To a suspension of trichloromethyl chloroformate (0.15 ml) and O,N-dimethylhydroxyamine hydrochloride (0.24 g) in methylene chloride (10 ml) was added TEA (1.02 ml) at room temperature, and the mixture was stirred for 1 hour. The suspension was added dropwise to a solution of (S)-4-amino-5-chloro-2-ethoxy-N-[[4-(4-piperidinylmethyl)-2-morpholinyl]methyl]benzamide (Example 26) (1.0 g) in methylene chloride (10 ml) under ice cooling. After completion of addition, the internal temperature of the reaction solution was warmed to room temperature, and the solution was stirred for 2 hours. The reaction solution was washed with water, then brine, and then dried over anhydrous magnesium sulfate. The solvent was removed in vacuo. The residue was purified by silica gel column chromatography (eluent: chloroform/methanol=10/1) to give the titled compound (0.8 g) as a white solid. Melting point 127-129° C. (recrystallized from EA/H)

$^1$H-NMR (CDCl$_3$, δppm); 1.01-1.22 (2H, m), 1.51 (3H, t, J=7.0 Hz), 1.62-1.85 (3H, m), 1.92 (1H, br t, J=10.4 Hz), 2.05-2.25 (3H, m), 2.62 (1H, br d, J=11.3 Hz), 2.78 (3H, br q, J=11.7 Hz), 2.84 (3H, s), 3.37 (1H, m), 3.58 (3H, s), 3.61-3.76 (3H, m), 3.87 (1H, br d, J=10.1 Hz), 4.09 (2H, q, J=7.0 Hz), 4.0-4.3 (2H, m), 4.33 (2H, s), 6.27 (1H, s), 8.11 (1H, s), 8.22 (1H, br t). LC-MS, m/z; 498 (MH$^+$).

Example 206

Preparation of (S)-4-amino-5-chloro-2-ethoxy-N-[{4-[(1-imidazolecarbonyl-4-piperidinyl)-methyl]-2-morpholinyl}methyl]benzamide

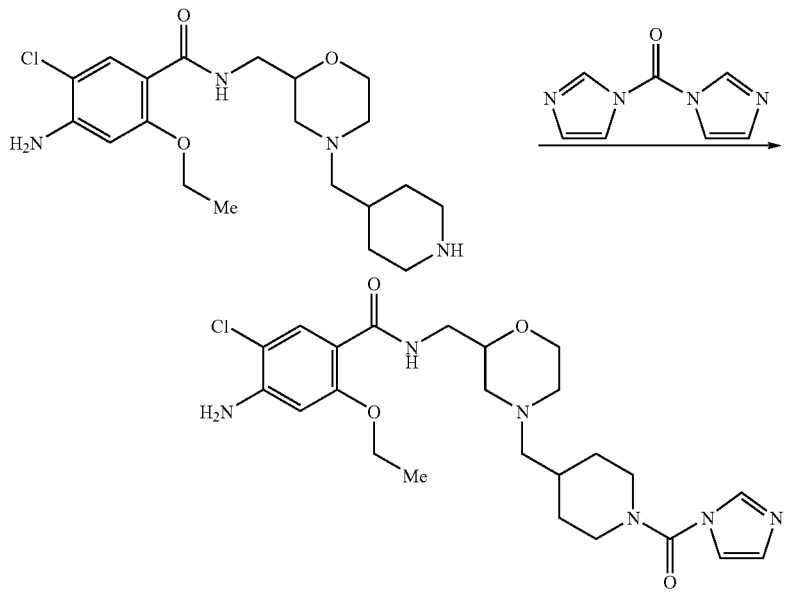

A solution of (S)-4-amino-5-chloro-2-ethoxy-N-[{4-(4-piperidinylmethyl)-2-morpholinyl}-methyl]benzamide (Example 26) (1.0 g) and N,N'-carbonyldiimidazole (0.43 g) in DMF (15 ml) was stirred at room temperature for 1 hour. The solvent was removed in vacuo. The residue was dissolved in chloroform, and then washed with water, then brine, and dried over anhydrous magnesium sulfate. The solvent was removed in vacuo, and the residue was purified by silica gel column chromatography (eluent: chloroform/methanol=10/1) to give the titled compound (1.07 g) as an amorphous solid.

$^1$H-NMR (CDCl$_3$, δppm); 1.1-1.3 (2H, m), 1.50 (3H, t, J=7.0 Hz), 1.7-2.0 (3H, m), 2.1-2.3 (4H, m), 2.62 (1H, br d, J=10.6 Hz), 2.74 (1H, br d, J=11.2 Hz), 3.02 (2H, t like, J=11.9 Hz), 3.4 (1H, m), 3.6-3.8 (3H, m), 3.87 (1H, br d, J=9.7 Hz), 4.09 (2H, q, J=7.0 Hz), 4.0-4.25 (2H, m), 4.36 (2H, s), 6.27 (1H, s), 7.09 (1H, s), 7.19 (1H, s), 7.85 (1H, s), 8.11 (1H, s), 8.22 (1H, t like). LC-MS, m/z; 505 (MH+).

Example 207

Preparation of (S)-4-amino-5-chloro-N-[{4-[(1-imidazolecarbonyl-4-piperidinyl)methyl]-2-morpholinyl}methyl]-2-methoxybenzamide

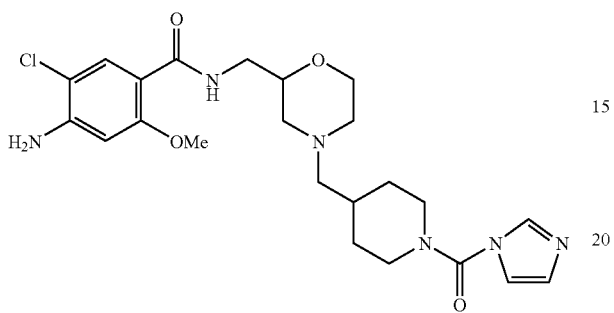

(S)-4-Amino-5-chloro-2-methoxy-N-[{4-(4-piperidinylmethyl)-2-morpholinyl}methyl]-benzamide (Example 24) was treated in the similar manner to Example 206 to give the titled compound as an amorphous solid. LC-MS, m/z; 491 (MH+).

Example 208

Preparation of (S)-4-amino-N-[{4-[(1-(1-azetidinecarbonyl)-4-piperidinyl)methyl]-2-morpholinyl}methyl]-5-chloro-2-ethoxybenzamide A solution of (S)-4-amino-5-chloro-2-ethoxy-N-[{4-[(1-imidazolecarbonyl-4-piperidinyl)-methyl]-2-morpholinyl}methyl]benzamide (Example 206) (1.07 g) and azetidine (0.25 g) in THF (15 ml) was heated to reflux for 19 hours with stirring. After cooling to room temperature, the reaction solution was dried under reduced pressure to be solidified, and the residue was purified by silica gel column chromatography (eluent: chloroform/methanol=10/1) to give the titled compound (0.43 g) as a white solid. Melting point 166-168° C. (recrystallized from EA/H)

$^1$H-NMR (CDCl$_3$, δppm); 0.98-1.17 (2H, m), 1.50 (3H, t, J=7.0 Hz), 1.57-1.8 (3H, m), 1.91 (1H, br t, J=10.4 Hz), 2.2-2.3 (3H, m), 2.21 (2H, t, J=7.7 Hz), 2.57-2.7 (2H, m), 2.73 (2H, br d, J=12.6 Hz), 3.35 (1H, m), 3.58-3.78 (3H, m), 3.78-3.92 (3H, m), 3.98 (4H, t, J=7.7 Hz), 4.09 (2H, q, J=7.0 Hz), 4.34 (2H, s), 6.27 (1H, s), 8.11 (1H, s), 8.22 (1H, t like). LC-MS, m/z; 494 (MH+).

Example 209

Preparation of 4-amino-5-chloro-2-ethoxy-N-[{4-[(1-ethyl-4-piperidinyl)methyl]-2-morpholinyl}methyl]benzamide

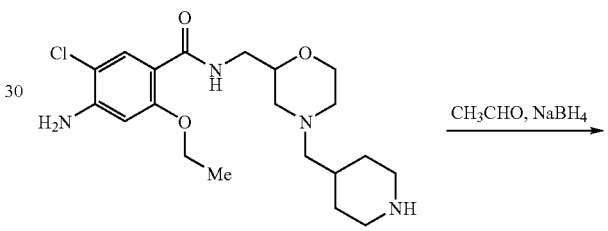

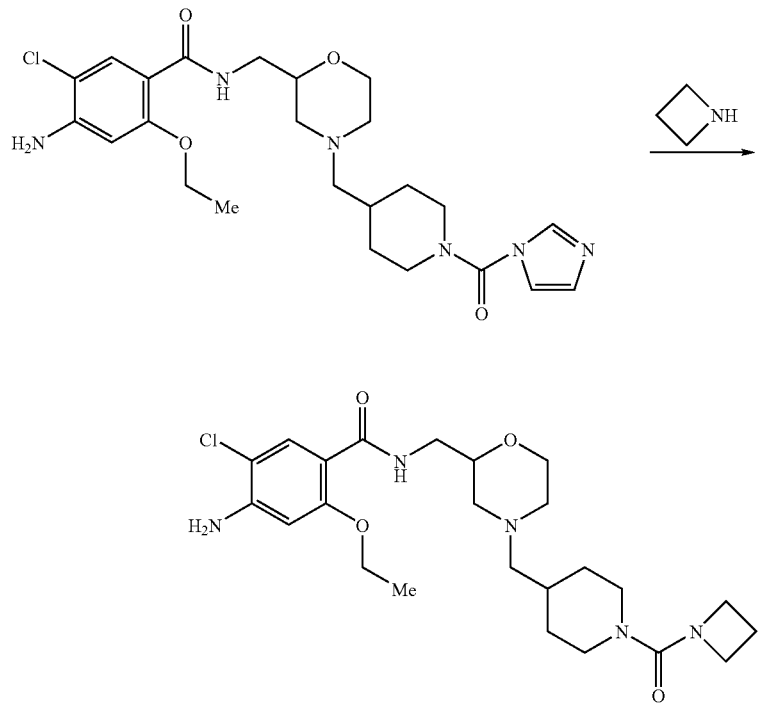

-continued

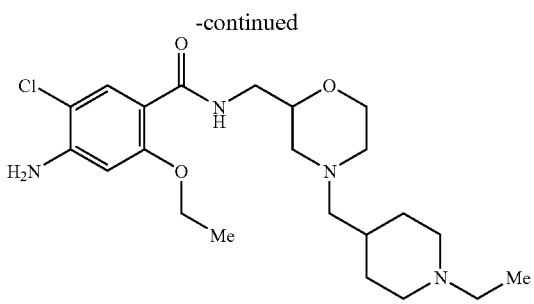

To a solution of 4-amino-5-chloro-2-ethoxy-N-[{4-(4-piperidinylmethyl)-2-morpholinyl}-methyl]benzamide (Example 22) (1.0 g) and TEA (0.49 g) in methanol (10 ml) was added acetaldehyde (0.21 g) under ice-cooling. The mixture was stirred at the same temperature for 2 hours, and then thereto was gradually added sodium borohydride (92 mg). After completion of addition, the mixture was stirred at the same temperature for 1 hour, and warmed to room temperature to stir overnight. The reaction solution was dried under reduced pressure to be solidified, and the residue was dissolved in chloroform, washed with water, then brine, and dried over anhydrous magnesium sulfate. Then, the solvent was removed in vacuo. The residue was purified by silica gel column chromatography (eluent: chloroform/methanol=10/1) to give the titled compound (1.2 g) as a white amorphous solid.

$^1$H-NMR (CDCl$_3$, δppm); 1.09 (3H, t, J=7.2 Hz), 1.27 (2H, br q, J=11.5 Hz), 1.50 (3H, t, J=7.0 Hz), 1.5 (1H, m), 1.6-2.3 (9H, m), 2.43 (2H, q, J=7.2 Hz), 2.62 (1H, br d, J=10.8 Hz), 2.74 (1H, br d, J=10.8 Hz), 2.98 (2H, br d, J=11.0 Hz), 3.3 (1H, m), 3.6-3.75 (3H, m), 3.86 (1H, br d, J=11.3 Hz), 4.08 (2H, q, J=7.0 Hz), 4.33 (1H, br d, J=6.8 Hz), 6.27 (1H, s), 8.11 (1H, s), 8.23 (1H, br t). LC-MS, m/z; 439 (MH$^+$), 314.

Example 210

Preparation of 4-amino-5-chloro-2-ethoxy-N-[{4-[(1-(3-fluorobenzyl)-4-piperidinyl)methyl]-2-morpholinyl}methyl]benzamide To a solution of 4-amino-5-chloro-2-ethoxy-N-[{4-(4-piperidinylmethyl)-2-morpholinyl}methyl]benzamide (Example 22) (0.75 g) and 4-fluorobenzaldehyde (0.27 g) in methanol (20 ml) was gradually added sodium triacetoxyhydroborate (0.77 g) at room temperature. After completion of addition, the mixture was stirred overnight. The mixture was washed with water, then brine, dried over anhydrous magnesium sulfate, and then the solvent was removed in vacuo. The residue was purified by silica gel column chromatography (eluent: chloroform/methanol=30/1 to 10/1) to give the titled compound (0.3 g) as a white solid. Melting point 172-174° C. (recrystallized from E/DE)

$^1$H-NMR (CDCl$_3$, δppm); 1.12-1.33 (2H, m), 1.50 (3H, t, J=7.0 Hz), 1.55-1.85 (4H, m), 1.85-2.04 (3H, m), 2.05-2.2 (3H, m), 2.62 (1H, br d, J=11.7 Hz), 2.74 (1H, br d, J=11.3 Hz), 2.85 (2H, br d, J=11.5 Hz), 3.35 (1H, m), 3.48 (2H, s), 3.6-3.75 (3H, m), 3.85 (1H, m), 4.08 (2H, q, J=7.0 Hz), 4.32 (1H, br d, J=6.8 Hz), 6.26 (1H, s), 6.92 (1H, m), 7.02-7.12 (2H, m), 7.26 (1H, m), 8.11 (1H, s), 8.23 (1H, t like). LC-MS, m/z; 519 (MH$^+$).

Example 211

Preparation of 4-amino-5-chloro-N-[{4-[(1-cyano-4-piperidinyl)methyl]-2-morpholinyl}-methyl]-2-ethoxybenzamide

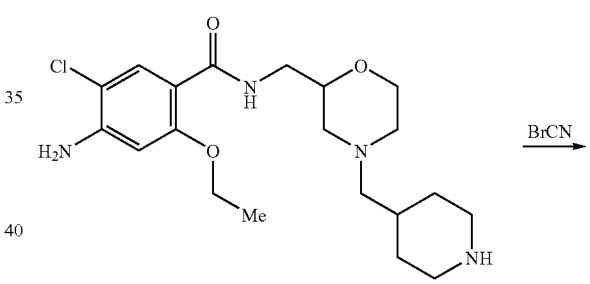

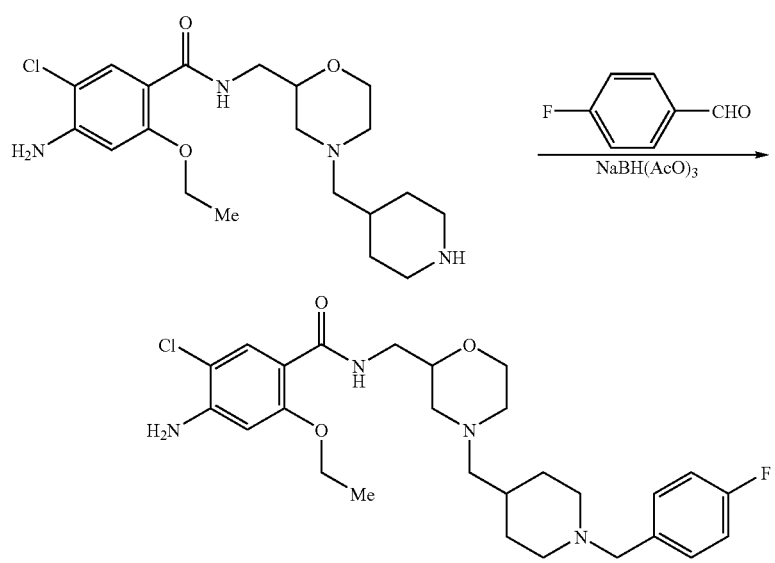

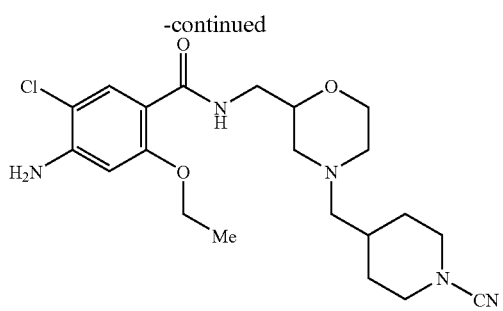

To a solution of 4-amino-5-chloro-2-ethoxy-N-[{4-(4-piperidinylmethyl)-2-morpholinyl}-methyl]benzamide (Example 22) (1.0 g) and TEA (0.41 ml) in methylene chloride (10 ml) was added cyanogen bromide (0.27 g) at room temperature, and then the mixture was stirred for 4 hours, washed with water, then brine and dried over anhydrous magnesium sulfate. Then, the solvent was removed in vacuo. The residue was purified by silica gel column chromatography (eluent: chloroform/methanol=10/1) to give the titled compound (0.7 g) as a white solid. Melting point 197° C. (degradation, recrystallized from E)

$^1$H-NMR (CDCl$_3$, δppm); 1.15-1.4 (2H, m), 1.50 (3H, t, J=7.0 Hz), 1.6 (1H, m), 1.78 (2H, t, J=16.1 Hz), 1.91 (1H, t, J=10.5 Hz), 2.0-2.2 (3H, m), 2.59 (1H, d, J=11.2 Hz), 2.71 (1H, d, J=11.0 Hz), 2.99 (2H, td, J=2.8, 12.5 Hz), 3.25-3.5 (3H, m), 3.58-3.76 (3H, m), 3.86 (1H, d like, J=6.4 Hz), 4.08 (2H, q, J=7.0 Hz), 4.37 (2H, s), 6.27 (1H, s), 8.10 (1H, s), 8.22 (1H, t like). LC-MS, m/z; 436 (MH$^+$).

Examples 212-219

The corresponding starting compounds in place of 4-amino-5-chloro-2-methoxy-N-[{4-(4-piperidinylmethyl)-2-morpholinyl}methyl]benzamide of Example 142 and the corresponding carboxylic acids in place of ethoxyacetic acid were treated in the similar manner to Example 142 to give the following compounds of Tables 26 and 27 as an amorphous solid or a powder.

TABLE 26

| Example | * | R$^1$ | —B | LC-MS: m/z(MH$^+$) |
|---|---|---|---|---|
| 212 | S | Me | 2-methylpyridinyl | 502 |
| 213 | S | Me | (S)-5-methyl-dihydrofuran-2(3H)-one | 509 |
| 214 | S | Me | (R)-5-methyl-dihydrofuran-2(3H)-one | 509 |
| 215 | S | Me | (S)-5-methylpyrrolidin-2-one | 508 |
| 216 | S | Me | (S)-2-methylpiperidine | 508 |

TABLE 27

| Example | * | —R | LC-MS: m/z(MH$^+$) |
|---|---|---|---|
| 217 | S | menthyl acetate group | 579 |
| 218 | S | —CO$_2$CH$_2$CCl$_3$ | 571 |
| 219 | S | naphthalen-2-yl acetate | 567 |

Example 220

Preparation of (S)-4-amino-5-chloro-N-[{4-[(1-hydroxyacetyl-4-piperidinyl)methyl]-2-morpholinyl}methyl]-2-methoxybenzamide hydrobromide 2 hydrate

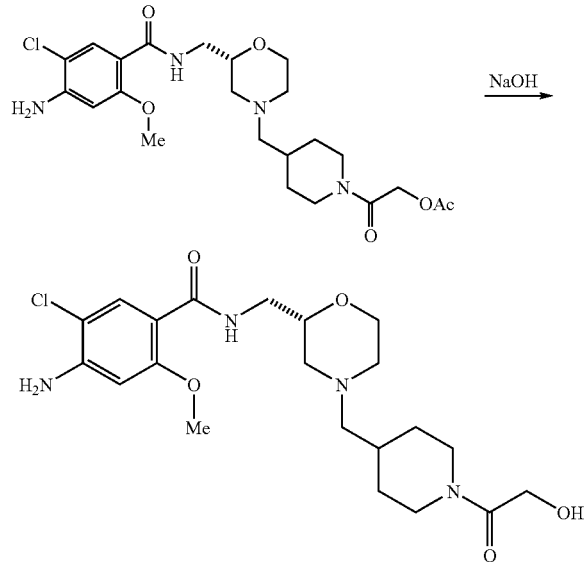

In place of N-[{4-[(1-acetoxyacetyl-4-piperidinyl)methyl]-2-morpholinyl}methyl]-4-amino-5-chloro-2-methoxybenzamide of Example 198 (Alternative Method), (S)-N-[{4-[(1-acetoxyacetyl-4-piperidinyl)methyl]-2-morpholinyl}methyl]-4-amino-5-chloro-2-methoxybenzamide was treated in the similar manner to give a free form of the titled compound as a white amorphous solid. The solid was dissolved in aqueous acetone, and thereto was added dropwise 1 equivalent of HBr water. Then, thereto were added seed crystals, and the mixture was stirred at room temperature to give the titled compound (HBr salt) as a white solid. The seed crystals used in this procedure were obtained by letting salts which could be obtained by treating a free form of the titled compound with hydrobromic acid stand under 93% humidity condition. Melting point; 215-216° C. (degradation)

$^1$H-NMR (DMSO-d$_6$, δppm); 0.95-1.22 (2H, m), 1.67-1.80 (2H, m), 2.07 (1H, m), 2.63 (1H, br t, J=12.7 Hz), 2.81 (1H, m), 2.90-3.12 (4H, m), 3.25-3.55 (6H, m), 3.64-3.82 (2H, m), 3.84 (3H, s), 3.93 (1H, m), 4.00-4.13 (3H, m), 4.33 (1H, d, J=11.7 Hz), 6.02 (2H, br s), 6.49 (1H, s), 7.70 (1H, s), 8.10 (11H, t like, J=6.0 Hz), 9.37 (1H, br s). LC-MS, m/z; 455 (MH$^+$). XRD; 2θ=9.5, 17.7, 20.4, 24.4, 25.5°.

Examples 221-230

(S)-4-amino-5-chloro-2-methoxy-N-[{4-(4-piperidinylmethyl)-2-morpholinyl}methyl]-benzamide and the corresponding carboxylic acid compounds were treated in the similar manner to Example 142 to give the following compounds of Table 28 as an amorphous solid or a powder.

TABLE 28

| Example | —B | LC-MS: m/z (MH$^+$) | $^1$H—NMR |
|---|---|---|---|
| 221 | Me | 439 | (CDCl$_3$, δ ppm); 0.98-1.16 (2H, m), 1.66-1.94 (4H, m), 2.05-2.20 (3H, m), 2.08 (3H, m), 2.48-2.68 (2H, m), 2.75 (1H, m), 3.02 (1H, dt, J = 12.8, 2.6 Hz), 3.34 (1H, m), 3.62-3.90 (5H, m), 3.88 (3H, s), 4.48 (2H, br s), 4.59 (1H, br d, J = 13.4 Hz), 6.30 (1H, s), 8.01 (1H, br t), 8.08 (1H, s). |
| 222 | CH$_2$NHCOPh | 558 | (CDCl$_3$, δ ppm); 1.03-1.18 (2H, m), 1.70-1.95 (4H, m), 2.09-2.24 (3H, m), 2.48-2.80 (3H, m), 3.04 (1H, br t), 3.35 (1H, m), 3.64-3.74 (3H, m), 3.78 (1H, br d, J = 13.7 Hz), 3.88 (1H, m), 3.89 (3H, s), 4.18-4.31 (2H, m), 4.42 (2H, s), 4.59 (1H, br d, J = 12.9 Hz), 6.30 (1H, s), 7.38-7.53 (4H, m), 7.84 (2H, d, J = 6.8 Hz), 8.01 (1H, br t), 8.09 (1H, s). |
| 223 | CH$_2$CN | 464 | (CDCl$_3$, δ ppm); 1.03-1.26 (2H, m), 1.68-1.98 (4H, m), 2.10-2.27 (3H, m), 2.56-2.68 (2H, m), 2.76 (1H, br t), 3.14 (1H, br t), 3.35 (1H, m), 3.48 (2H, d, J = 2.9 Hz), 3.64-3.76 (4H, m), 3.90 (1H, m), 3.89 (3H, s), 4.40 (2H, s), 4.55 (1H, br d, J = 13.2 Hz), 6.30 (1H, s), 8.01 (1H, br s), 8.09 (1H, s). |
| 224 | CH$_2$CH$_2$OMe | 483 | (CDCl$_3$, δ ppm); 0.97-1.12 (2H, m), 1.68-1.95 (4H, m), 2.07-2.22 (3H, m), 2.50-2.66 (4H, m), 2.75 (1H, br t, J = 9.5 Hz), 2.98 (1H, br t), 3.35 (1H, m), 3.36 (3H, m), 3.63-3.75 (5H, m), 3.83-3.94 (2H, m), 3.89 (3H, s), 4.43 (2H, br s), 4.61 (1H, br d, J = 13.4 Hz), 6.30 (1H, s), 8.00 (1H, br s), 8.09 (1H, s). |

TABLE 28-continued

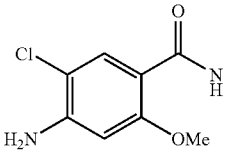

| Example | —B | LC-MS: m/z (MH+) | 1H—NMR |
|---|---|---|---|
| 225 | 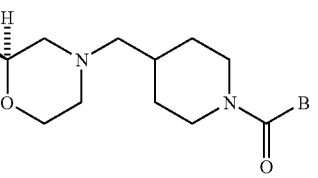 Me, OMe | 483 | (CDCl3, δ ppm); 1.00-1.15 (2H, m), 1.35-1.43 (3H, m), 1.65-1.96 (4H, m), 2.07-2.24 (3H, m), 2.53-2.67 (2H, m), 2.76 (1H, br t, J = 9.3 Hz), 2.97 (1H, br t), 3.35 (1H, m), 3.36 (3H, s), 3.63-3.73 (3H, m), 3.90 (1H, m), 3.89 (3H, s), 4.12-4.23 (2H, m), 4.40 (2H, br s), 4.60 (1H, br d, J = 11.4 Hz), 6.30 (1H, s), 8.01 (1H, br s), 8.10 (1H, s). |
| 226 | 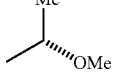 | 495 | (CDCl3, δ ppm); 0.96-1.15 (2H, m), 1.65-1.95 (4H, m), 2.02-2.29 (5H, m), 2.53-2.67 (2H, m), 2.76 (1H, br t, J = 11.2 Hz), 3.04 (1H, m), 3.19-3.42 (2H, m), 3.64-3.75 (3H, m), 3.83-3.96 (5H, m), 3.89 (3H, s), 4.01 (1H, br t, J = 4.3 Hz), 4.40 (2H, br s), 4.61 (1H, br d, J = 12.4 Hz), 6.30 (1H, s), 8.01 (1H, br s), 8.10 (1H, s). |
| 227 | COMe | 467 | (CDCl3, δ ppm); 1.05-1.22 (2H, m), 1.68-1.92 (4H, m), 2.09-2.20 (3H, m), 2.41 (3H, s), 2.57-2.78 (3H, m), 3.02 (1H, m), 3.34 (1H, m), 3.63-3.78 (4H, m), 3.90 (1H, m), 3.91 (3H, s), 4.39 (2H, br s), 4.48 (1H, br d, J = 13.4 Hz), 6.30 (1H, s), 8.00 (1H, br t), 8.10 (1H, s). |
| 228 | 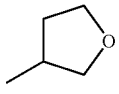 | 492 | (CDCl3, δ ppm); 1.13-1.28 (2H, m), 1.75-1.98 (4H, m), 2.09-2.26 (3H, m), 2.58-2.84 (3H, m), 3.09 (1H, br t), 3.35 (1H, m), 3.64-3.80 (3H, m), 3.87 (1H, m), 3.89 (3H, s), 4.39 (2H, br s), 4.72 (2H, br dd, J = 43.3, 11.0 Hz), 6.30 (1H, s), 7.86 (1H, s), 8.00 (1H, br t), 8.10 (1H, s), 8.16 (1H, s). |
| 229 | 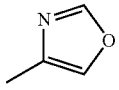 | 492 | (DMSO-d6, δ ppm); 0.97-1.13 (2H, m), 1.64-2.24 (7H, m), 2.56-2.85 (3H, m), 3.08 (1H, br t), 3.20-3.64 (5H, m), 3.81 (1H, m), 3.83 (3H, s), 4.46 (1H, br d, J = 12.7 Hz), 5.98 (2H, s), 6.48 (1H, s), 7.69 (1H, s), 7.99 (1H, br t), 8.43 (1H, br s), 14.5 (1H, br s). |
| 230 | 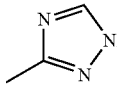 CN | 526 | (CDCl3, δ ppm); 0.97-1.30 (2H, m), 1.69-1.97 (4H, m), 2.09-2.24 (3H, m), 2.61 (1H, br d, J = 9.8 Hz), 2.73-2.86 (2H, m), 3.01 (1H, br t, J = 13.2 Hz), 3.34 (1H, m), 3.54-3.73 (4H, m), 3.87 (1H, m), 3.89 (3H, s), 4.41 (2H, s), 4.69 (1H, br d, J = 12.0 Hz), 6.30 (1H, s), 7.46-7.51 (2H, m), 7.68-7.73 (2H, m), 8.01 (1H, br t), 8.09 (1H, s). |

Examples 231-232

(S)-4-amino-5-chloro-N-[{4-(4-piperidinylmethyl)-2,3-dihydrobenzo[b]furan-7-carboxamide and the corresponding carboxylic acid compounds were treated in the similar manner to Example 142 to give the following compounds of Table 29 as an amorphous solid or a powder.

TABLE 29

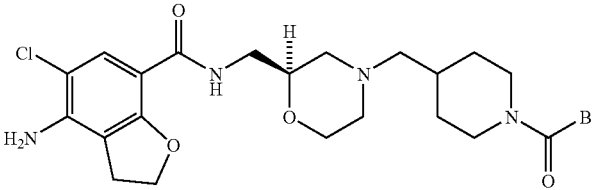

| Example | —B | LC-MS: m/z (MH+) | $^1$H—NMR |
|---|---|---|---|
| 231 | Me | 451 | (CDCl$_3$, δ ppm); 0.99-1.08 (2H, m), 1.59-1.96 (4H, m), 2.08-2.12 (3H, m), 2.08 (3H, s), 2.48-2.64 (2H, m), 2.75 (1H, br t, J = 10 Hz), 3.04 (1H, m), 3.06 (2H, t, J = 8.6 Hz), 3.34 (1H, m), 3.62-3.74 (3H, m), 3.75-3.92 (2H, m), 4.28 (2H, s), 4.59 (1H, br d, J = 13.4 Hz), 4.78 (2H, t, J = 9.0 Hz), 7.62 (1H, br s), 7.86 (1H, s). |
| 232 | 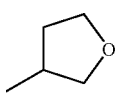 | 507 | (CDCl$_3$, δ ppm); 0.94-1.12 (2H, m), 1.68-1.94 (4H, m), 2.02-2.29 (5H, m), 2.53-2.65 (2H, m), 2.76 (1H, br t, J = 11.0 Hz), 3.03 (1H, m), 3.06 (2H, t, J = 8.5 Hz), 3.19-3.40 (2H, m), 3.62-3.73 (3H, m), 3.82-3.95 (5l-1, m), 4.01 (1H, br t), 4.27 (2H, s), 4.61 (1H, br d, J = 12.2 Hz), 4.78 (2H, t, J = 9.0 Hz), 7.62 (1H, br s), 7.86 (1H, s). |

Example 233

Preparation of (S)-4-amino-5-chloro-N-[{4-[(1-hydroxyacetyl-4-piperidinyl)methyl]-2-morpholinyl}methyl]-2,3-dihydrobenzo[b]furan-7-carboxamide

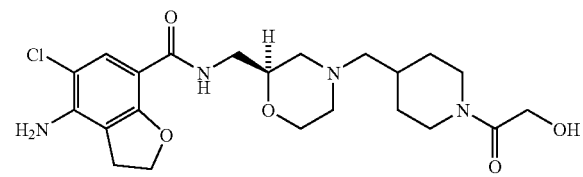

In place of N-[{4-[(1-acetoxyacetyl-4-piperidinyl)methyl]-2-morpholinyl}methyl]-4-amino-5-chloro-2,3-dihydrobenzo[b]furan-7-carboxamide of Example 203, the corresponding optically-active starting compounds were treated in the similar manner to Example 203 to give the titled compound as an amorphous solid.

$^1$H-NMR (CDCl$_3$, δppm); 1.00-1.15 (2H, m), 1.70-1.92 (4H, m), 2.08-2.21 (3H, m), 2.55-2.83 (3H, m), 2.94 (1H, m), 3.06 (2H, t, J=8.8 Hz), 3.34 (1H, m), 3.47 (1H, br d, J=13.4 Hz), 3.62-3.76 (4H, m), 3.87 (1H, br d, J=11.7 Hz), 4.13-4.20 (2H, m), 4.27 (2H, s), 4.57 (1H, br d, J=13.2 Hz), 4.78 (2H, t, J=9.0 Hz), 7.62 (1H, br s), 7.86 (1H, s).

Formulation 1: Preparation of Tablets

4-Amino-5-chloro-N-[{4-[(1-dimethylcarbamoyl-4-piperidinyl)methyl]-2-morpholinyl}-methyl]-2-ethoxybenzamide (5 g), lactose (80 g), cornstarch (30 g), crystalline cellulose (25 g), hydroxypropylcellulose (3 g), light anhydrous silicic acid (0.7 g) and magnesium stearate (1.3 g) were mixed in the conventional manner, granulated and tableted to give 1000 tablets in 145 mg/tablet.

Formulation 2: Preparation of Powders

4-Amino-5-chloro-N-[{4-[(1-dimethylcarbamoyl-4-piperidinyl)methyl]-2-morpholinyl}-methyl]-2-ethoxybenzamide (10 g), lactose (960 g), hydroxypropylcellulose (25 g) and light anhydrous silicic acid (5 g) were mixed in the conventional manner to give powders.

INDUSTRIAL APPLICABILITY

The inventive compound shows strong affinity for 5-HT$_4$ receptor, may be used in the treatment or prevention of various diseases such as digestive system diseases, including an irritable bowel syndrome, an atonic constipation, a habitual constipation, a chronic constipation, a constipation induced by drug such as morphine or an antipsychotic agent, a constipation or dyschezia by contrast agents, functional dyspepsia, acute-chronic gastritis, reflux esophagitis, gastric ulcer, duodenal ulcer, gastric neurosis, postoperative paralytic ileus, senile ileus, postgastrectomy syndrome or pseudo-bowel obstruction, neuropsychiatric diseases, including schizophrenia, Alzheimer disease, depression, memory disorder or anxiety, urinary system diseases, including dysuria by urinary obstruction or enlarged prostate, and various functional aberration in gastrointestinal system associated with treatment for various diseases, including anorexia, nausea, emesis or abdomen enlarged feeling, and may be particularly useful as an enterokinesis-promoting agent or a digestive tract function-improving agent.

The invention claimed is:

1. A compound of formula (1):

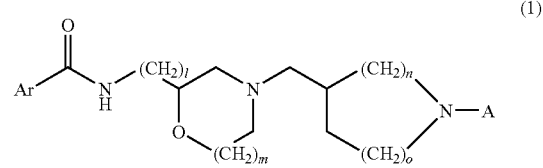

wherein Ar is a group of formula (Ar-1) or (Ar-2):

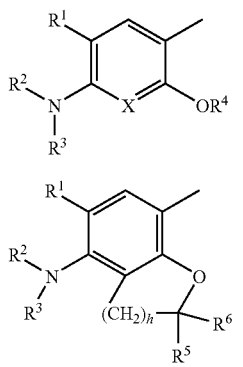

wherein $R^1$ is hydrogen or halogen, $R^2$ is hydrogen or alkyl, $R^3$ is hydrogen, alkyl or alkanoyl, $R^4$ is hydrogen, alkyl, alkenyl or alkynyl, X is nitrogen or CH, $R^5$ and $R^6$ are the same or different and each hydrogen or alkyl, and h is 1, 2 or 3;
l is 1, 2 or 3;
m is 1 or 2;
n is 0, 1 or 2;
o is an integer of 0 to 3, provided that n and o are not simultaneously 0;
A is a group selected from the group consisting of (1) to (6):
(1) hydrogen, cyano or formyl;
(2) optionally substituted alkyl, optionally substituted alkenyl or optionally substituted alkynyl;
(3) —$COR^7$, —$CSR^7$, —$COOR^7$, —$SO_2R^7$ or —CO—$COR^7$
wherein $R^7$ is optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted monocyclic or bicyclic nonaromatic unsaturated heterocyclyl in which the heterocyclyl is bonded via any carbon atoms on the heterocycle, or optionally substituted monocyclic or bicyclic saturated heterocyclyl in which the heterocyclyl is bonded via any carbon atoms on the heterocycle;
(4) —CO—$COOR^8$
wherein $R^8$ is alkyl;
(5) —$CONR^9$—$OR^{10}$
wherein $R^9$ and $R^{10}$ are the same or different and each hydrogen, alkyl, alkenyl or alkynyl; and
(6) —$CONR^{12}R^{13}$, —$CSNR^{12}R^{13}$ or —$SO_2NR^{12}R^{13}$
wherein $R^{12}$ is hydrogen or any one of groups in $R^7$, $R^{13}$ is hydrogen, alkyl, alkenyl or alkynyl; or both $R^{12}$ and $R^{13}$ may combine each other together with the adjacent nitrogen atom to form optionally substituted saturated or unsaturated monocyclic nitrogen-containing heterocycle containing 1 to 3 heteroatoms selected from 1 to 3 nitrogen, 1 oxygen or 1 sulfur;
provided that if alkyl, alkenyl or alkynyl in A or $R^7$ is substituted, then alkyl, alkenyl and alkynyl are optionally substituted by the same or different 1 to 5 substituents selected from the group consisting of (a) to (d):
(a) halogen, cyano, nitro, hydroxy, carboxy, amino, carbamoyl or trifluoromethyl;

(b) —$OR^{14}$, —$SR^{14}$, —$COR^{14}$, —$COOR^{14}$, —O—$COR^{14}$, —$NR^{15}$—$COR^{14}$, —$NR^{15}$—$COOR^{14}$, —$NR^{15}$—$SO_2R^{14}$, —$NR^{15}R^{16}$ or —$CONR^{15}R^{16}$
wherein $R^{14}$ is alkyl, alkenyl or alkynyl optionally substituted by the same or different 1 to 5 substituents selected from the group consisting of the following group:
(b') halogen, hydroxy, carboxy, amino, carbamoyl, —$OR^{17}$, —$COOR^{17}$, —$NR^{18}$—$COR^{17}$, —$NR^{18}$—$COOR^{17}$, —$NR^{18}$—$SO_2R^{17}$, —$NR^{18}R^{19}$ or —$CONR^{18}R^{19}$ in which $R^{17}$ is alkyl, alkenyl or alkynyl, $R^{18}$ is hydrogen or alkyl, $R^{19}$ is alkyl, alkenyl or alkynyl, or both $R^{18}$ and $R^{19}$ may combine each other together with the adjacent nitrogen atom to form optionally substituted saturated or unsaturated monocyclic nitrogen-containing heterocycle containing 1 to 3 heteroatoms selected from 1 to 3 nitrogen, 1 oxygen or 1 sulfur,
$R^{15}$ is hydrogen, or alkyl, alkenyl or alkynyl optionally substituted by the same or different 1 to 5 substituents selected from the above (b'),
$R^{16}$ is alkyl, alkenyl or alkynyl optionally substituted by the same or different 1 to 5 substituents selected from the above (b'), or both $R^{15}$ and $R^{16}$ may combine each other together with the adjacent nitrogen atom to form optionally substituted saturated or unsaturated monocyclic nitrogen-containing heterocycle containing 1 to 3 heteroatoms selected from 1 to 3 nitrogen, 1 oxygen or 1 sulfur;
(c) —$R^{20}$, —$OR^{20}$ or —$NR^{15}$—$COR^{20}$
wherein $R^{15}$ has the same meaning as defined above, $R^{20}$ is optionally substituted cycloalkyl, optionally substituted cycloalkenyl, optionally substituted monocyclic or bicyclic nonaromatic unsaturated heterocyclyl, optionally substituted monocyclic or bicyclic saturated heterocyclyl; and
(d) —$R^{21}$, —$OR^{21}$, —$COR^{21}$, —$SR^{21}$, —$SO_2R^{21}$ or —$NR^{15}$—$COR^{21}$
wherein $R^{15}$ has the same meaning as defined above, $R^{21}$ is optionally substituted aryl or optionally substituted heteroaryl;
provided that if cycloalkyl or cycloalkenyl is substituted, then cycloalkyl and cycloalkenyl are optionally substituted by the same or different 1 to 5 substituents selected from the following (e):
(e) halogen, hydroxy, alkyl, alkoxy or oxo;
provided that if any ring carbon atoms are substituted in the monocyclic or bicyclic nonaromatic unsaturated heterocyclyl, monocyclic or bicyclic saturated heterocyclyl, or saturated or unsaturated monocyclic nitrogen-containing heterocyclyl, then the carbon atoms are optionally substituted by the same or different 1 to 5 substituents selected from the above (e),
provided that if any ring nitrogen atoms are substituted, then the nitrogen atoms are optionally substituted by the following (f):
(f) alkyl, alkanoyl, alkoxycarbonyl or alkylsulfonyl;
provided that if aryl or heteroaryl are substituted, then the aryl and heteroaryl are optionally substituted by the same or different 1 to 5 substituents selected from the group consisting of the following (g) to (i):
(g) halogen, cyano, nitro, hydroxy, carboxy, haloalkyl, haloalkoxy, amino, carbamoyl, —$(CH_2)_2$—O— or —O—$CH_2$—O—;
(h) —$R^{14}$, —$OR^{14}$, —$SR^{14}$, —$COR^{14}$, —$COOR^{14}$, —O—$COR^{14}$, —$NR^{15}$—$COOR^{14}$, —$NR^{15}$—$COOR^{14}$, —$NR^{15}$—$SO_2R^{14}$, —$NR^{15}R^{16}$ or —$CONR^{15}R^{16}$ wherein $R^{14}$, $R^{15}$ and $R^{16}$ have the same meanings as defined above; and (i) phenyl or phenoxy which is optionally substituted by 1 to 5 substituents selected from the group consisting of halogen, hydroxy, alkyl and alkoxy; or a pharmaceutically acceptable salt thereof.

2. The compound as claimed in claim 1, wherein $R^1$ is chlorine, bromine or iodine, $R^4$ is alkyl, $R^5$ and $R^6$ are the same or different and each hydrogen or methyl, or a pharmaceutically acceptable salt thereof.

3. The compound as claimed in claim 2, wherein $R^4$ is methyl, ethyl, propyl or isopropyl, or a pharmaceutically acceptable salt thereof.

4. The compound as claimed in claim 1, wherein $R^2$ is hydrogen, $R^3$ is hydrogen or methyl, or a pharmaceutically acceptable salt thereof.

5. The compound as claimed in claim 4, wherein $R^2$ and $R^3$ are hydrogen, or a pharmaceutically acceptable salt thereof.

6. The compound as claimed in claim 1, wherein l is 1 or 2, m is 1 or 2, n is 1 or 2, o is 1 or 2, or a pharmaceutically acceptable salt thereof.

7. The compound as claimed in claim 1, wherein $R^1$ is chlorine or bromine, $R^2$ and $R^3$ are hydrogen, $R^4$ is methyl or ethyl, $R^5$ and $R^6$ are hydrogen, h is 1, l is 1, m is 1, n is 2, o is 1, or a pharmaceutically acceptable salt thereof.

8. The compound as claimed in claim 1, wherein A is (1-1) hydrogen, cyano or formyl; or (2-1) alkyl, or phenyl-substituted alkyl wherein phenyl is optionally substituted by the same or different 1 to 5 substituents selected from the group consisting of halogen, hydroxy, alkyl, alkoxy, alkanoyl, haloalkyl, haloalkoxy, amino and carboxy; or a pharmaceutically acceptable salt thereof.

9. The compound as claimed in claim 1, wherein A is (3-1) —$COR^{7a}$, —$COOR^{7a}$, —$SO_2R^{7a}$ or —CO—$COR^{7a}$ wherein $R^{7a}$ is optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted monocyclic or bicyclic nonaromatic unsaturated heterocyclyl, or optionally substituted monocyclic or bicyclic saturated heterocyclyl;

provided that if alkyl, alkenyl or alkynyl in $R^{7a}$ is substituted, then the alkyl, alkenyl and alkynyl are optionally substituted by 1 to 5 substituents selected from the group consisting of (a-1) to (d-1):

(a-1) halogen, cyano, hydroxy, carboxy, amino or carbamoyl;

(b-1) —$OR^{14a}$, —$COR^{14a}$, —$COOR^{14a}$, —O—$COR^{14a}$, —$NR^{15a}$—$COR^{14a}$, —$NR^{15a}$—$COOR^{14a}$, —$NR^{15a}R^{16a}$ or —$CONR^{15a}R^{16a}$ wherein $R^{14a}$ is alkyl, $R^{15a}$ is hydrogen or alkyl, $R^{16a}$ is alkyl, or both $R^{15a}$ and $R^{16a}$ may combine each other together with the adjacent nitrogen atom to form saturated monocyclic nitrogen-containing heterocycle containing 1 to 3 heteroatoms selected from 1 to 3 nitrogen, 1 oxygen or 1 sulfur, and the nitrogen atom on the monocyclic nitrogen-containing heterocycle is optionally substituted by alkyl, alkanoyl or alkoxycarbonyl;

(c-1) cycloalkyl which is optionally substituted by the same or different 1 to 5 substituents selected from halogen, hydroxy, alkyl or alkoxy, monocyclic or bicyclic saturated heterocyclyl wherein the ring carbon atom is optionally substituted by the same or different 1 to 5 substituents selected from halogen, hydroxy, alkyl or alkoxy and the ring nitrogen atom is optionally substituted by alkyl, alkanoyl or alkoxycarbonyl; and (d-1) —$R^{21a}$ or —$NR^{15a}$—$COR^{21a}$ wherein $R^{15a}$ has the same meaning as defined above, $R^{21a}$ is aryl or heteroaryl, and the aryl and heteroaryl are optionally substituted by the same or different 1 to 5 substituents selected from halogen, hydroxy, carboxy, haloalkyl, haloalkoxy, amino, carbamoyl, cyano, —$R^{14a}$, —$OR^{14a}$, —$COR^{14a}$, —$NR^{15}$—$COR^{14a}$, or —$NR^{15a}R^{16a}$ wherein $R^{14a}$, $R^{15a}$ and $R^{16a}$ have the same meanings as defined above;

provided that if cycloalkyl or cycloalkenyl in $R^{7a}$ is substituted, then cycloalkyl and cycloalkenyl are optionally substituted by the same or different 1 to 5 substituents selected from the following (e-1):

(e-1) halogen, hydroxy, alkyl or alkoxy;

provided that if any ring carbon atoms are substituted in optionally substituted monocyclic or bicyclic nonaromatic unsaturated heterocyclyl, and optionally substituted monocyclic or bicyclic saturated heterocyclyl in $R^{7a}$, then the carbon atoms are optionally substituted by the same or different 1 to 5 substituents selected from the above (e-1), and if any ring nitrogen atoms are substituted, then the nitrogen atoms are optionally substituted by the same or different 1 to 5 substituents selected from the following (f-1):

(f-1) alkyl, alkanoyl, alkoxycarbonyl or alkylsulfonyl;

provided that if aryl or heteroaryl in $R^{7a}$ is substituted, then the aryl and heteroaryl are optionally substituted by the same or different 1 to 5 substituents selected from the group consisting of the following groups:

(g-1) halogen, nitro, hydroxy, carboxy, amino, carbamoyl, haloalkyl, haloalkoxy or cyano;

(h-1) —$R^{14a}$, —$OR^{14a}$, —$COR^{14a}$, —$COOR^{14a}$, —O—$COR^{14a}$, —$NR^{15a}$—$COR^{14a}$, —$NR^{15a}$—$COOR^{14a}$ or —$NR^{15a}R^{16a}$ wherein $R^{14a}$, $R^{15a}$ and $R^{16a}$ have the same meanings as defined above; and (i-1) phenyl or phenoxy which is optionally substituted by 1 to 5 substituents selected from the group consisting of halogen, hydroxy, alkyl and alkoxy; or a pharmaceutically acceptable salt thereof.

10. The compound as claimed in claim 9, wherein A is (3-2) —$SO_2R^{7b}$ wherein $R^{7b}$ is alkyl, alkyl substituted by optionally substituted phenyl, or optionally substituted phenyl, provided that if phenyl is substituted, then the phenyl is optionally substituted by the same or different 1 to 5 substituents selected from the group consisting of halogen, hydroxy, carboxy, haloalkyl, haloalkoxy, amino, carbamoyl, —$R^{14b}$, —$OR^{14b}$, —$COR^{14b}$, —$COOR^{14b}$ and —O—$COR^{14b}$ wherein $R^{14b}$ is alkyl; or a pharmaceutically acceptable salt thereof.

11. The compound as claimed in claim 10, wherein $R^{7b}$ is $C_{1-3}$ alkyl, or a pharmaceutically acceptable salt thereof.

12. The compound as claimed in claim 9, wherein A is (3-3) —$COR^{7c}$ or —CO—$COR^{7c}$ wherein $R^{7c}$ is optionally substituted alkyl or optionally substituted alkenyl;

provided that if alkyl or alkenyl in $R^{7c}$ is substituted, then the alkyl and alkenyl are optionally substituted by 1 to 5 substituents selected from the group consisting of (a-2) to (d-2):

(a-2) hydroxy, halogen, carbamoyl or cyano;

(b-2) —OR$^{14c}$, —COR$^{14c}$, —COOR$^{14c}$, —O—COR$^{14c}$, —NR$^{15c}$—COR$^{14c}$, —NR$^{15c}$R$^{16c}$ or —CONR$^{15c}$R$^{16c}$ wherein R$^{14c}$ and R$^{16c}$ are same or different alkyl and R$^{15c}$ is hydrogen or alkyl;

(c-2) cycloalkyl, or monocyclic or bicyclic saturated heterocyclyl wherein the nitrogen atom on the monocyclic or bicyclic saturated heterocyclyl is optionally substituted by alkyl, alkanoyl or alkoxycarbonyl; and (d-2) —R$^{21c}$ or —NR$^{15c}$—COR$^{21c}$ wherein R$^{15c}$has the same meaning as defined above, R$^{21c}$ is aryl or heteroaryl, and the aryl and heteroaryl are optionally substituted by the same or different 1 to 5 substituents selected from the group consisting of halogen, hydroxy, carboxy, haloalkyl, haloalkoxy, amino, carbamoyl, cyano, —R$^{14c}$, —OR$^{14c}$ and —COR$^{14c}$ wherein R$^{14c}$ has the same meaning as defined above; or a pharmaceutically acceptable salt thereof.

13. The compound as claimed in claim 12, wherein R$^{7c}$ is C$_{1-3}$ alkyl optionally substituted by a group selected from the group consisting of the following (a-3) and (b-3):

(a-3) hydroxy, carbamoyl or cyano; and (b-3) —OR$^{14d}$, COOR$^{14d}$, —O—COR$^{14d}$, —NR$^{15d}$—COR$^{14d}$, —NR$^{15d}$R$^{16d}$ or —CONR$^{15d}$R$^{16d}$ wherein R$^{14d}$ and R$^{16d}$ are the same or different C$_{1-3}$ alkyl, and R$^{15d}$ is hydrogen or C$_{1-3}$ alkyl; or C$_{2-3}$ alkenyl optionally substituted by a group selected from the group consisting of the above (a-3) and (b-3), or a pharmaceutically acceptable salt thereof.

14. The compound as claimed in claim 9, wherein A is (3-4) —COR$^{7d}$ wherein R$^{7d}$ is optionally substituted cycloalkyl, optionally substituted cycloalkenyl, optionally substituted monocyclic or bicyclic nonaromatic unsaturated heterocyclyl, or optionally substituted monocyclic saturated heterocyclyl;

provided that if any ring carbon atoms are substituted, then the carbon atoms are optionally substituted by the same or different 1 to 5 substituents selected from halogen, hydroxy, alkyl or alkoxy, and if the ring nitrogen atoms are substituted, then the nitrogen atoms are optionally substituted by alkyl, alkanoyl, alkoxycarbonyl or alkylsulfonyl; or a pharmaceutically acceptable salt thereof.

15. The compound as claimed in claim 9, wherein A is (3-5) —COR$^{7e}$ wherein R$^{7e}$ is optionally substituted aryl or optionally substituted heteroaryl;

provided that if aryl or heteroaryl is substituted, then the aryl and heteroaryl are optionally substituted by the same or different 1 to 5 substituents selected from the group consisting of the following (g-2) to (i-2):

(g-2) halogen, amino, carbamoyl or cyano;

(h-2) —R$^{14e}$, —OR$^{14e}$, —O—COR$^{14e}$, —NR$^{15e}$—COR$^{14e}$, —NR$^{15e}$—COOR$^{14e}$ or —NR$^{15e}$R$^{15e}$R$^{16e}$ wherein R$^{14e}$ and R$^{16e}$ are the same or different and each alkyl, R$^{15e}$ is hydrogen or alkyl; and (i-2) phenyl or phenoxy; or a pharmaceutically acceptable salt thereof.

16. The compound as claimed in claim 9, wherein A is (3-6) —COOR$^{7f}$ wherein R$^{7f}$ is alkyl, alkenyl or optionally substituted phenyl;

provided that if phenyl is substituted, then the phenyl is optionally substituted by the same or different 1 to 5 substituents selected from the group consisting of halogen, nitro, hydroxy, haloalkyl, haloalkoxy, —R$^{14f}$, —OR$^{14f}$ and —COR$^{14f}$ wherein R$^{14f}$ is alkyl; or a pharmaceutically acceptable salt thereof.

17. The compound as claimed in claim 16, wherein R$^{7f}$ is C$_{1-3}$ alkyl or C$_{2-3}$ alkenyl, or a pharmaceutically acceptable salt thereof.

18. The compound as claimed in claim 1, wherein A is (6-1) —CONR$^{12a}$R$^{13a}$, —CSNR$^{12a}$R$^{13a}$ or —SO$_2$NR$^{12a}$R$^{13a}$ wherein R$^{12}$a is hydrogen, C$_{1-3}$ alkyl, C$_{2-3}$ alkenyl, C$_{1-3}$ alkyl substituted by C$_{2-3}$ alkoxycarbonyl, C$_{1-3}$ alkyl substituted by optionally substituted phenyl, or optionally substituted phenyl, provided that if phenyl is substituted, then the phenyl is optionally substituted by the same or different 1 to 5 substituents selected from the group consisting of halogen, nitro, hydroxy, carboxy, haloalkyl, haloalkoxy, amino, carbamoyl, —R$^{14a}$, —OR$^{14a}$, —COR$^{14a}$, —COOR$^{14a}$ and —O—COR$^{14a}$ wherein R$^{14a}$ is alkyl;

R$^{13a}$ is hydrogen or alkyl, or both R$^{12a}$ and R$^{13a}$ may combine each other together with the adjacent nitrogen atom to form optionally substituted saturated or unsaturated 4- to 6-membered monocyclic nitrogen-containing heterocycle containing 1 to 3 heteroatoms selected from the group consisting of 1 to 3 nitrogen, 1 oxygen and 1 sulfur, and the nitrogen atom on the monocyclic nitrogen-containing heterocycle is optionally substituted by alkyl, alkanoyl or alkoxycarbonyl; or a pharmaceutically acceptable salt thereof.

19. The compound as claimed in claim 18, wherein R$^{12a}$ and R$^{13a}$ are the same or different and each C$_{1-3}$ alkyl;

R$^{12a}$ is optionally substituted phenyl wherein phenyl is optionally substituted by 1 to 2 halogen, hydroxy, carboxy, haloalkyl, amino, carbamoyl, —R$^{14a}$, —OR$^{14a}$, —COR$^{14a}$, —COOR$^{14a}$ or —O—COR$^{14a}$ wherein R$^{14a}$ is alkyl, and R$^{13a}$ is hydrogen; or both R$^{12a}$ and R$^{13a}$ combine each other together with the adjacent nitrogen atom to form pyrrolidinyl, piperidinyl, morpholinyl or imidazolyl; or a pharmaceutically acceptable salt thereof.

20. The compound as claimed in claim 1, wherein A is (5-1) —CONR$^{9a}$—OR$^{10a}$ wherein R$^{9a}$ and R$^{10a}$ are the same or different and each alkyl, or a pharmaceutically acceptable salt thereof.

21. The compound as claimed in claim 1, selected from the group consisting of the following compounds:

4-amino-N-[{4-[(1-(1-azetidinecarbonyl)-4-piperidinyl)methyl)]-2-morpholinyl}methyl]-5-chloro-2-ethoxybenzamide;

4-amino-5-chloro-2-methoxy-N-[{4-[(1-pyrrolidinecarbonyl)-4-piperidinyl)methyl]-2-morpholinyl}methyl]benzamide;

4-amino-5-chloro-2-ethoxy-N-[{4-[(1-(1-pyrrolidinecarbonyl)-4-piperidinyl)methyl]-2-morpholinyl}methyl]benzamide;

4-amino-5-chloro-N-[{4-[(1-dimethylcarbamoyl-4-piperidinyl)methyl]-2-morpholinyl}methyl]-2-methoxybenzamide;

4-amino-5-chloro-N-[{4-[(1-dimethylcarbamoyl-4-piperidinyl)methyl]-2-morpholinyl}methyl]-2-ethoxybenzamide;

4-amino-5-chloro-N-[{4-[(1-dimethylthiocarbamoyl-4-piperidinyl)methyl]-2-morpholinyl}methyl]-2-ethoxybenzamide;

4-amino-5-chloro-N-[{4-[(1-dimethylsulfamoyl-4-piperidinyl)methyl)-2-morpholinyl}methyl]-2-methoxybenzamide;

4-amino-5-chloro-N-[{4-[(1-dimethylsulfamoyl-4-piperidinyl)methyl]-2-morpholinyl}methyl]-2-ethoxybenzamide;
4-amino-5-chloro-N-[{4-[(1-dimethylcarbamoyl-4-piperidinyl)methyl]-2-morpholinyl}methyl]-2-isopropoxybenzamide;
4-amino-5-chloro-N-[{4-[(1-diethylcarbamoyl-4-piperidinyl)methyl]-2-morpholinyl}methyl]-2-ethoxybenzamide;
4-amino-5-chloro-N-[{4-[(1-diisopropylcarbamoyl-4-piperidinyl)methyl]-2-morpholinyl}methyl]-2-methoxybenzamide;
6-amino-5-chloro-N-[{4-[(1-dimethylcarbamoyl-4-piperidinyl)methyl]-2-morpholinyl}methyl]-2-methoxypyridine-3-carboxamide;
N-[{4-[(1-allylmethylcarbamoyl-4-piperidinyl)methyl]-2-morpholinyl}methyl]-4-amino-5-chloro-2-ethoxybenzamide;
4-amino-5-chloro-N-[{4-[(1-(1-pyrrolidinecarbonyl)-4-piperidinyl)methyl]-2-morpholinyl}methyl]-2,3-dihydrobenzo[b]furan-7-carboxamide;
4-amino-5-chloro-N-[{4-[(1-dimethylcarbamoyl-4-piperidinyl)methyl]-2-morpholinyl}methyl]-2,3-dihydrobenzo[b]furan-7-carboxamide;
4-amino-5-chloro-2-ethoxy-N-[{4-[(1-methylcarbamoyl-4-piperidinyl)methyl]-2-morpholinyl}-methyl]benzamide;
4-amino-5-chloro-2-ethoxy-N-[{4-[(1-ethylcarbamoyl-4-piperidinyl)methyl]-2-morpholinyl}methyl]benzamide;
4-amino-5-chloro-2-methoxy-N-[{4-[(1-phenylcarbamoyl-4-piperidinyl)methyl]-2-morpholinyl}methyl]benzamide;
4-amino-5-chloro-2-methoxy-N-[{4-[(1-(2-methoxyphenyl)carbamoyl-4-piperidinyl)methyl]-2-morpholinyl}methyl]benzamide;
4-amino-5-chloro-2-methoxy-N-[{4-[(1-(3-trifluoromethylphenyl)carbamoyl-4-piperidinyl)methyl]-2-morpholinyl}methyl]benzamide;
N-[{4-[(1-(3-acetylphenyl)carbamoyl-4-piperidinyl)methyl]-2-morpholinyl}methyl]-4-amino-5-chloro-2-methoxybenzamide;
4-amino-5-chloro-N-[{4-[(1-(3,5-dimethylphenyl)carbamoyl-4-piperidinyl)methyl]-2-morpholinyl}methyl]-2-methoxybenzamide;
4-amino-5-chloro-N-[{4-[(1-(3,4-dichlorophenyl)carbamoyl-4-piperidinyl)methyl]-2-morpholinyl}methyl]-2-methoxybenzamide;
4-amino-N-[{4-[(1-benzylcarbamoyl-4-piperidinyl)methyl]-2-morpholinyl}methyl]-5-chloro-2-methoxybenzamide;
4-amino-5-chloro-2-methoxy-N-[{4-[(1-(2-methylbenzyl)carbamoyl-4-piperidinyl)methyl]-2-morpholinyl}methyl]benzamide;
4-amino-5-chloro-2-methoxy-N-[{4-[(1-(4-methoxybenzyl)carbamoyl-4-piperidinyl)methyl]-2-morpholinyl}methyl]benzamide;
4-amino-5-chloro-N-[{4-[(1-(2,4-dichlorobenzyl)carbamoyl-4-piperidinyl)methyl]-2-morpholinyl}methyl]-2-methoxybenzamide;
4-amino-5-chloro-2-methoxy-N-[{4-[(1-(2-phenethyl)carbamoyl-4-piperidinyl)methyl]-2-morpholinyl}methyl]benzamide;
4-amino-5-chloro-2-ethoxy-N-[{4-[(1-methoxycarbonyl-4-piperidinyl)methyl]-2-morpholinyl}methyl]benzamide;
4-amino-5-chloro-N-[{4-[(1-methanesulfonyl-4-piperidinyl)methyl]-2-morpholinyl}methyl]-2-methoxybenzamide;
amino-5-chloro-2-ethoxy-N-[{4-[(1-methanesulfonyl-4-piperidinyl)methyl]-2-morpholinyl}methyl]benzamide;
4-amino-5-chloro-2-methoxy-N-[{4-[(1-(1-propoxycarbonyl)-4-piperidinyl)methyl]-2-morpholinyl}methyl]benzamide;
N-[{4-[(1-allyloxycarbonyl-4-piperidinyl)methyl]-2-morpholinyl}methyl]-4-amino-5-chloro-2-methoxybenzamide;
4-amino-5-chloro-N-[{4-[(1-isobutoxycarbonyl-4-piperidinyl)methyl]-2-morpholinyl}methyl]-2-methoxybenzamide;
4-amino-5-chloro-2-methoxy-N-[{4-[(1-phenoxycarbonyl-4-piperidinyl)methyl]-2-morpholinyl}methyl]benzamide;
4-amino-5-chloro-2-methoxy-N-[{4-[(1-(2-methoxyphenoxycarbonyl)-4-piperidinyl)methyl]-2-morpholinyl}methyl]benzamide;
N-[{4-[(1-acetoxyacetyl-4-piperidinyl)methyl]-2-morpholinyl}methyl]-4-amino-5-chloro-2-ethoxybenzamide;
4-amino-5-chloro-N-[{4-[(1-(1-cyclopentenecarbonyl)-4-piperidinyl)methyl]-2-morpholinyl}methyl]-2-ethoxybenzamide;
4-amino-5-chloro-N-[{4-[(1-(2-cyclopropylvinylcarbonyl)-4-piperidinyl)methyl]-2-morpholinyl}methyl]-2-ethoxybenzamide;
4-amino-5-chloro-2-ethoxy-N-[{4-[(1-[2-(furan-2-yl)vinylcarbonyl]-4-piperidinyl)methyl]-2-morpholinyl}methyl]benzamide;
4-amino-5-chloro-2-ethoxy-N-[{4-[(1-[2-(thiophen-2-yl)vinylcarbonyl]-4-piperidinyl)methyl]-2-morpholinyl}methyl]benzamide;
4-amino-N-[{4-[(1-(3-butenecarbonyl)-4-piperidinyl)methyl]-2-morpholinyl}methyl]-5-chloro-2-ethoxybenzamide;
4-amino-5-chloro-2-ethoxy-N-[{4-[(1-(5-hexenecarbonyl)-4-piperidinyl)methyl]-2-morpholinyl}methyl]benzamide;
4-amino-N-[{4-[(1-(1,3-butadienecarbonyl)-4-piperidinyl)methyl]-2-morpholinyl}methyl]-5-chloro-2-ethoxybenzamide;
4-amino-5-chloro-2-ethoxy-N-[{4-[(1-(1,5-hexadienecarbonyl)-4-piperidinyl)methyl]-2-morpholinyl}methyl]benzamide;
4-amino-N-[{4-[(1-[1-(1-propyne)carbonyl]-4-piperidinyl)methyl]-2-morpholinyl}methyl]-5-chloro-2-ethoxybenzamide;
4-amino-5-chloro-N-[{4-[(1-methoxycarbonyl-4-piperidinyl)methyl]-2-morpholinyl}methyl]-2,3-dihydrobenzo[b]furan-7-carboxamide;
N-[{4-[(1-acetyl-4-piperidinyl)methyl]-2-morpholinyl}methyl]-4-amino-5-chloro-2,3-dihydrobenzo[b]furan-7-carboxamide;
4-amino-5-chloro-N-[{4-[(1-methanesulfonyl-4-piperidinyl)methyl]-2-morpholinyl}methyl]-2,3-dihydrobenzo[b]furan-7-carboxamide;
4-amino-N-[{4-[(1-benzoyl-4-piperidinyl)methyl]-2-morpholinyl}methyl]-5-chloro-2-ethoxybenzamide;
4-amino-5-chloro-N-[{4-[(1-(3-fluorobenzoyl)-4-piperidinyl)methyl]-2-morpholinyl}methyl]-2-methoxybenzamide;

4-amino-5-chloro-2-ethoxy-N-[{4-[(1-(3-fluorobenzoyl)-4-piperidinyl)methyl]-2-morpholinyl}-methyl]benzamide;

4-amino-5-chloro-N-[{4-[(1-(4-chlorobenzoyl)-4-piperidinyl)methyl]-2-morpholinyl}methyl]-2-methoxybenzamide;

4-amino-5-chloro-N-[{4-[(1-(4-chlorobenzoyl)-4-piperidinyl)methyl]-2-morpholinyl}methyl]-2-ethoxybenzamide;

4-amino-N-[{4-[(1-(3-bromobenzoyl)-4-piperidinyl)methyl]-2-morpholinyl}methyl]-5-chloro-2-methoxybenzamide;

4-amino-5-chloro-2-methoxy-N-[{4-[(1-(2-methylbenzoyl)-4-piperidinyl)methyl]-2-morpholinyl}methyl]benzamide;

4-amino-5-chloro-2-methoxy-N-[{4-[(1-(3-methylbenzoyl)-4-piperidinyl)methyl]-2-morpholinyl}methyl]benzamide;

4-amino-5-chloro-2-methoxy-N-[{4-[(1-(4-methylbenzoyl)-4-piperidinyl)methyl]-2-morpholinyl}methyl]benzamide;

4-amino-5-chloro-2-ethoxy-N-[{4-[(1-(4-methylbenzoyl)-4-piperidinyl)methyl]-2-morpholinyl}-methyl]benzamide;

4-amino-5-chloro-N-[{4-[(1-(4-ethylbenzoyl)-4-piperidinyl)methyl]-2-morpholinyl}methyl]-2-methoxybenzamide;

4-amino-N-[{4-[(1-(tert-butylbenzoyl)-4-piperidinyl)methyl]-2-morpholinyl}methyl]-5-chloro-2-methoxybenzamide;

4-amino-5-chloro-N-[{4-[(1-(3-hydroxybenzoyl)-4-piperidinyl)methyl]-2-morpholinyl}methyl]-2-methoxybenzamide;

4-amino-5-chloro-N-[{4-[(1-(4-hydroxybenzoyl)-4-piperidinyl)methyl]-2-morpholinyl}methyl]-2-methoxybenzamide;

N-[{4-[(1-(2-acetoxybenzoyl)-4-piperidinyl)methyl]-2-morpholinyl}methyl]-4-amino-5-chloro-2-methoxybenzamide;

N-[{4-[(1-(2-acetoxybenzoyl)-4-piperidinyl)methyl]-2-morpholinyl}methyl]-4-amino-5-chloro-2-ethoxybenzamide;

N-[{4-[(1-(3-acetoxybenzoyl)-4-piperidinyl)methyl]-2-morpholinyl}methyl]-4-amino-5-chloro-2-methoxybenzamide;

N-[{4-[(1-(4-acetoxybenzoyl)-4-piperidinyl)methyl]-2-morpholinyl}methyl]-4-amino-5-chloro-2-methoxybenzamide;

4-amino-5-chloro-2-methoxy-N-[{4-[(1-(3-methoxybenzoyl)-4-piperidinyl)methyl]-2-morpholinyl}methyl]benzamide;

4-amino-5-chloro-2-methoxy-N-[{4-[(1-(4-methoxybenzoyl)-4-piperidinyl)methyl]-2-morpholinyl}methyl]benzamide;

4-amino-5-chloro-2-ethoxy-N-[{4-[(1-(4-methoxybenzoyl)-4-piperidinyl)methyl]-2-morpholinyl}methyl]benzamide;

4-amino-5-chloro-2-methoxy-N-[{4-[(1-(2-phenoxybenzoyl)-4-piperidinyl)methyl]-2-morpholinyl}methyl]benzamide;

4-amino-5-chloro-N-[{4-[(1-(3-dimethylaminobenzoyl)-4-piperidinyl)methyl]-2-morpholinyl}methyl]-2-methoxybenzamide;

4-amino-5-chloro-N-[{4-[(1-(4-dimethylaminobenzoyl)-4-piperidinyl)methyl]-2-morpholinyl}methyl]-2-methoxybenzamide;

4-amino-5-chloro-2-methoxy-N-[{4-[(1-(4-methoxycarbonylbenzoyl)-4-piperidinyl)methyl]-2-morpholinyl}methyl]benzamide;

4-amino-5-chloro-2-methoxy-N-[{4-[(1-(4-phenylbenzoyl)-4-piperidinyl)methyl]-2-morpholinyl}methyl]benzamide;

4-amino-N-[{4-[1(-(4-amino-3-chlorophenylbenzoyl)-4-piperidinyl)methyl]-2-morpholinyl}methyl]-5-chloro-2-methoxybenzamide;

4-amino-5-chloro-N-[{4-[(1-(2-furancarbonyl)-4-piperidinyl)methyl]-2-morpholinyl}methyl]-2-methoxybenzamide;

4-amino-5-chloro-N-[{4-[(1-(1-imidazolecarbonyl)-4-piperidinyl)methyl]-2-morpholinyl}methyl]-2-methoxybenzamide;

4-amino-5-chloro-N-[{4-[(1-[(1,2-dihydrobenzofuran-7-yl)carbonyl]-4-piperidinyl)methyl]-2-morpholinyl}methyl]-2-methoxybenzamide;

4-amino-5-chloro-2-methoxy-N-[{4-[(1-[(5-methylthiophen-2-yl)carbonyl]-4-piperidinyl)methyl]-2-morpholinyl}methyl]benzamide;

4-amino-5-chloro-2-methoxy-N-[{4-[(1-[(S)-2-tetrahydrofurylcarbonyl]-4-piperidinyl)methyl]-2-morpholinyl}methyl]benzamide;

4-amino-5-chloro-2-methoxy-N-[{4-[(1-methoxyacetyl-4-piperidinyl)methyl]-2-morpholinyl}-methyl]benzamide;

4-amino-5-chloro-2-ethoxy-N-[{4-[(1-methoxyacetyl-4-piperidinyl)methyl)-2-morpholinyl}methyl]benzamide;

4-amino-5-chloro-N-[{4-[(1-hydroxyacetyl-4-piperidinyl)methyl]-2-morpholinyl}methyl]-2-methoxybenzamide;

4-amino-5-chloro-2-ethoxy-N-[{4-[(1-hydroxyacetyl-4-piperidinyl)methyl]-2-morpholinyl}methyl]benzamide;

4-amino-5-chloro-N-[{4-[(1-hydroxyacetyl-4-piperidinyl)methyl]-2-morpholinyl}methyl]-2,3-dihydrobenzo[b]furan-7-carboxamide;

4-amino-5-chloro-2-methoxy-N-[{4-[(1-(4-piperidinyl)methylcarbonyl)-4-piperidinyl)methyl]-2-morpholinyl}methyl]benzamide;

N-[{4-[(1-acetyl-4-piperidinyl)methyl]-2-morpholinyl}methyl]-4-amino-5-chloro-2-methoxybenzamide;

4-amino-N-[{4-[(1-benzoylaminoacetyl-4-piperidinyl)methyl]-2-morpholinyl}methyl]-5-chloro-2-methoxybenzamide;

4-amino-5-chloro-N-[{4-[(1-cyanoacetyl-4-piperidinyl)methyl]-2-morpholinyl}methyl]-2-methoxybenzamide;

4-amino-5-chloro-N-{[4-{[1-(3-methoxypropionyl)-4-piperidinyl]methyl}-2-morpholinyl]methyl}-2-methoxybenzamide;

4-amino-5-chloro-N-{[4-{[1-((S)-2-methoxypropionyl)-4-piperidinyl]methyl}-2-morpholinyl]methyl}-2-methoxybenzamide;

4-amino-5-chloro-2-methoxy-N-{[4-{[1-(3-tetrahydrofurylcarbonyl)-4-piperidinyl]methyl}-2-morpholinyl]methyl}benzamide;

4-amino-5-chloro-N-{[4-{[1-(1,2-dioxopropyl)-4-piperidinyl]methyl}-2-morpholinyl]methyl}-2-methoxybenzamide;

4-amino-5-chloro-2-methoxy-N-{[4-{[1-(4-oxazolylcarbonyl)-4-piperidinyl]methyl}-2-morpholinyl]methyl}benzamide;

4-amino-5-chloro-2-methoxy-N-{[4-{[1-(3-triazolylcarbonyl)-4-piperidinyl]methyl}-2-morpholinyl]methyl}benzamide;

4-amino-5-chloro-N-{[4-{[1-(4-cyanobenzoyl)-4-piperidinyl]methyl}-2-morpholinyl]methyl}-2-methoxybenzamide;

N-[{4-[(1-acetyl-4-piperidinyl)methyl]-2-morpholinyl}methyl]-4-amino-5-chloro-2,3-dihydrobenzo[b]furan-7-carboxamide;

4-amino-5-chloro-N-{[4-{[1-(3-tetrahydrofurylcarbonyl)-4-piperidinyl]methyl}-2-morpholinyl]-methyl}-2,3-dihydrobenzo[b]furan-7-carboxamide; and 4-amino-5-chloro-N-[{4-[(1-hydroxyacetyl-4-piperidinyl)methyl]-2-morpholinyl]methyl]-2,3-dihydrobenzo[b]furan-7-carboxamide; or a pharmaceutically acceptable salt thereof.

22. The compound as claimed in claim 21, wherein a carbon atom on 2-position of morpholinyl is in S-configuration.

23. (S)-4-Amino-5-chloro-N-[{4-[(1-dimethylcarbamoyl-4-piperidinyl)-methyl]-2-morpholinyl}methyl]-2-ethoxybenzamide.

24. (S)-4-Amino-5-chloro-N-[{4-[(1-methanesulfonyl-4piperdinyl)-methyl]-2-morpholinyl}methyl]-2-methoxybenzamide.

25. (S)-4-Amino-5-chloro-2-ethoxy-N-[{4-[(1-(4-methylbenzoyl)-4-piperidinyl)-methyl]-2-morpholinyl}methyl[-benzamide.

26. (S)-4-Amino-5-chloro-N-[{4-[(1-hydroxyacetyl-4-piperidinyl)-methyl]-2-morpholinyl}methyl]-2-methoxybenzamide hydrobromide 2 hydrate.

27. (S)-4-Amino-5-chloro-N-[{4-[(14(S)-2-methoxypropionyl)-4-piperidinyl]-methyl}-2-morpholinyl]methyl}-2-methoxybenzamide.

28. A pharmaceutical composition, comprising the compound as claimed in any one of claims 1 to 27 or a pharmaceutically acceptable salt thereof.

29. A serotonin 4 receptor agonist, comprising as an active ingredient the compound as claimed in any one of claims 1 to 27 or a pharmaceutically acceptable salt thereof.

30. An enterokinesis-promoting agent or digestive tract function-improving agent, comprising as an active ingredient the compound as claimed in any one of claims 1 to 27 or a pharmaceutically acceptable salt thereof.

* * * * *